United States Patent
Wolfe

(10) Patent No.: US 9,284,487 B2
(45) Date of Patent: Mar. 15, 2016

(54) UP-CONVERSION LUMINESCENT COATINGS/MATERIALS FOR ANTIMICROBIAL APPLICATIONS

(75) Inventor: Douglas E. Wolfe, St. Marys, PA (US)

(73) Assignee: The Penn State Research Foundation, University Park, PA (US)

( * ) Notice: Subject to any disclaimer, the term of this patent is extended or adjusted under 35 U.S.C. 154(b) by 348 days.

(21) Appl. No.: 13/006,113

(22) Filed: Jan. 13, 2011

(65) Prior Publication Data

US 2011/0171062 A1 Jul. 14, 2011

Related U.S. Application Data

(60) Provisional application No. 61/294,638, filed on Jan. 13, 2010.

(51) Int. Cl.
*A61L 2/10* (2006.01)
*C09K 11/77* (2006.01)
*A61L 2/232* (2006.01)

(52) U.S. Cl.
CPC .............. *C09K 11/7774* (2013.01); *A61L 2/10* (2013.01); *A61L 2/232* (2013.01); *C09K 11/7792* (2013.01)

(58) Field of Classification Search
CPC ............ A61L 2/08; A61L 2/10; A61K 33/24; G21G 33/24
USPC .......................................................... 422/22
See application file for complete search history.

(56) References Cited

U.S. PATENT DOCUMENTS

| | | | |
|---|---|---|---|
| 2,320,842 A | 6/1943 | Arnold et al. | |
| 2,976,716 A | 3/1961 | De Haven | |
| 3,995,157 A | 11/1976 | Holub et al. | |
| 4,327,155 A | 4/1982 | Hanneman | |
| 6,974,641 B1 | 12/2005 | Choy et al. | |
| 2008/0305244 A1 | 12/2008 | Cui et al. | |
| 2009/0104130 A1 | 4/2009 | Bernstein et al. | |
| 2009/0130169 A1 | 5/2009 | Bernstein | |
| 2009/0294692 A1 | 12/2009 | Bourke, Jr. et al. | |
| 2010/0261263 A1 | 10/2010 | Vo-Dinh et al. | |
| 2010/0297206 A1 | 11/2010 | Kim et al. | |

FOREIGN PATENT DOCUMENTS

| | | |
|---|---|---|
| WO | 95/32060 A1 | 11/1995 |
| WO | 02/28973 A1 | 4/2002 |
| WO | 02/071045 A2 | 9/2002 |

OTHER PUBLICATIONS

The Penn State Research Foundation, PCT/US11/21155, International Search Report dated Mar. 22, 2011, 10 pages.
Hirai, Takayuki et al, "Preparation of Y2O3:Yb, ER Infrared-to-Visible Conversaion Phosphor Fine Particles Using an Emulsion Liquid Membrane System", Chem. Mater. 2002, 14, pp. 3576-3583.
Molecular Expressions (TM), "Optical Microscopy Primer, Specialized Techniques, Fluorescence Microsophy, Basic Concepts in Fluorescence", http://micro.magnet.fsu.edu/primer/techniques/fluorescence/fluorescenceintro.html (1 of 21) printed Jul. 8, 2010.
The Penn State Research Foundation, PCT/US2010/030549, International Search Report and the Written Opinion of the International Searching Authority, Jun. 17, 2010, 14 pages.
Article from Science & Technology Concentrates, Aug. 30, 2010, p. 25, www.cen-online.org.

*Primary Examiner* — Sean E Conley
(74) *Attorney, Agent, or Firm* — McKee, Voorhees & Sease, PLC

(57) ABSTRACT

The present invention provides continuous, non-hazardous sterilization and anti-microorganism protection by the generation of interactive, emission responsive surfaces, coatings, and coating systems.

20 Claims, 61 Drawing Sheets

UP-CONVERSION LUMINESCENT COATINGS/MATERIALS FOR ANTIMICROBIAL APPLICATIONS

CROSS-REFERENCE TO RELATED APPLICATIONS

This application claims priority under 35 U.S.C. §120 to provisional application Ser. No. 61/294,638 filed Jan. 13, 2010, herein incorporated by reference in its entirety.

FIELD OF THE INVENTION

The present invention relates generally to coatings and surfaces comprising embedded Rare Earth doped particles tailored to up-convert low energy wavelengths to higher energy wavelengths to emit an ultraviolet response in a typical wavelength range known to kill bacteria and viruses.

BACKGROUND OF THE INVENTION

The statements in this section merely provide background information related to the present invention and may not constitute prior art.

Hospitals and doctor's offices, food preparation areas, and public areas are breeding grounds for dangerous bacteria and viruses. According to the Center for Disease Control (CDC), in American hospitals alone, healthcare-associated infections (also called nonsocomial infections) account for an estimated 1.7 million infections and 99,000 associated deaths each year. A recent study reports that the annual direct medical costs from these healthcare-associated infections to U.S. hospitals ranges from $35.7 billion to $45 billion. Along with these direct costs come indirect costs, which can be just as damaging as loss of money. Examples of some indirect costs are lost wages, diminished worker productivity on the job, short and long term morbidity, mortality, income lost by family members, forgone leisure time, and time spent by family/friends for hospital visits, travel costs, and home care. Millions of other people are infected by food poisoning brought on by food being cross-contaminated and prepared in unclean areas. The cost for these food borne illnesses are about $35 billion, consisting of health care costs and lost productivity.

Bacteria and viruses are able to live and grow in a wide spectrum of conditions. One thing is key, however, and that is that the bacteria or viruses must be introduced to the location. They are not able to spontaneously appear. Many patients who go to healthcare facilities go because they are ill, and certain bacteria or viruses cause the illnesses. During their check-ups or treatments, the patients introduce the bacteria and viruses to the rooms. Infections occur when health care rooms do not get sterilized thoroughly. Bacteria and viruses will continue to live, and possibly even multiply in an area thought to be clean. A patient reports to the room during their visit, and the bacteria or virus may infect the patient. Patients have a greater risk of infection because they are usually in a weakened health position due to the illness or injury that brought them to the health care facility in the first place.

Wiping down the surfaces and floors of healthcare rooms with disinfectants has been the primary way to sterilize the rooms. The scope of cleaning is limited to the time and effort put in by the person or people cleaning the room. Additionally, in recent years, some bacteria and viruses have developed resistances to the standard disinfectants. Therefore, there is need in the art to provide a coating on the surfaces and floors of healthcare rooms to provide for continuous, uniform sterilization, thus resulting in lower levels of bacteria and viruses resulting in fewer cases of nonsocomial infections.

Another technique used to clean healthcare rooms is with the use of gases such as formaldehyde or chlorine dioxide. The gases are pumped into the healthcare facilities for a set period of time and the gases kill the bacteria and viruses. Along with being questioningly effective, the gases used are extremely toxic to people. For example, some scientists believe that chlorine dioxide may actually leave crystals behind which would aid the regeneration of mold it is intended to kill. Additionally, Chlorine dioxide is a severe respiratory and eye irritant in humans. Therefore, to use the gases to sterilize (i.e., fumigate), the healthcare facilities, as well as the surrounding areas, must be shut down and everyone must be evacuated for a certain amount of time. The gases must be given time to work, and then to disperse enough for it to be safe for people to reenter the facilities. The closure of the healthcare facilities creates difficulties where people are forced to obtain treatment at unfamiliar or inconvenient places.

Direct ultraviolet (UV) sterilization has shown to be an effective way of sterilizing healthcare rooms. For example, U.S. Pat. No. 5,920,075 to Whitehead discloses the use of ultraviolet radiation, from an ultraviolet light source, in a range sufficient to eradicate germs, bacteria, viruses, and other pathogens and microorganisms. U.S. Pat. No. 6,656,424 to Deal (the "424 patent") teaches the use of a mobile ultraviolet generator, which first scans the room to make sure everyone has evacuated, and then generates UV-C radiation to sterilize the room. Direct UV sterilization does have a similar problem to gas sterilization, however. UV rays are harmful to humans, especially in higher amounts of exposure. UV rays can cause sunburn, skin cancer, and aging of the skin, as well as cataracts and pinguecula in the eyes. Therefore, direct UV sterilization, as described in the '424 patent, can only occur when no humans are in a room.

The present invention addresses needs in the art improvements in the self-sterilization of hospital surfaces from ambient or direct lighting stimulation, food preparation surfaces, public or private bathrooms, dining tables, and public surfaces.

BRIEF SUMMARY OF THE INVENTION

Further areas of applicability of the present invention will become apparent from the description provided herein. It should be understood that the description includes specific examples that are intended for purposes of illustration and are not intended to limit the scope of the present teachings.

In one aspect of the present invention, a material surface or coating system for antimicrobial applications is disclosed. The coating system includes a coating comprised of interactive materials adapted to have an antimicrobial emission response. The interactive material is stimulated by a light source thereby providing an emission response having a wavelength suitable for use in antimicrobial applications.

BRIEF DESCRIPTION OF THE DRAWINGS

The drawings described herein are for illustration purposes only and are not intended to limit the scope of the present disclosure in any way.

FIG. 10($b$) is a graph of x-ray diffraction data for Y$_2$O$_3$ starting powder showing the monoclinic crystal structure.

FIG. 10($c$) is a graph of x-ray diffraction data for YAP1 showing the orthorhombic crystal structure.

FIG. 10($d$) is a graph of x-ray diffraction data for YAP2 showing the orthorhombic crystal structure.

FIG. 10($e$) is a graph of x-ray diffraction data for YAP3 showing several phases being present suggesting a processing error.

FIG. 10($f$) is a graph of x-ray diffraction data for YAP4 showing several phases being present suggesting a processing error.

FIG. 10($g$) is a graph of x-ray diffraction data for YAP5 showing that it is primarily of the orthorhombic crystal structure.

FIG. 10($h$) is a graph of x-ray diffraction data for YAP6 showing that it is primarily of the orthorhombic crystal structure.

FIG. 10($i$) is a graph of x-ray diffraction data for YAP7 showing that it is primarily of the orthorhombic crystal structure.

FIG. 10($j$) is a graph of x-ray diffraction data for YAP8 showing that it is primarily of the orthorhombic crystal structure.

FIG. 10($k$) is a graph of x-ray diffraction data for YAP11 showing that it is primarily of the orthorhombic crystal structure.

FIG. 10($l$) is a graph of x-ray diffraction data for YAP12 showing that it is primarily of the orthorhombic crystal structure.

FIG. 11($b$) is a graph of collected data from a known emission source verifying correct operation of the portable test configuration.

FIG. 27($b$) is a graph of FIG. 27($a$) showing wavelength ranging from 200-320 nm.

FIG. 28($b$) is a graph of FIG. 28($a$) showing wavelength ranging from 200-320 nm.

FIG. 29($b$) is a graph of FIG. 29($a$) showing wavelength ranging from 200-320 nm.

FIG. 30($b$) is a graph of FIG. 30($a$) showing wavelength ranging from 200-320 nm.

FIG. 31($b$) is a graph of FIG. 31($a$) showing wavelength ranging from 200-320 nm.

DETAILED DESCRIPTION OF THE PREFERRED EMBODIMENT

The following description is merely exemplary in nature and is not intended to limit the present disclosure, application, or uses.

Figure 1:
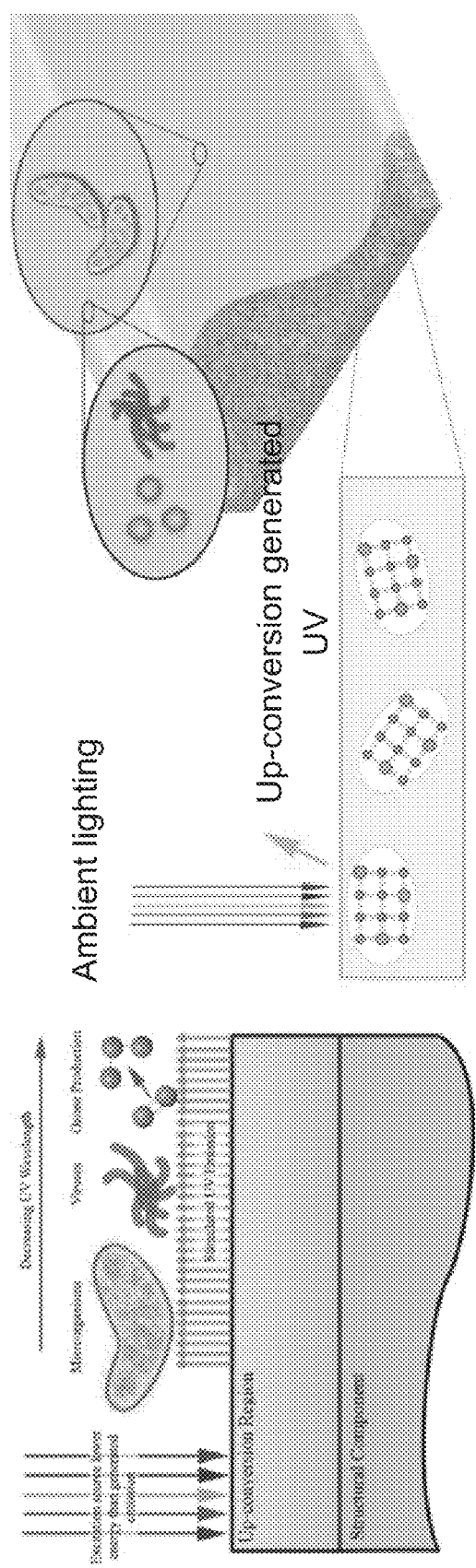
FIG. 1 is a schematic representation of an up-conversion system for killing bacteria and viruses.

The present invention generally provides for a technique for the sterilization of surfaces and floors in health care facilities, food preparation areas, kitchens, bathrooms, and other general public areas. A further aspect of the invention is to provide surfaces or coatings that produce ultraviolet (UV) light from lower energy sources, where the UV light will continuously bombard microorganisms on the surface or coating, or near the surface or coating with UV radiation to inhibit growth and ultimately kill the microorganisms as seen in FIG. 1. An additional aspect of the present invention provides that the UV radiation from the coatings breaks down bacteria and virus' cell walls, disrupts their cell DNA (effectively stopping reproduction), and compromises cell membranes (effectively killing the organism). Another aspect of the current invention uses coatings that are tailored to use safe infrared or visible light as a stimulation source resulting in constant sterilization of the illuminated surface as illustrated also in FIG. 1. A further yet aspect of the invention provides self-sterilizing hospital surfaces, self-sterilizing food preparation surface, and self-sterilizing public surfaces from ambient or direct lighting stimulation. An advantage of the current invention is that it does not require ion transport through the coating or surface to kill bacteria. The invention will continue to work even if there is a layer of dead bacteria, because it functions with UV, which can penetrate layers of bacteria.

In another aspect of the current invention the surfaces or coatings could be incorporated into UV emitting "Smart Walls" and "Bio-Flooring". Another embodiment of the invention includes the coatings consisting of paint, epoxies, urethane, inorganic, organic, or mixed combinations. The surface or coating material could be crystalline, amorphous, or a mixed combination. These surfaces can be stimulated from ambient light or from generated sources such as infrared spotlighting and be tailored to provide UV emission having a wavelength between 200-450 nm for killing bacteria and viruses. According to another feature of the invention, the intensity of the UV drastically decreases as a function of distance from the surface of the wall or floor, so human exposure to UV can be tailored/minimized. In a further aspect of the invention the UV emitters could be incorporated directly into flooring (carpet, glass tiles, ceramic tiles, polymer-based tiles, etc.), emergency services, or military tents and mobile structures. In another embodiment, the UV emitters may be present in a coating system or material surface as a second phase, such as a pigment, or they may be present in the luminescent center, which may be inseparable from the coating system, such as a molecular side or end group attached to one of the primary or secondary components of the coating system. In a preferred form, the invention provides for UV emitters present in a coating system or material surface as a second phase particulate for providing an emission response for killing bacteria and viruses. In addition, the coating system could be applied as a thin layer or coating by any energy enhanced deposition methods (plasma, laser, etc.), chemical vapor deposition (CVD), or physical vapor deposition (PVD) methods including, but not limited to, direct evaporation, reactive evaporation, reactive ion beam assisted EB-PVD, sputtering (dc, rf, magnetron, unbalanced, balanced, ion beam sputtering, diode), atomic layer deposition (ALD), cathodic arc, thermal spray technologies, plasma spray processes, energy enhanced or hybrid coating methods, sol-gel, polymer processing methods, electrophoretic, etc. onto a polymer, metallic, ceramic, composite, MMC, CMC, or mixed combination surface. The thickness can range from nanometers to several millimeters thick.

Figure 2:
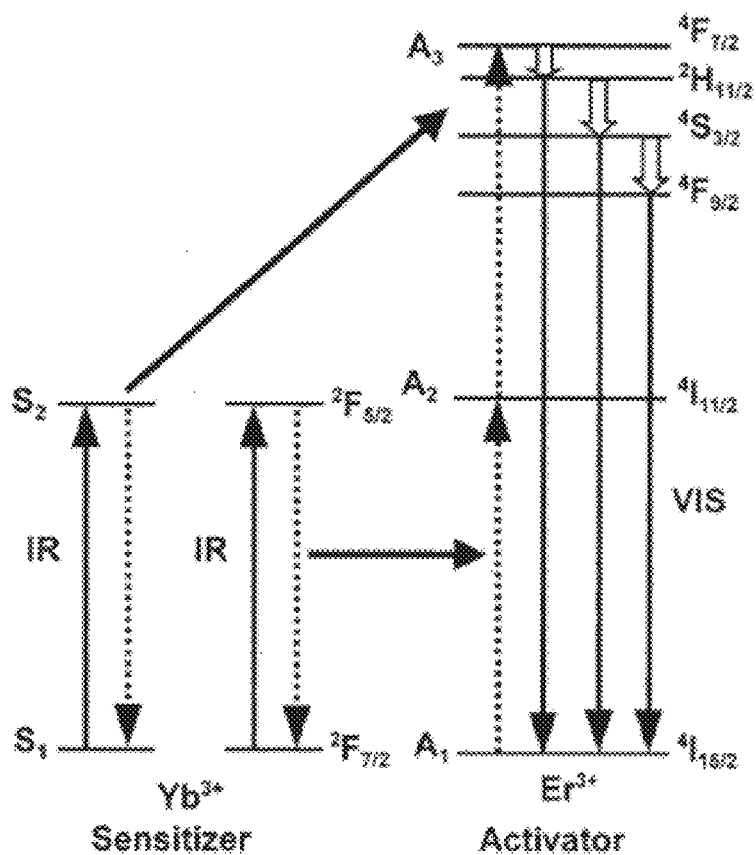
FIG. 2 is a schematic representation of Yb (sensitizer) Er (Activator) up-conversion process of the present invention.
Figure 3:
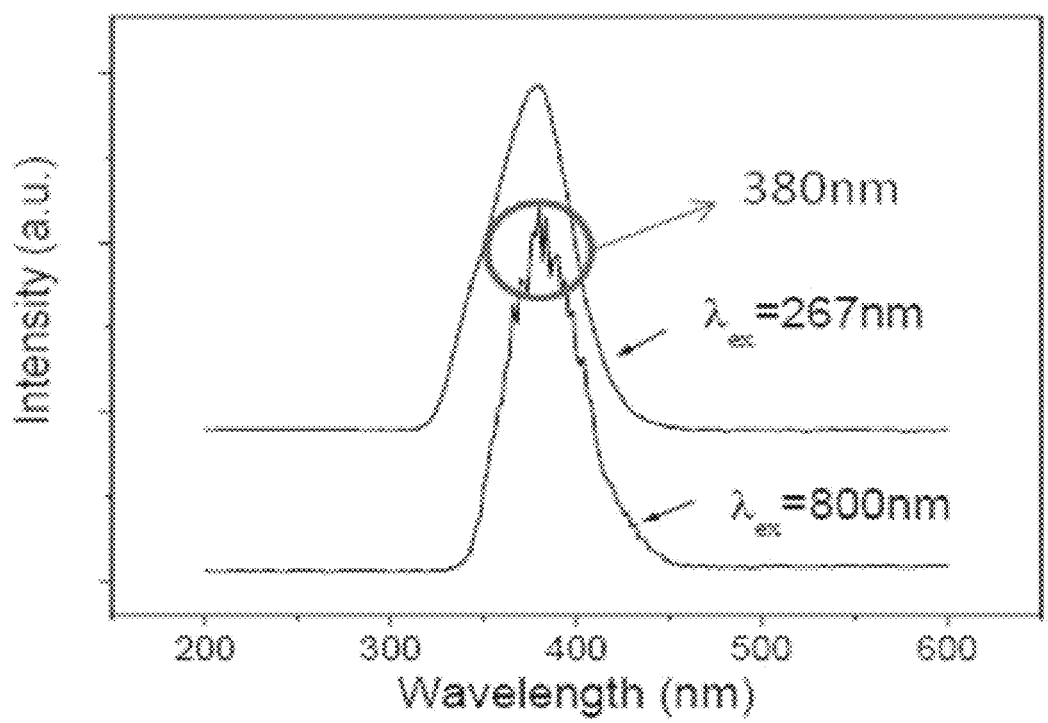
FIG. 3 is a graph of the emission spectra of YAlO$_3$:Ce$^{3+}$ (IR up-conversion) using an 800 nm femtosecond laser for excitation.
Figure 4:
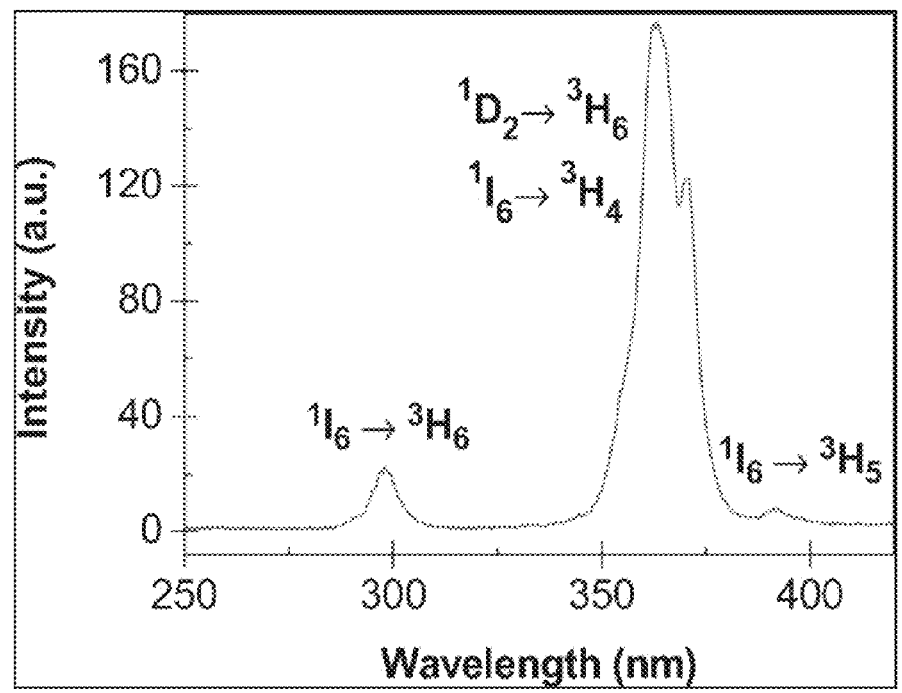
FIG. 4 is a graph of the emission spectra of Y$_2$O$_3$ powder co-doped with Tm$^{3+}$ and Yb$^{3+}$ in the 250-420 nm wavelength range.
Figure 5:
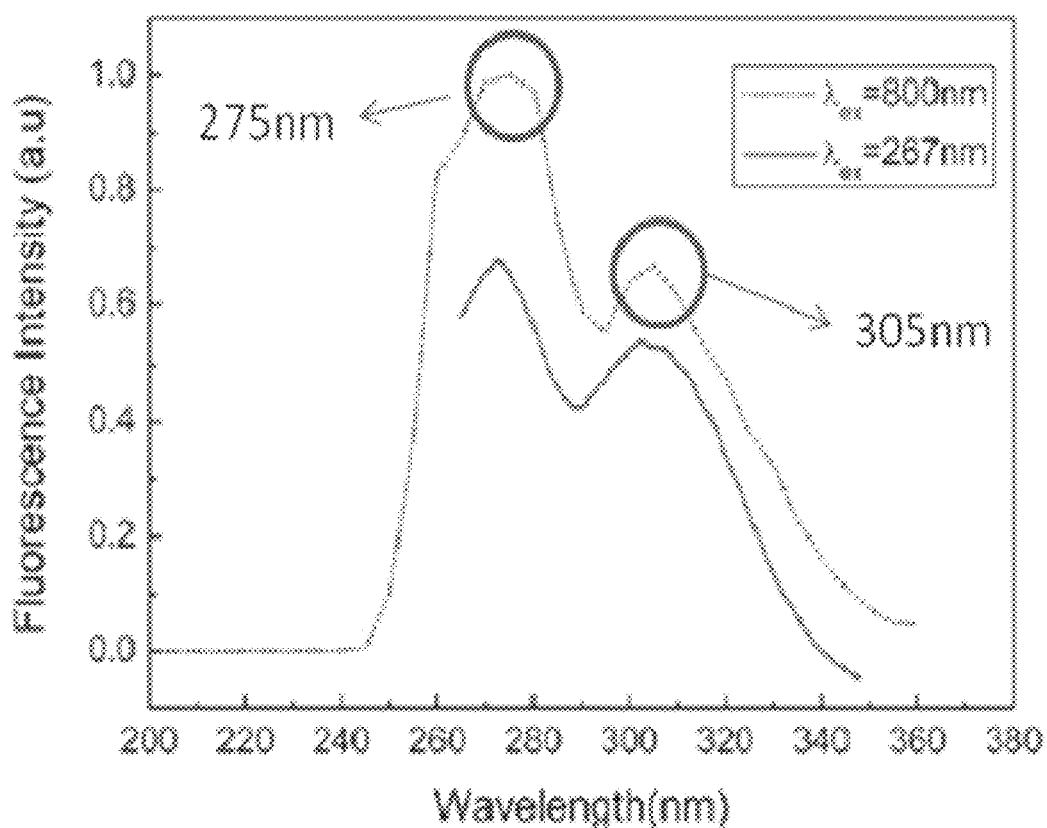
FIG. 5 is a plot illustrating of the Y$_2$SiO$_5$:Pr$^{3+}$ (IR up-conversion to UV) emission spectra under 800 nm infrared laser excitation.
Figure 6:
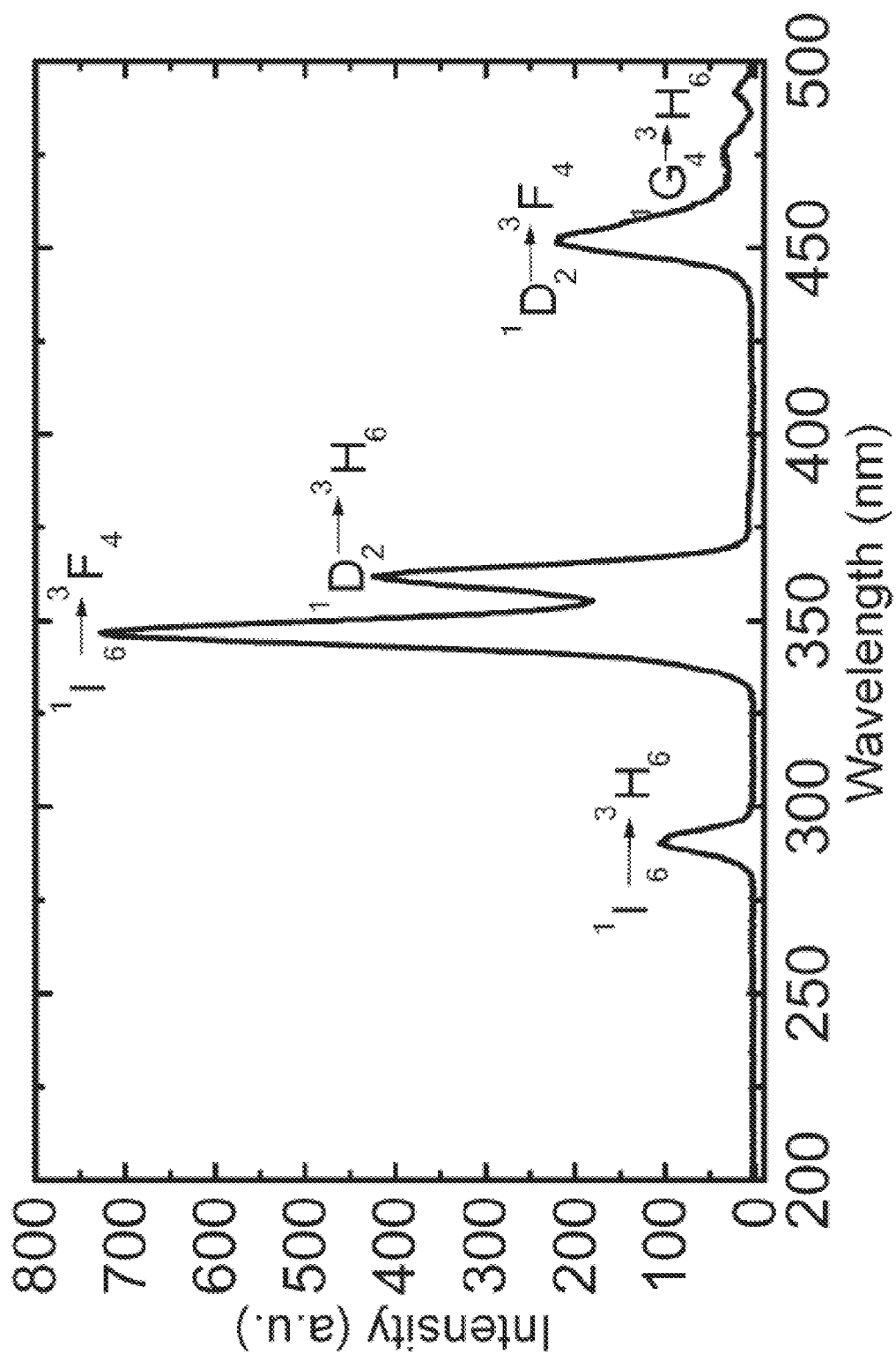
FIG. 6 is a plot illustrating of the emission spectra of AlF$_3$:Tm$^{3+}$,Yb$^{3+}$.
Figure 7:
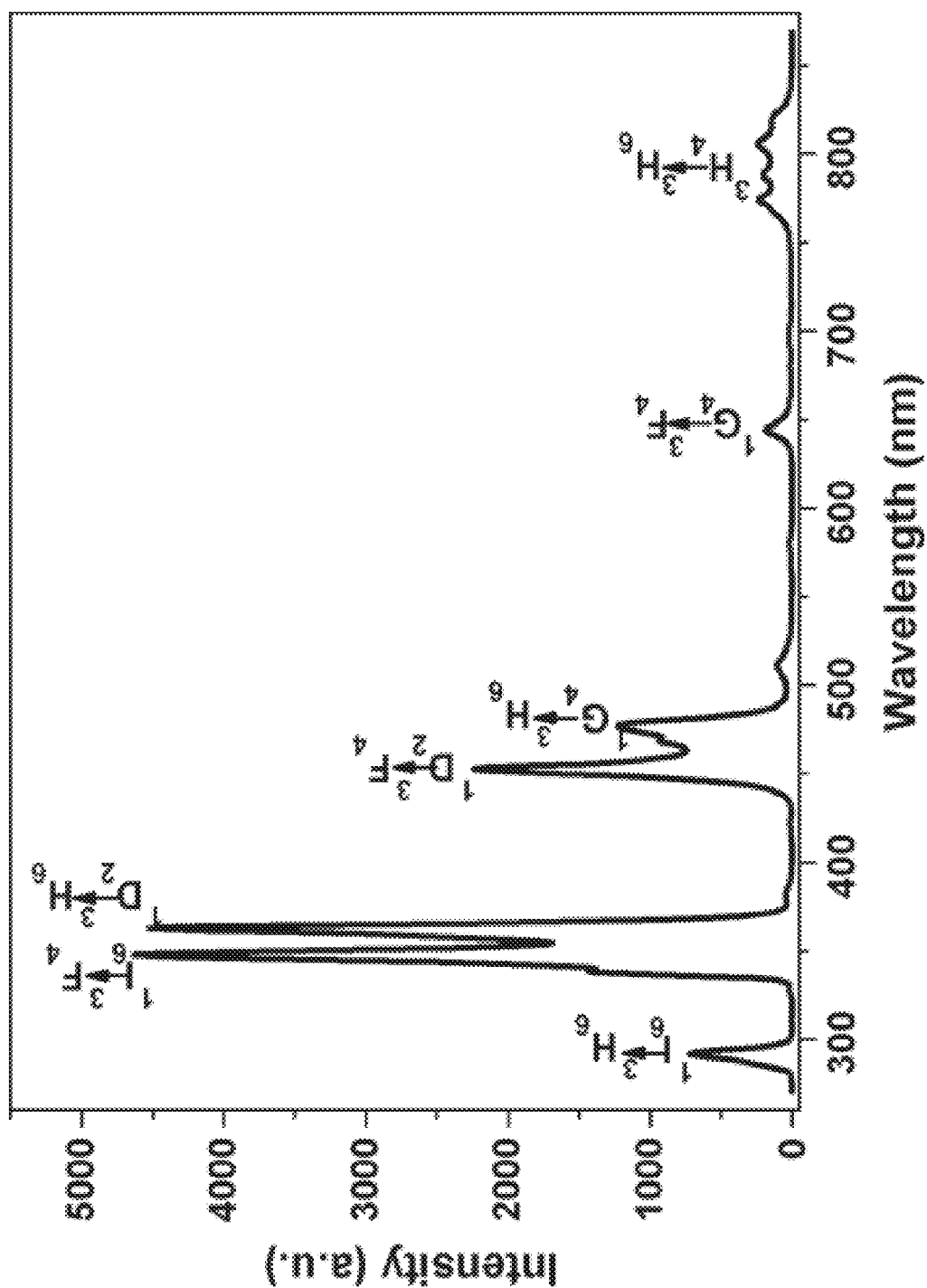
FIG. 7 is a plot illustrating of the emission spectra of Y$_{0.797}$Yb$_{0.2}$Tm$_{0.003}$F$_3$.
Figure 8A:
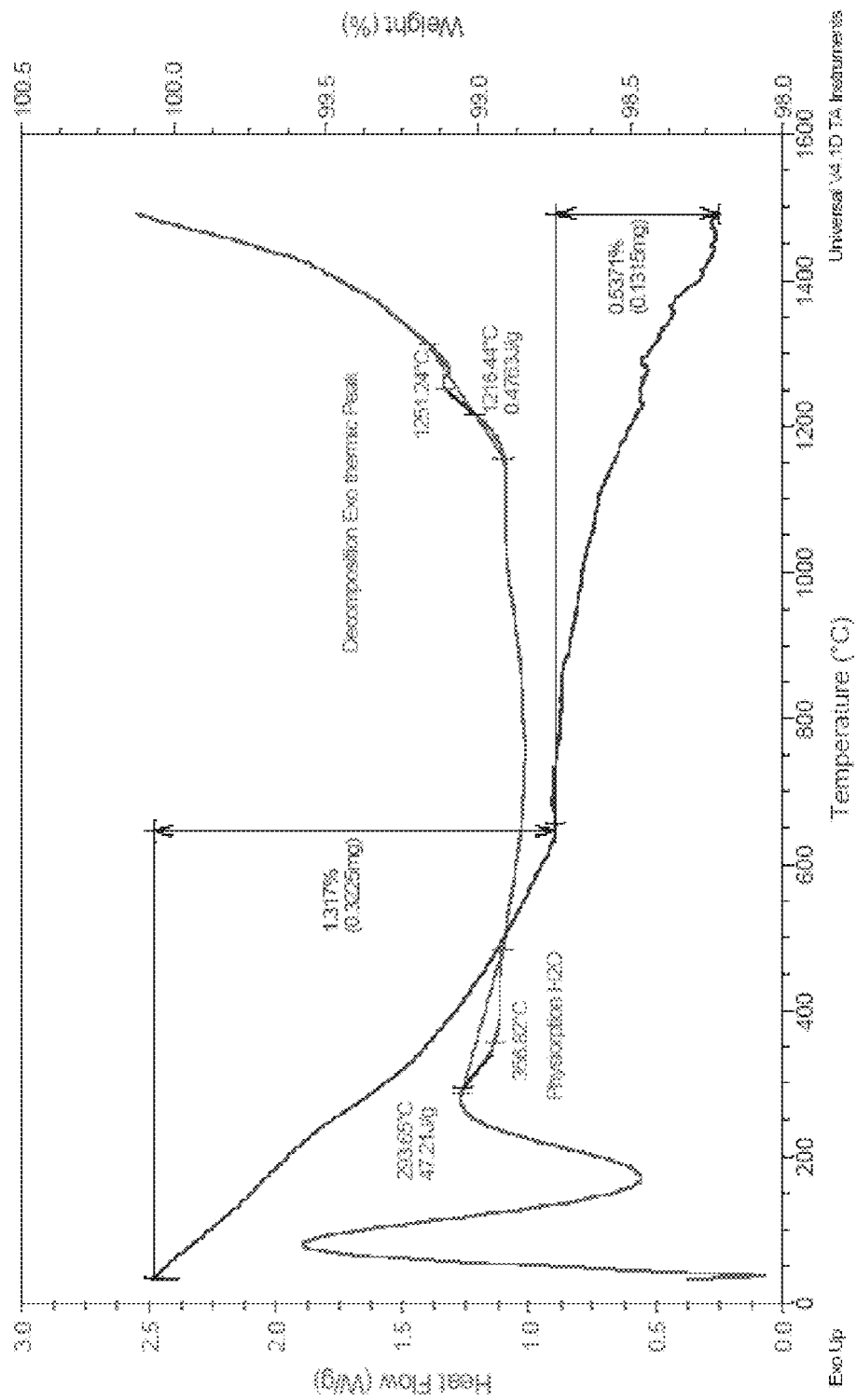
FIG. 8 is an illustration of several plots showing DSC and DTA data for select YAP formulations: (a) YAP 1 (top left), (b) YAP 5 (top right), (c) YAP 2 (bottom left), and (d) YAP 9 (bottom right).
Figure 8B:
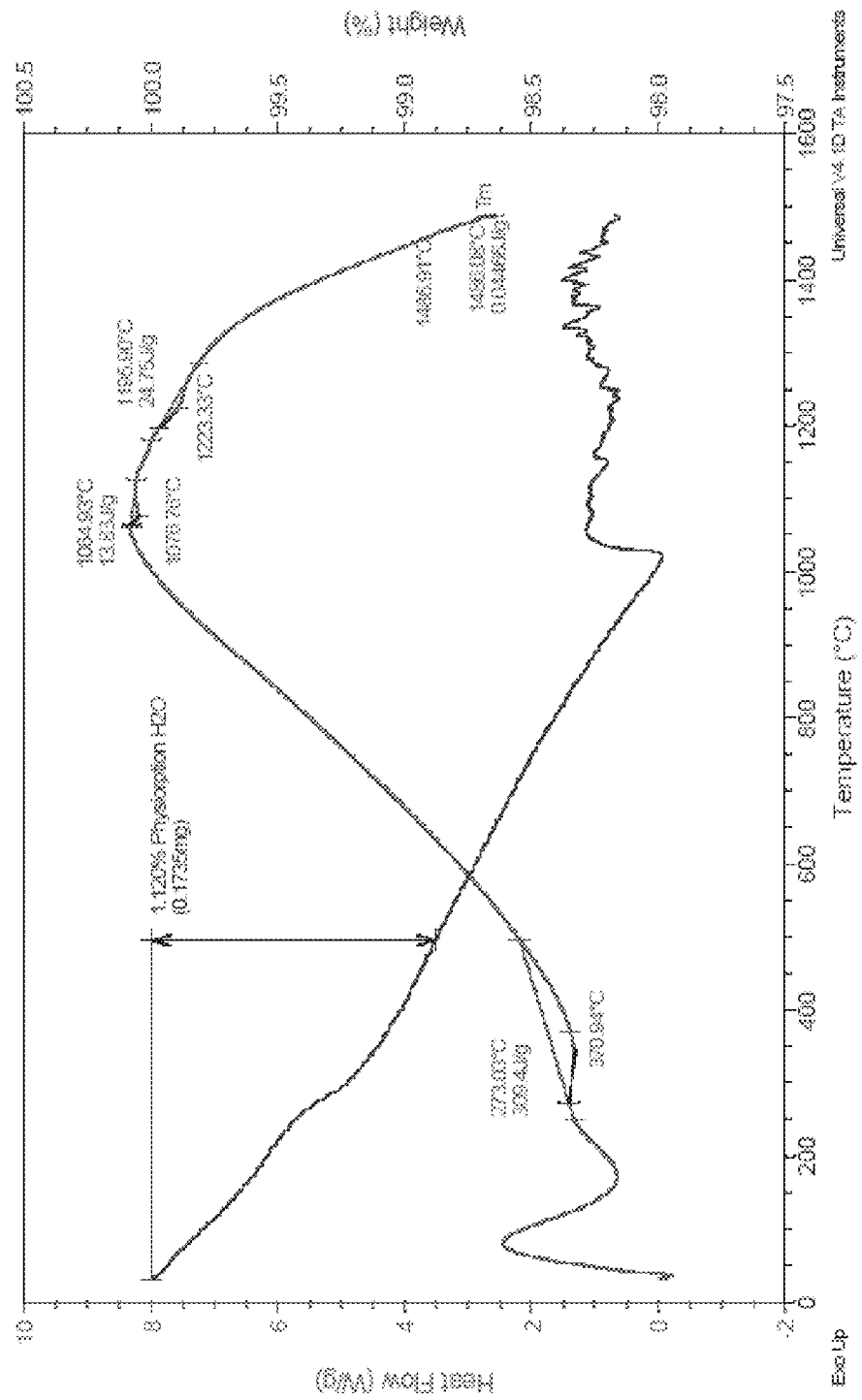
Figure 8C:
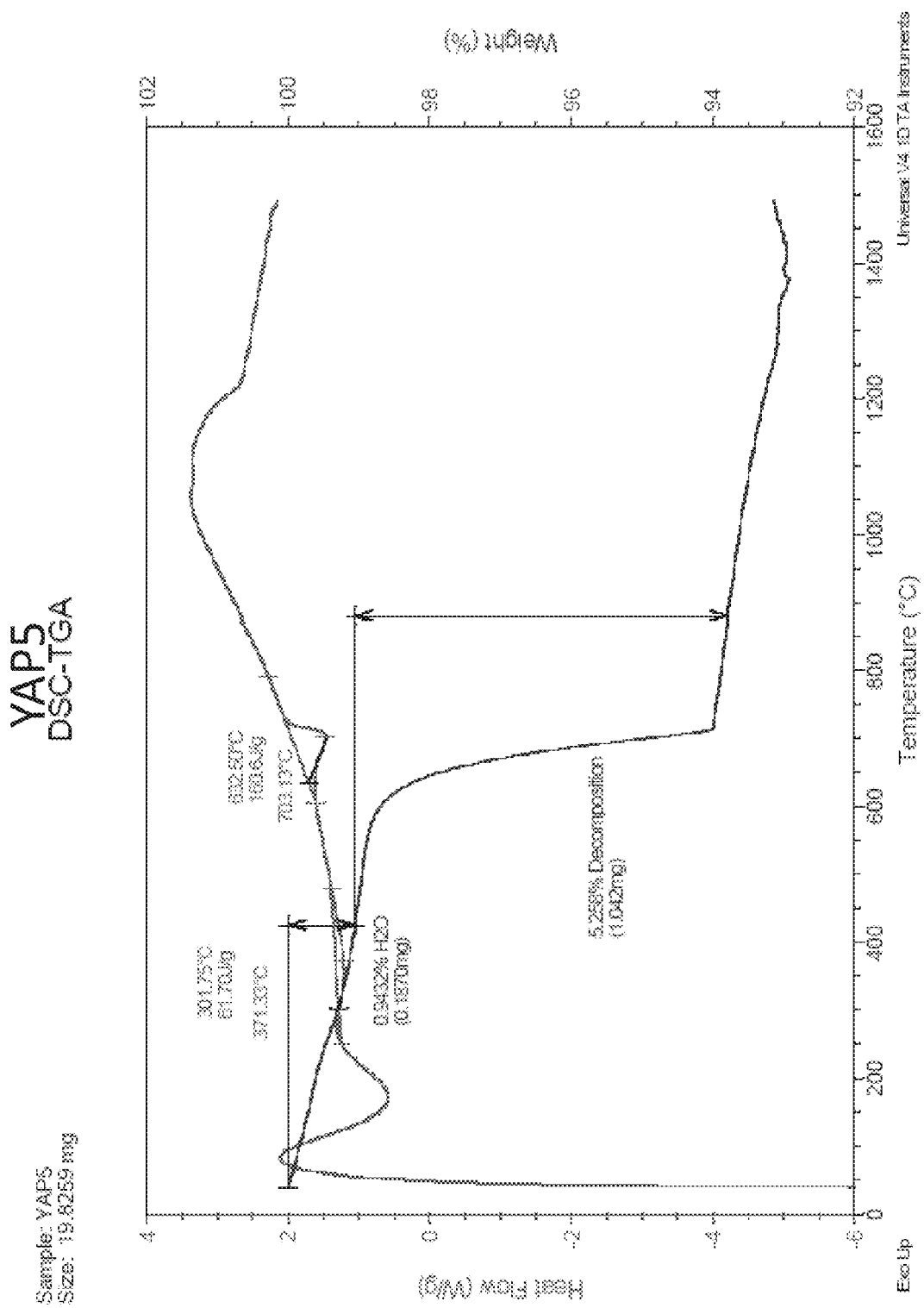
Figure 8D:
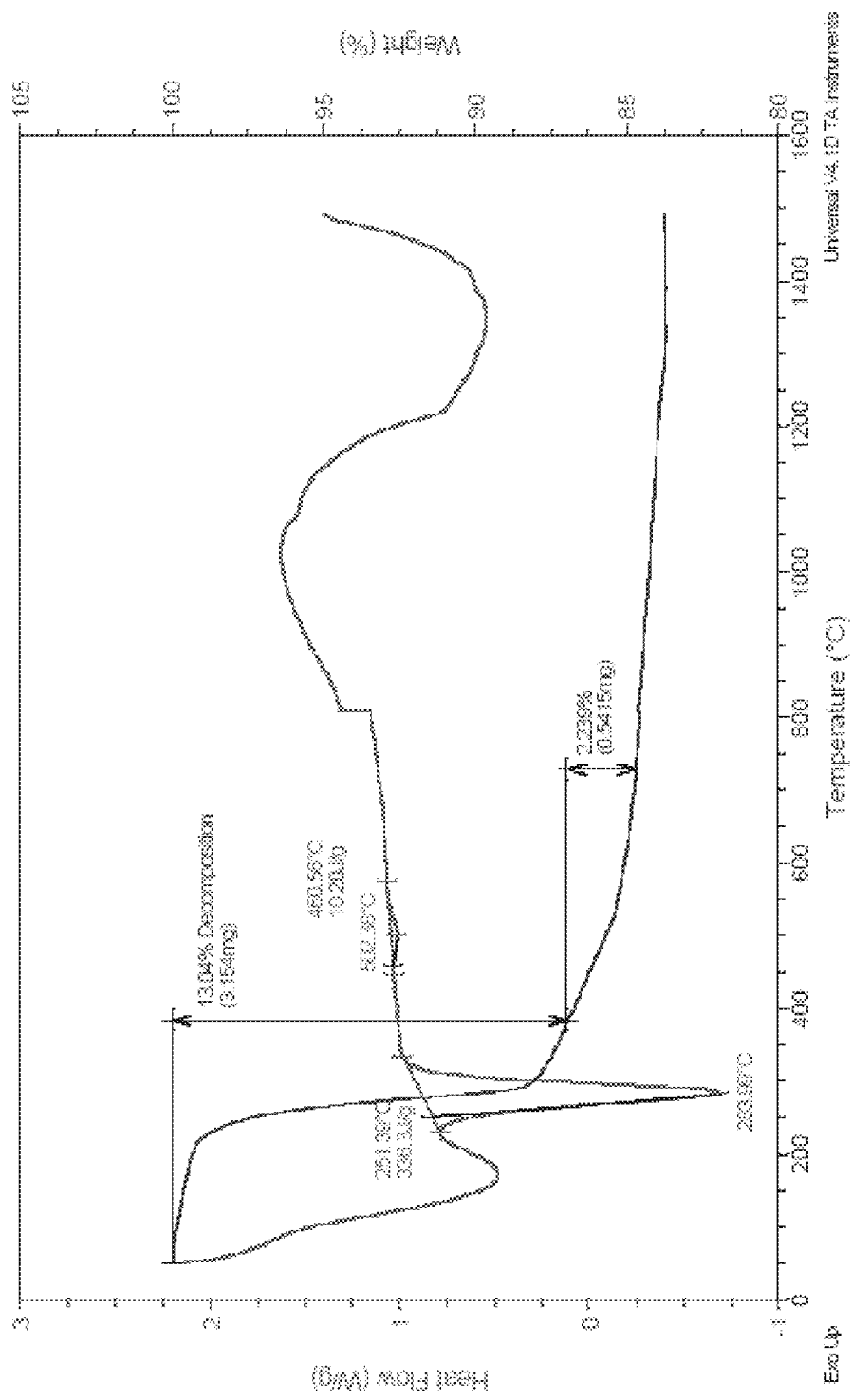

One aspect of the invention uses an up-conversion technology in coatings or surfaces. Up-conversion is the generation of a high energy wave from multiple lower energy waves. In another aspect of the invention, the coatings or surfaces include a down-conversion technology. Down-conversion is generation of a lower energy wave from a higher energy wave. Up- and down-conversion can be shown in a Jablonski energy diagram as are commonly known and available in references showing the electron states of a molecule and transitions between them. A Jablonski energy diagram also shows one aspect of the current invention where the emitted UV rays after up-conversion have a wavelength in the range of 200-450 nm, which is a range known to kill bacteria and viruses. The up-conversion material systems generally consist of three parts: an activator, a sensitizer, and a host material, however, one skilled in the art should recognize that not all three have to be present, as is the case with molecular end-chain units. The activator is typically a phosphor with many energy bands, such as the rare earth ions $Er^{+3}$ and $Tm^{+3}$, as illustrated in FIG. 2. The invention uses Rare Earth materials (such as $Yb^{+3}$) as sensitizers, which are ions that are easy to excite to a higher state, and which higher state has a long enough decay time to allow second or third stimulations to the activator emission band. Rare Earths, such as are commonly known, include at least the lanthanides together with Scandium (Sc) and Yttrium (Y). Rare earths typically comprise 15 elements with atomic numbers 57 through 71. These include at least Lanthanum (La), Cerium (Ce), Praseodymium (Pr), Neodymium (Nd), Promethium (Pm), Samarium (Sm), Europium (Eu), Gadolinium (Gd), Terbium (Tb), Dysprosium (Dy), Holmium (Ho), Erbium (Er), Thulium (Tm), Ytterbium (Yb), and Lutetium (Lu). One aspect of the invention includes using a ratio between 4 and 20 for the activator and sensitizer. Another aspect of the invention includes using a host, such as phosphate glass, soda-lime-silicate, alumina, silica, titania, or the like, which contains the activator and sensitizer and permits efficient transmission of the light source. It should be appreciated that any oxide or fluoride could be used, however. Materials for the conversion systems may use micron and submicron particles to provide an emission response from infrared radiation that would emit in the ultraviolet spectrum.

In another aspect of the current invention, rare earth (lanthanide) luminescent-doped phosphors are selected for use in the up-conversion process. Although many phosphors exist, the present invention provides for using specific rare-earth oxides in one embodiment. However, any rare earth containing powder/particulate could be used, including, but not limited to, rare earth doped fluorides. The material systems used in various embodiments of the present invention are shown, but not limited to, the materials listed in Tables 1-3.

TABLE 1

Various up-conversion powder formulations and heat treatment (HT) conditions.

| Run # | YAP # | Coating Formulation | HT Temp (° C.) | HT Time (hr) |
|---|---|---|---|---|
| 1 | 1 | $Al_2O_3 + Y_2O_3 + 3$ mol % $CeO_2$ (not pressed) | 1450 | 4.75 |
| 2 | 2 | YAP1:($Al_2O_3 + Y_2O_3 + 3$ mol % $CeO_2$) + 3.7 mol % $Yb_2O_3$ + 0.93 mol % $Nd_2O_3$ (not pressed) | 1450 | 4.75 |
| 3 | 3 | YAP1:($Al_2O_3 + Y_2O_3 + 3$ mol % $CeO_2$) + 3.7 mol % $Yb_2O_3$ + 0.93 mol % $Eu_2O_3$ (not pressed) | 1450 | 4.75 |
| 4 | 4 | YAP1:($Al_2O_3 + Y_2O_3 + 3$ mol % $CeO_2$) + 3.7 mol % $Yb_2O_3$ + 0.93 mol % $Gd_2O_3$ (not pressed) | 1450 | 4.75 |
| 5 | 5 | YAP1:($Al_2O_3 + Y_2O_3 + 3$ mol % $CeO_2$) + $CaCO_3$ (10 wt %) | 1450 | 6.5 |
| 6 | 6 | YAP2:(YAP1:($Al_2O_3 + Y_2O_3 + 3$ mol % $CeO_2$) + 3.7 mol % $Yb_2O_3$ + $Nd_2O_3$) + $CaCO_3$ (10 wt %) | 1450 | 6.5 |
| 7 | 7 | YAP3:(YAP1:($Al_2O_3 + Y_2O_3 + 3$ mol % $CeO_2$) + 3.7 mol % $Yb_2O_3$ + $Eu_2O_3$) + $CaCO_3$ (10 wt %) | 1450 | 6.5 |
| 8 | 8 | YAP4:(YAP1:($Al_2O_3 + Y_2O_3 + 3$ mol % $CeO_2$) + 3.7 mol % $Yb_2O_3$ + $Gd_2O_3$) + $CaCO_3$ (10 wt %) | 1450 | 6.5 |
| 9 | 9 | $Al(OH)_3 + Y_2O_3 + 3$ mol % $CeO_2$ | 1250 | 4 |
| 10 | 10 | YAP9:($Al(OH)_3 + Y_2O_3 + 3$ mol % $CeO_2$) + 3.7 mol % $Yb_2O_3$ + 0.93 mol % $Nd_2O_3$ | 1250 | 4 |
| 11 | 11 | YAP9:($Al(OH)_3 + Y_2O_3 + 3$ mol % $CeO_2$) + 3.7 mol % $Yb_2O_3$ + 0.93 mol % $Eu_2O_3$ | 1250 | 4 |
| 12 | 12 | YAP9:($Al(OH)_3 + Y_2O_3 + 3$ mol % $CeO_2$) + 3.7 mol % $Yb_2O_3$ + 0.93 mol % $Gd_2O_3$ | 1250 | 4 |
| 13 | 13 | YAP1:($Al_2O_3 + Y_2O_3 + 3$ mol % $CeO_2$) + 10 wt % $Na_2CO_3$ | 0 | 18.5 |
| 14 | 14 | 2 mol % Tm, 4 mol % Yb, 1 mol % Ce, 1 mol % Nd | — | — |
| 15 | 15 | YAP:1 mol % Ce | — | — |
| 16 | 16 | YAP:8 wt % Ce | — | — |
| 17 | 17 | YAP:8 wt % Ce, 2 wt % Yb, 0.5 wt % Eu | — | — |
| 18 | 1 | $Al_2O_3 + Y_2O_3 + 3$ mol % $CeO_2$ | 1450 | 24 |
| 19 | 2 | YAP1:($Al_2O_3 + Y_2O_3 + 3$ mol % $CeO_2$) + 3.7 mol % $Yb_2O_3$ + 0.93 mol % $Nd_2O_3$ | 1450 | 24 |
| 20 | 3 | YAP1:($Al_2O_3 + Y_2O_3 + 3$ mol % $CeO_2$) + 3.7 mol % $Yb_2O_3$ + 0.93 mol % $Eu_2O_3$ | 1450 | 24 |
| 21 | 4 | YAP1:($Al_2O_3 + Y_2O_3 + 3$ mol % $CeO_2$) + 3.7 mol % $Yb_2O_3$ + 0.93 mol % $Gd_2O_3$ | 1450 | 24 |
| 22 | 5 | YAP1:($Al_2O_3 + Y_2O_3 + 3$ mol % $CeO_2$) + $CaCO_3$ (10 wt %) | 1450 | 24 |
| 23 | 6 | YAP2:(YAP1:($Al_2O_3 + Y_2O_3 + 3$ mol % $CeO_2$) + 3.7 mol % $Yb_2O_3$ + $Nd_2O_3$) + $CaCO_3$ (10 wt %) | 1450 | 24 |
| 24 | 7 | YAP3:(YAP1:($Al_2O_3 + Y_2O_3 + 3$ mol % $CeO_2$) + 3.7 mol % $Yb_2O_3$ + $Eu_2O_3$) + $CaCO_3$ (10 wt %) | 1450 | 24 |
| 25 | 8 | YAP4:(YAP1:($Al_2O_3 + Y_2O_3 + 3$ mol % $CeO_2$) + 3.7 mol % $Yb_2O_3$ + $Gd_2O_3$) + $CaCO_3$ (10 wt %) | 1450 | 24 |
| 26 | 9 | $Al(OH)_3 + Y_2O_3 + 3$ mol % $CeO_2$ | — | — |
| 27 | 10 | YAP9:($Al(OH)_3 + Y_2O_3 + 3$ mol % $CeO_2$) + 3.7 mol % $Yb_2O_3$ + 0.93 mol % $Nd_2O_3$ | — | — |
| 28 | 11 | YAP9:($Al(OH)_3 + Y_2O_3 + 3$ mol % $CeO_2$) + 3.7 mol % $Yb_2O_3$ + 0.93 mol % $Eu_2O_3$ | — | — |
| 29 | 12 | YAP9:($Al(OH)_3 + Y_2O_3 + 3$ mol % $CeO_2$) + 3.7 mol % $Yb_2O_3$ + 0.93 mol % $Gd_2O_3$ | — | — |
| 30 | 1 | $Al_2O_3 + Y_2O3 + 3$ mol % $CeO_2$ | — | — |
| 31 | 2 | YAP1:($Al_2O_3 + Y_2O_3 + 3$ mol % $CeO_2$) + 3.7 mol % $Yb_2O_3$ + 0.93 mol % $Nd_2O_3$ | — | — |
| 32 | 3 | YAP1:($Al_2O_3 + Y_2O_3 + 3$ mol % $CeO_2$) + 3.7 mol % $Yb_2O_3$ + 0.93 mol % $Eu_2O_3$ | — | — |
| 33 | 4 | YAP1:($Al_2O_3 + Y_2O_3 + 3$ mol % $CeO_2$) + 3.7 mol % $Yb_2O_3$ + 0.93 mol % $Gd_2O_3$ | — | — |
| 34 | 5 | YAP1:($Al_2O_3 + Y_2O_3 + 3$ mol % $CeO_2$) + $CaCO_3$ (10 wt %) | — | — |
| 35 | 6 | YAP2:(YAP1:($Al_2O_3 + Y_2O_3 + 3$ mol % $CeO_2$) + 3.7 mol % $Yb_2O_3$ + $Nd_2O_3$) + $CaCO_3$ (10 wt %) | — | — |
| 36 | 7 | YAP3:(YAP1:($Al_2O_3 + Y_2O_3 + 3$ mol % $CeO_2$) + 3.7 mol % $Yb_2O_3$ + $Eu_2O_3$) + $CaCO_3$ (10 wt %) | — | — |
| 37 | 8 | YAP4:(YAP1:($Al_2O_3 + Y_2O_3 + 3$ mol % $CeO_2$) + 3.7 mol % $Yb_2O_3$ + $Gd_2O_3$) + $CaCO_3$ (10 wt %) | — | — |
| 38 | 9 | $Al(OH)_3 + Y_2O_3 + 3$ mol % $CeO_2$ | 1450 | 7 |
| 39 | 10 | YAP9:($Al(OH)_3 + Y_2O_3 + 3$ mol % $CeO_2$) + 3.7 mol % $Yb_2O_3$ + 0.93 mol % $Nd_2O_3$ | 1450 | 7 |
| 40 | 11 | YAP9:($Al(OH)_3 + Y_2O_3 + 3$ mol % $CeO_2$) + 3.7 mol % $Yb2O3$ + 0.93 mol % $Eu_2O_3$ | 1450 | 7 |
| 41 | 12 | YAP9:($Al(OH)_3 + Y_2O_3 + 3$ mol % $CeO_2$) + 3.7 mol % $Yb_2O_3$ + 0.93 mol % $Gd_2O_3$ | 1450 | 7 |

TABLE 1-continued

Various up-conversion powder formulations and heat treatment (HT) conditions.

| Run # | YAP # | Coating Formulation | HT Temp (° C.) | HT Time (hr) |
|---|---|---|---|---|
| 42 | 1 | Al2O3 + Y2O3 + 3 mol % CeO2 | — | — |
| 43 | 2 | YAP1:(Al2O3 + Y2O3 + 3 mol % CeO2) + 3.7 mol % Yb2O3 + 0.93 mol % Nd2O3 | — | — |
| 44 | 3 | YAP1:(Al2O3 + Y2O3 + 3 mol % CeO2) + 3.7 mol % Yb2O3 + 0.93 mol % Eu2O3 | — | — |
| 45 | 4 | YAP1:(Al2O3 + Y2O3 + 3 mol % CeO2) + 3.7 mol % Yb2O3 + 0.93 mol % Gd2O3 | — | — |
| 46 | 5 | YAP1:(Al2O3 + Y2O3 + 3 mol % CeO2) + CaCO3(10 wt %) | — | — |
| 47 | 6 | YAP2:(YAP1:(Al2O3 + Y2O3 + 3 mol % CeO2) + 3.7 mol % Yb2O3 + Nd2O3) + CaCO3(10 wt %) | — | — |
| 48 | 7 | YAP3:(YAP1:(Al2O3 + Y2O3 + 3 mol % CeO2) + 3.7 mol % Yb2O3 + Eu2O3) + CaCO3(10 wt %) | — | — |
| 49 | 8 | YAP4:(YAP1:(Al2O3 + Y2O3 + 3 mol % CeO2) + 3.7 mol % Yb2O3 + Gd2O3) + CaCO3(10 wt %) | — | — |
| 50 | 9 | Al(OH)3 + Y2O3 + 3 mol % CeO2 | 1450 | 24.5 |
| 51 | 10 | YAP9:(Al(OH)3 + Y2O3 + 3 mol % CeO2) + 3.7 mol % Yb2O3 + 0.93 mol % Nd2O3 | 1450 | 24.5 |
| 52 | 11 | YAP9:(Al(OH)3 + Y2O3 + 3 mol % CeO2) + 3.7 mol % Yb2O3 + 0.93 mol % Eu2O3 | 1450 | 24.5 |
| 53 | 12 | YAP9:(Al(OH)3 + Y2O3 + 3 mol % CeO2) + 3.7 mol % Yb2O3 + 0.93 mol % Gd2O3 | 1450 | 24.5 |
| 54 | 1 | Al2O3 + Y2O3 + 3 mol % CeO2 | — | — |
| 55 | 2 | YAP1:(Al2O3 + Y2O3 + 3 mol % CeO2) + 3.7 mol % Yb2O3 + 0.93 mol % Nd2O3 | 1450 | 48 |
| 56 | 3 | YAP1:(Al2O3 + Y2O3 + 3 mol % CeO2) + 3.7 mol % Yb2O3 + 0.93 mol % Eu2O3 | 1450 | 48 |
| 57 | 4 | YAP1:(Al2O3 + Y2O3 + 3 mol % CeO2) + 3.7 mol % Yb2O3 + 0.93 mol % Gd2O3 | 1450 | 48 |
| 58 | 5 | YAP1:(Al2O3 + Y2O3 + 3 mol % CeO2) + CaCO3(10 wt %) | 1450 | 48 |
| 59 | 6 | YAP2:(YAP1:(Al2O3 + Y2O3 + 3 mol % CeO2) + 3.7 mol % Yb2O3 + Nd2O3) + CaCO3(10 wt %) | 1450 | 48 |
| 60 | 7 | YAP3:(YAP1:(Al2O3 + Y2O3 + 3 mol % CeO2) + 3.7 mol % Yb2O3 + Eu2O3) + CaCO3(10 wt %) | 1450 | 48 |
| 61 | 8 | YAP4:(YAP1:(Al2O3 + Y2O3 + 3 mol % CeO2) + 3.7 mol % Yb2O3 + Gd2O3) + CaCO3(10 wt %) | 1450 | 48 |
| 62 | 9 | Al(OH)3 + Y2O3 + 3 mol % CeO2 | 1450 | 48 |
| 63 | 10 | YAP9:(Al(OH)3 + Y2O3 + 3 mol % CeO2) + 3.7 mol % Yb2O3 + 0.93 mol % Nd2O3 | 1450 | 48 |
| 64 | 11 | YAP9:(Al(OH)3 + Y2O3 + 3 mol % CeO2) + 3.7 mol % Yb2O3 + 0.93 mol % Eu2O3 | 1450 | 48 |
| 65 | 12 | YAP9:(Al(OH)3 + Y2O3 + 3 mol % CeO2) + 3.7 mol % Yb2O3 + 0.93 mol % Gd2O3 | 1450 | 48 |

TABLE 2

Various up-conversion powder formulations.

| YAP # | Mol % Al2O3 | Mol % Y2O3 | Mol % ZrO2 | Mol % Yb2O3 | Mol % Eu2O3 | Mol % Er2O3 | Mol % CeO2 | Ratio of Yb:Eu, Er | Total Mol % of Dopant (oxide) |
|---|---|---|---|---|---|---|---|---|---|
| YAP-G1 | 47.40 | 47.75 | 0.00 | 4.43 | 0.00 | 0.42 | 0.00 | 10-to-1 | 4.85 mol % |
| YAP-G2 | 48.18 | 48.38 | 0.00 | 1.69 | 0.00 | 1.75 | 0.00 | 1-to-1 | 3.44 mol % |
| YAP-G3 | 48.57 | 49.11 | 0.00 | 1.95 | 0.00 | 0.37 | 0.00 | 5-to-1 | 2.32 mol % |
| YAP-G4 | 48.97 | 48.98 | 0.00 | 1.85 | 0.20 | 0.00 | 0.00 | 10-to-1 | 2 mol % |
| YAP-G5 | 45.00 | 45.00 | 0.00 | 9.09 | 0.91 | 0.00 | 0.00 | 10-to-1 | 10 mol % |
| YAP-G6 | 49.55 | 49.44 | 0.00 | 0.91 | 0.09 | 0.00 | 0.00 | 10-to-1 | 1 mol % |
| YAP-G7 | 48.99 | 49.01 | 0.00 | 1.00 | 1.00 | 0.00 | 0.00 | 1-to-1 (failed) | 2 mol % (failed) |
| YAP-G8 | 48.92 | 48.94 | 0.00 | 1.10 | 1.05 | 0.00 | 0.00 | 1-to-1 | 2 mol % |
| YAP-G9 | 49.01 | 48.99 | 0.00 | 1.67 | 0.34 | 0.00 | 0.00 | 5-to-1 | 2 mol % |
| YAP-G10 | 47.48 | 47.52 | 0.00 | 4.55 | 0.45 | 0.00 | 0.00 | 10-to-1 | 5 mol % |
| YAP-G11 | 48.98 | 49.02 | 0.00 | 1.82 | 0.18 | 0.00 | 0.00 | 10-to-1 | 2 mol % |
| YAP-G12 | 48.50 | 48.50 | 0.00 | 1.00 | 1.00 | 0.00 | 1.00 | 1-to-1 | 3 mol % |
| ZrO2-G1 | 0.00 | 0.00 | 90.00 | 9.09 | 0.91 | 0.00 | 0.00 | 10-to-1 | 10 mol % |
| ZrO2-G2 | 0.00 | 0.00 | 90.00 | 8.34 | 1.67 | 0.00 | 0.00 | 5-to-1 | 10 mol % |
| ZrO2-G3 | 0.00 | 0.00 | 95.00 | 4.17 | 0.83 | 0.00 | 0.00 | 5-to-1 | 5 mol % |
| ZrO2-G4 | 0.00 | 0.00 | 99.00 | 0.83 | 0.17 | 0.00 | 0.00 | 5-to-1 | 1 mol % |

TABLE 2-continued

Various up-conversion powder formulations.

| YAP # | Mol % Al2O3 | Mol % Y2O3 | Mol % ZrO2 | Mol % Yb2O3 | Mol % Eu2O3 | Mol % Er2O3 | Mol % CeO2 | Ratio of Yb:Eu, Er | Total Mol % of Dopant (oxide) |
|---|---|---|---|---|---|---|---|---|---|
| ZrO2-G5 | 0.00 | 0.00 | 90.00 | 5.00 | 5.00 | 0.00 | 0.00 | 1-to-1 | 10 mol % |
| ZrO2-G6 | 0.00 | 0.00 | 90.00 | 0.00 | 8.34 | 0.00 | 0.00 | 1-to-5 | 10 mol % |

TABLE 3

Various up-conversion powder formulations.

| Formulation | Mol % Lu2O3 | Mol % Al2O3 | Mol % CeO2 | Calcination Time | Calcination Temperature | Milling Time |
|---|---|---|---|---|---|---|
| LuAG-1 | 37.50 | 62.50 | 0.00 | 10 hours | 1400 C. | 24 hrs |
| LuAG-2 | 37.12 | 61.88 | 1.00 | 10 hours | 1400 C. | 24 hrs |
| LuAG-S | 36.50 | 62.50 | 1.00 | 2 hours | 1200 C. | 24 hrs |
| LuAG-3 | 37.10 | 61.85 | 1.05 | 2 hours | 1200 C. | 48 hrs |
| LuAG-4A | 37.11 | 61.85 | 1.03 | 2 hours | 1200 C. | 24 hrs |
| LuAG-4B | 37.11 | 61.85 | 1.03 | 10 hours | 1400 C. | 24 hrs |
| LuAG-4C1 | 37.11 | 61.85 | 1.03 | 13+ hours | ~1415 C. | 24 hrs |
| LuAG-4C2 | 37.11 | 61.85 | 1.03 | 13+ hours | ~1415 | 24 hrs |

In one embodiment of the invention, a slurry method is used to synthesize rare earth doped YAP (Yttrium Aluminum Perovskite), LuAG (Lutetium Aluminum Garnet), and YAG (Yttrium Aluminum Garnet) materials. The starting formulations should be weighed to the desired amounts and batch lots processed in either half pound or pound batches. This method allows for the addition of surfactants to be included during the synthesis of the powder. Further steps of the slurry method include, but are not limited to, the following processes:

1. The raw materials are mixed together and then ball milled for 24 hours in approximately 450 mL of ethanol in an HDPE bottle using zirconia milling media. The ratio of media to powder formulation is 9:1;
2. The YAP slurry is then heated on a hot plate at 175-200° C. until all the ethanol is evaporated off;
3. The powder is then ground using a mortar and pestle;
4. The dried powder is then calcined in an alumina crucible for 2 hours at elevated temperature (1200° C.);
5. The calcined powder is then ball milled again for 24 hours in approximately 450 mL of ethanol in an HDPE bottle using yttria partially stabilized zirconia media (9:1 ratio);
6. The YAP slurry is then heated on a hot plate at 175-200° C. until the ethanol is evaporated.

Another process to synthesize re-doped YAP provides for using $Al_2O_3$ as starting material. $Al_2O_3$, $Y_2O_3$, and $CeO_2$ are mixed together in desired concentrations and then calcined at different times and temperatures, followed by mechanical milling. In one aspect, 30.58 g Al2O3, 67.75 g Y2O3 and 3.04 g CeO2 (3 mol %) are mixed together using a clean spatula (YAP1). For bulk processing of different dopant concentrations, YAP1 formulation is divided into the desired number of batches. For most of these trials, the powder lots are divided into 4 batches, with each batch approximately 25.34 g. For YAP2: 2.2 g Yb2O3 (3.7 mol %) and 0.47 g Nd2O3 (0.93 mol %) are mixed to YAP1. For YAP3: 2.2 g Yb2O3 (3.7 mol %) and 0.5 g Eu2O3 (0.93 mol %) are mixed to YAP1. For YAP4: 2.2 g Yb2O3 (3.72 mol %) and 0.51 g Gd2O3 (0.93 mol %) are mixed to YAP1. Three different furnace treatments are explored:

a. Powders are placed into crucibles in an air furnace and are heat treated at 1450° C. for 4.75 hours.
b. Powders are pressed into pellets and are heated up to 1450° C. for 24 hours.
c. Add 10 wt % CaCO3 to each batch (YAP 5, 6, 7, 8) to lower the calcination temperature. The powders are pressed and then at least two pellets from each batch are heated to 1450° C. for 24 hours.

Another process for synthesizing re-doped YAP provides for using $AL(OH)_3$ as the starting material. The process involves the same steps as when using $Al_2O_3$ as the starting material. 100 g Al(OH)3 and 144.74 g Y2O3 (Y:Al=1:1) concentrations are mixed together as the starting materials. The mixed formulation is then combined with yttria partially stabilized zirconia grinding media (839.15 g) in a container and ball milled (commination) for 18 hours. After ball milling, the powders are transferred to a clean beaker. The typical total powder weight after ball-milling was 238.00 g. The batch lot is then divided into four amounts, each weighing approximately 59.5 g.

a. Add 1.26 g CeO2 (3 mol %) to batch one—YAP 9.
b. Add 1.26 g CeO2, 3.54 g Yb2O3 (3.7 mol %), and 0.76 g Nd2O3 (0.93 mol %) to batch 2—YAP 10.
c. Add 1.26 g CeO2, 3.54 g Yb2O3 (3.7 mol %), and 0.80 g Eu2O3 (0.93 mol %) to batch 3—YAP 11.
d. Add 1.26 g CeO2, 3.54 g Yb2O3 (3.7 mol %), and 0.82 g Gd2O3 (0.93 mol %) to batch 4—YAP 12.

The formulations are again mechanically mixed and comminuted using the ball milling methods previously described. Using a Carver Press, the powders are pressed into pellets for subsequent heat treatments, sintering, and electron beam melting trials. The various pellets are then placed into an alumina crucible and then heat treated at 1250° C. or 1450° C. for 4 hours before being allowed to air cool to room temperature.

It should be appreciated by those skilled in the art that several processes can be used to synthesize the up-conversion materials. Examples of other processes include, but are not limited to, sintering, hot pressing, melting, chemical methods, and vapor methods.

Differential Scanning calorimetry (DSC) studies can be performed to determine the various phase transitions and melting behaviors of the RE-doped YAP candidate material systems with the different powder formulations. The results of the studies for YAP1, YAP2, YAP5, and YAP 9 are shown in FIG. 8.

Figure 9:
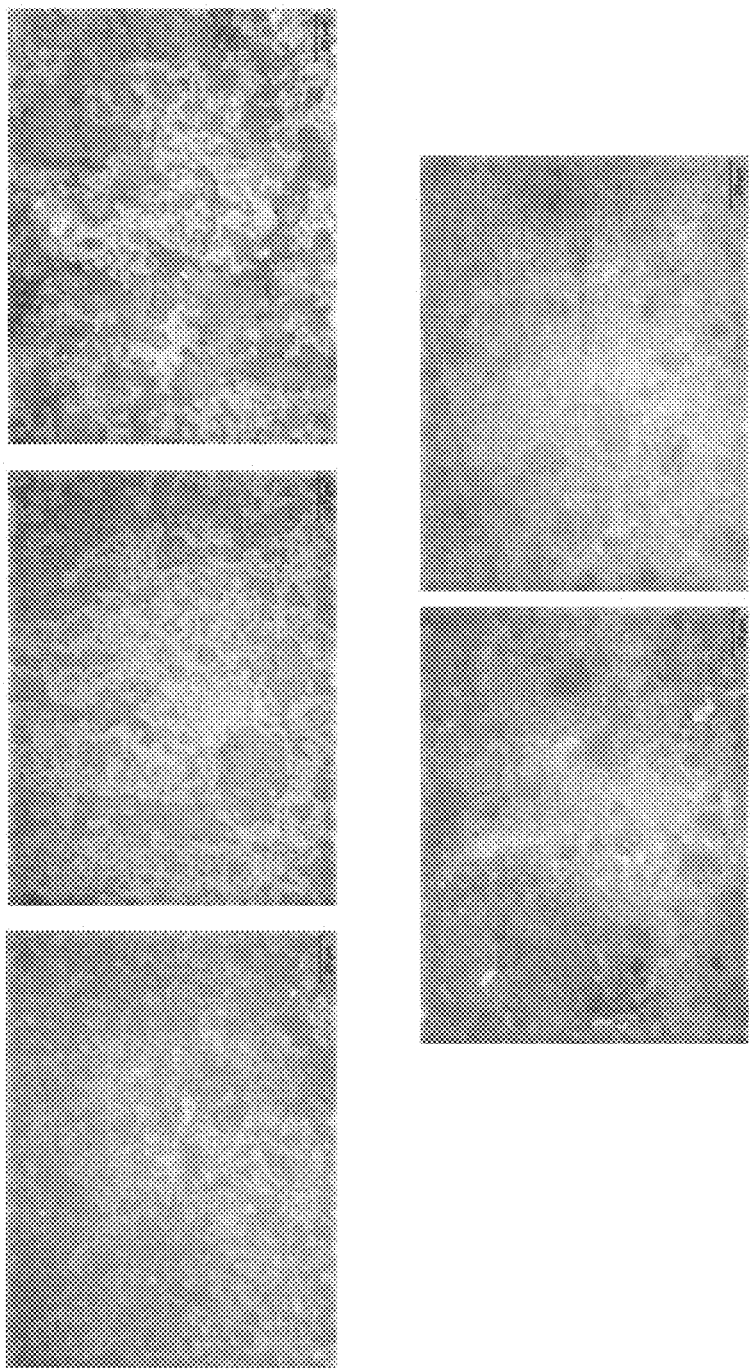
FIG. 9 illustrates photos of optical micrographs of various YAP-based formulations under various heat conditions.

Selected sintered pellets may be examined using light microscopy to determine the effects of heat treating the powders at elevated time and temperature. The heat treated pellets are sectioned and placed into 1-inch diameter cold epoxy mounts. The samples are then ground using a semi-automatic grinding polishing unit using 240, 320, 400, 600, 800, 1000, grit silicon carbide paper, while rinsing with deionized water and drying with compressed nitrogen between steps. Once the grinding is complete, the samples are polished using 3 μm and 1 μm diamond suspension for 5-10 minutes to ensure a good quality surface finish. FIG. 9 shows polished cross sections of YAP-based heat treated pellets under various heat conditions as follows: (a) YAP 3 at 1450° C. for 24 hrs (top left), (b) YAP 5 at 1450° C. for 24 hrs (top middle), (c) YAP 9 at 1250° C. for 4 hrs (top right), (d) YAP 10 at 1450° C. for 7 hrs (bottom left), and (e) YAP11 at 1250° C. for 4 hrs (bottom right). Particle sintering is observable in the micrographs, but there is no evidence of melting.

Figure 10A:
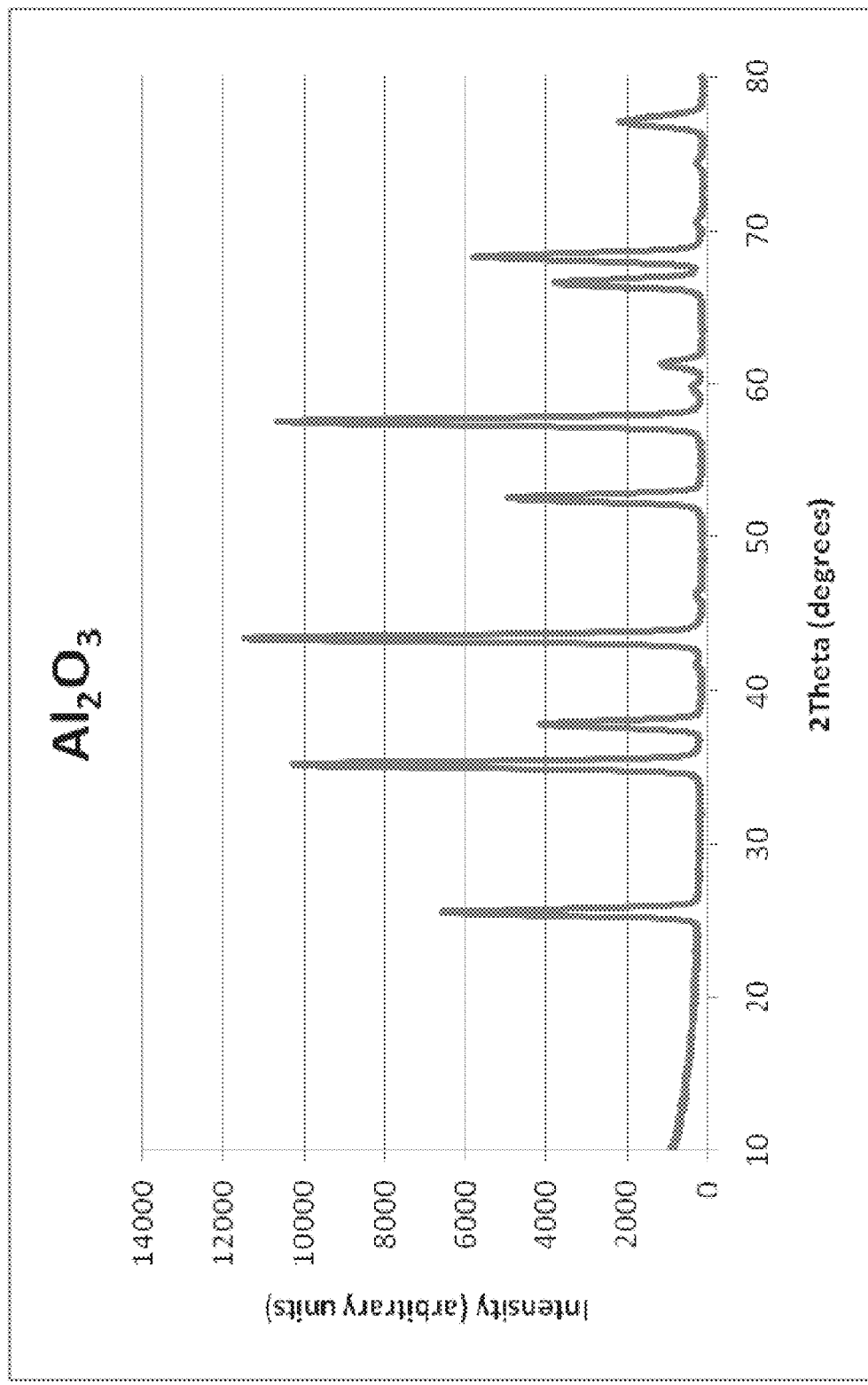
FIG. 10($a$) is a graph of x-ray diffraction data for Al$_2$O$_3$ showing the hexagonal, alpha aluminum oxide phase.
Figure 10B:
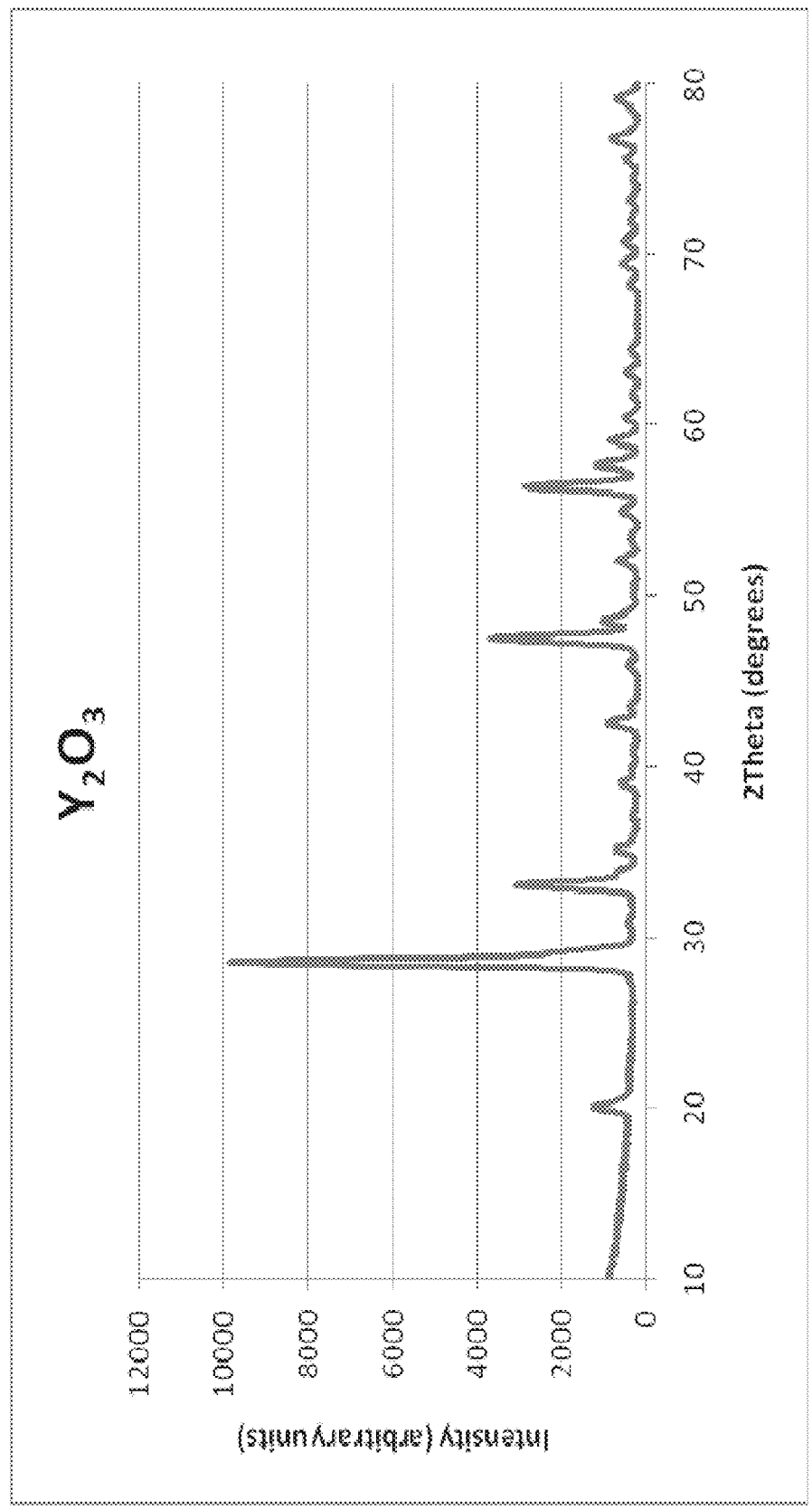
Figure 10C:
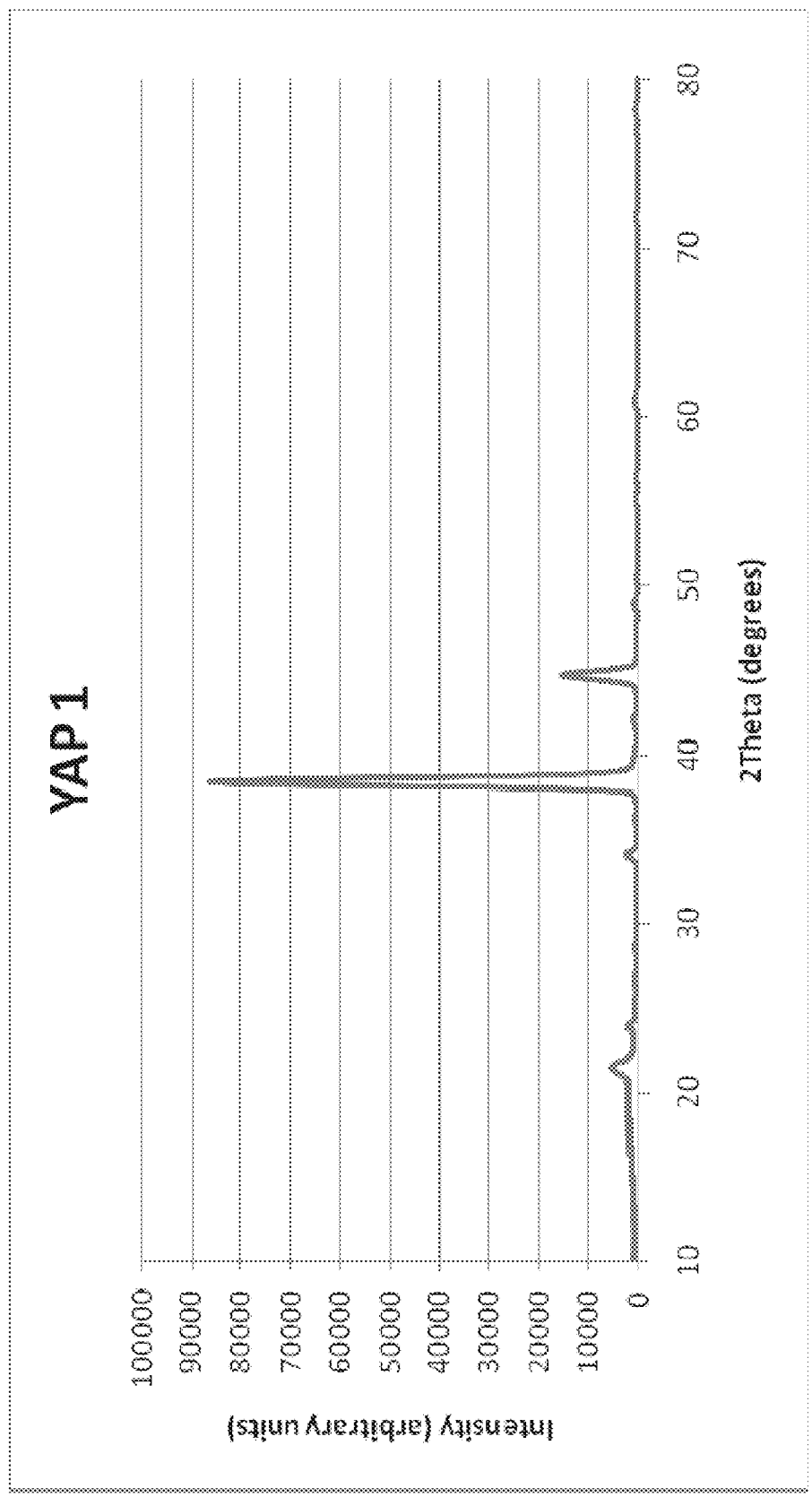
Figure 10D:
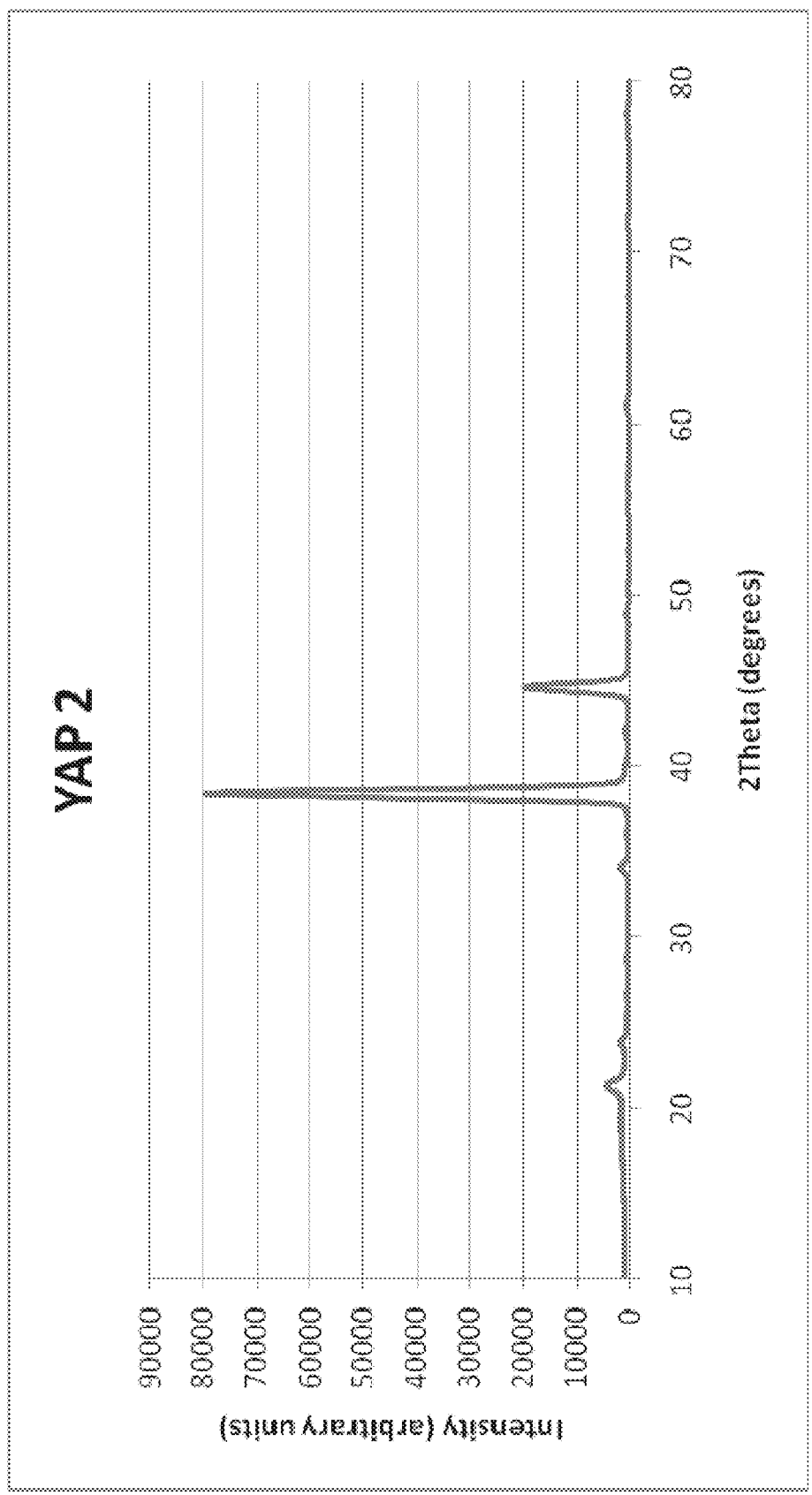
Figure 10E:
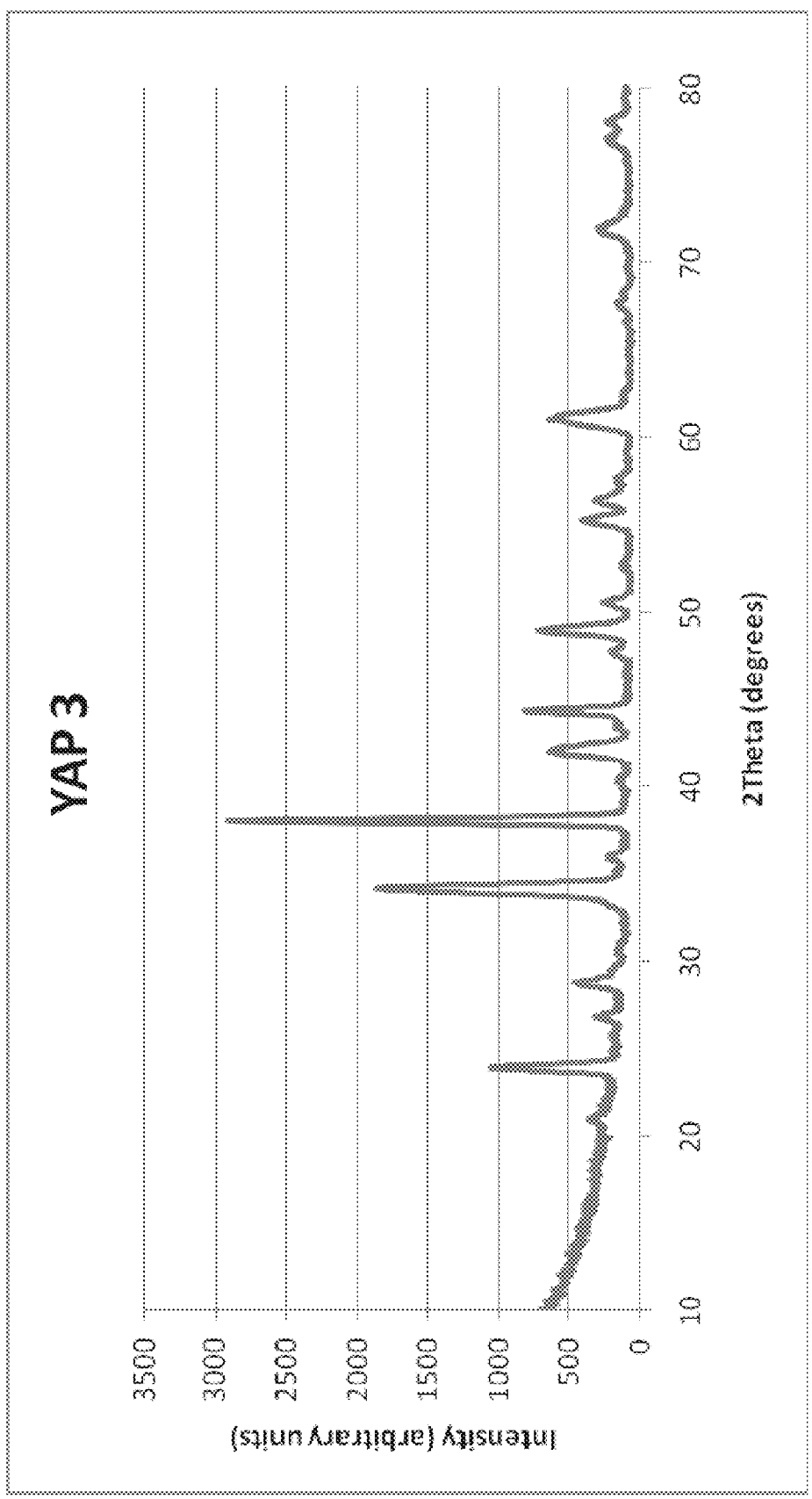
Figure 10F:
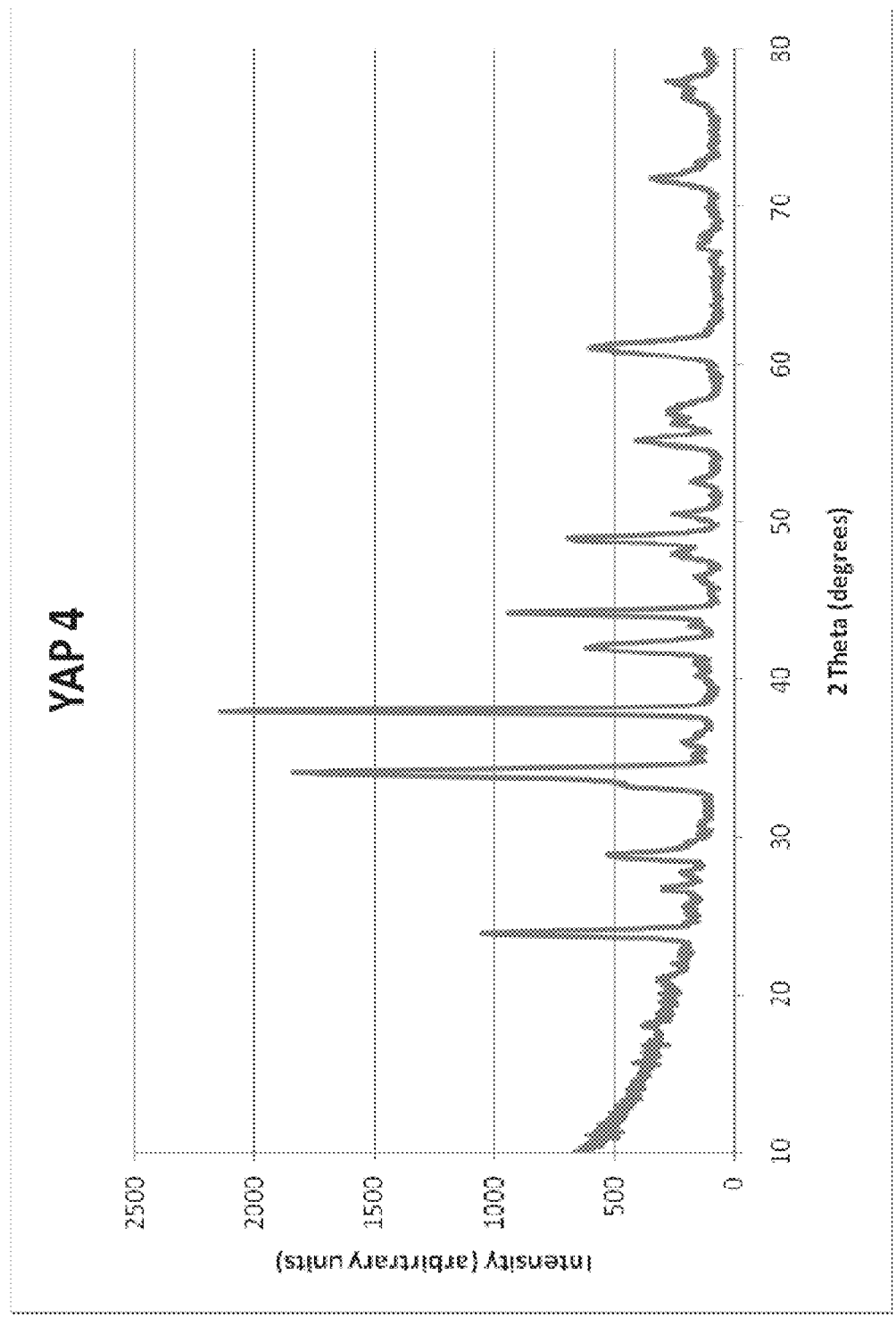
Figure 10G:
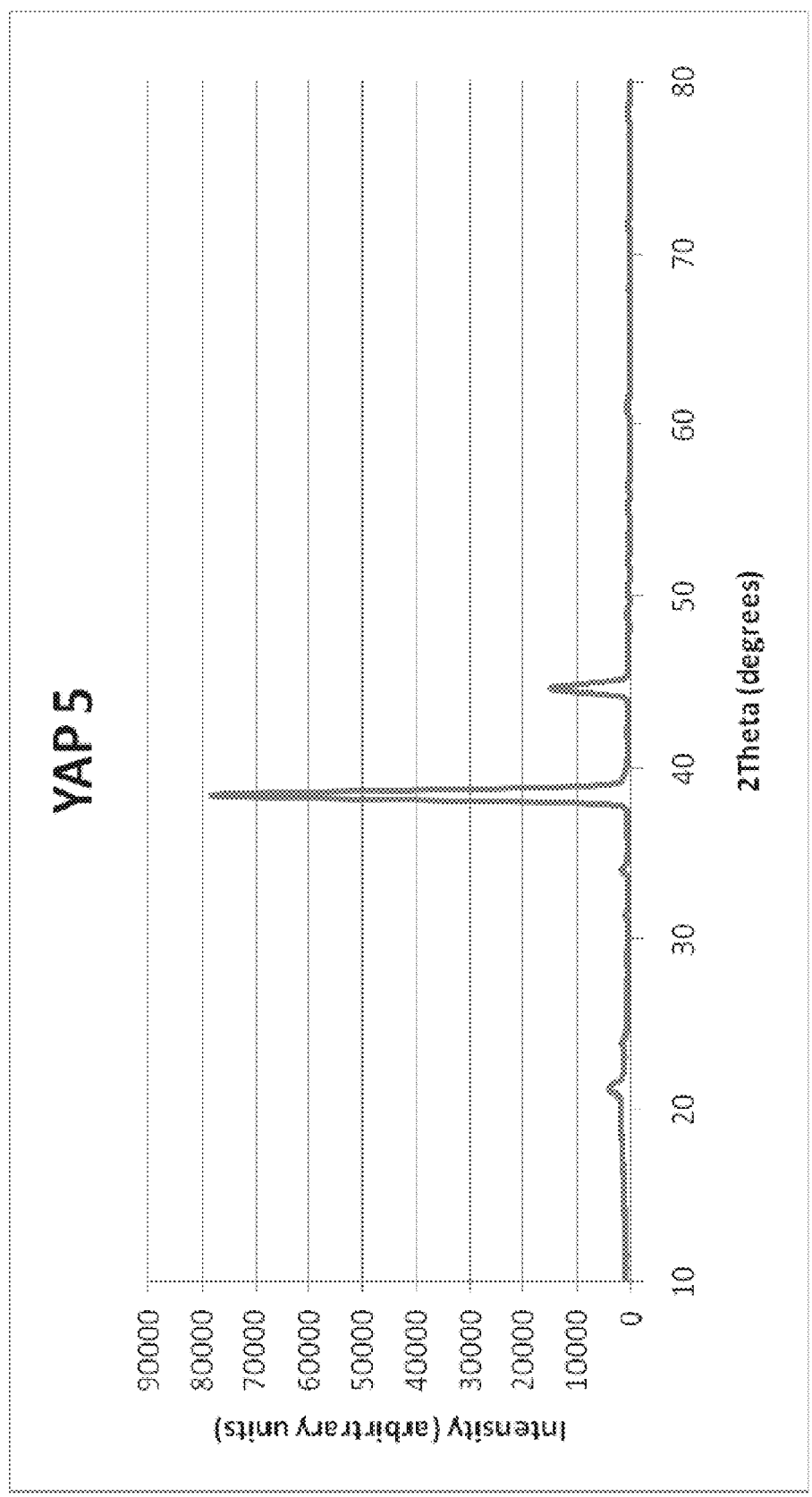
Figure 10H:
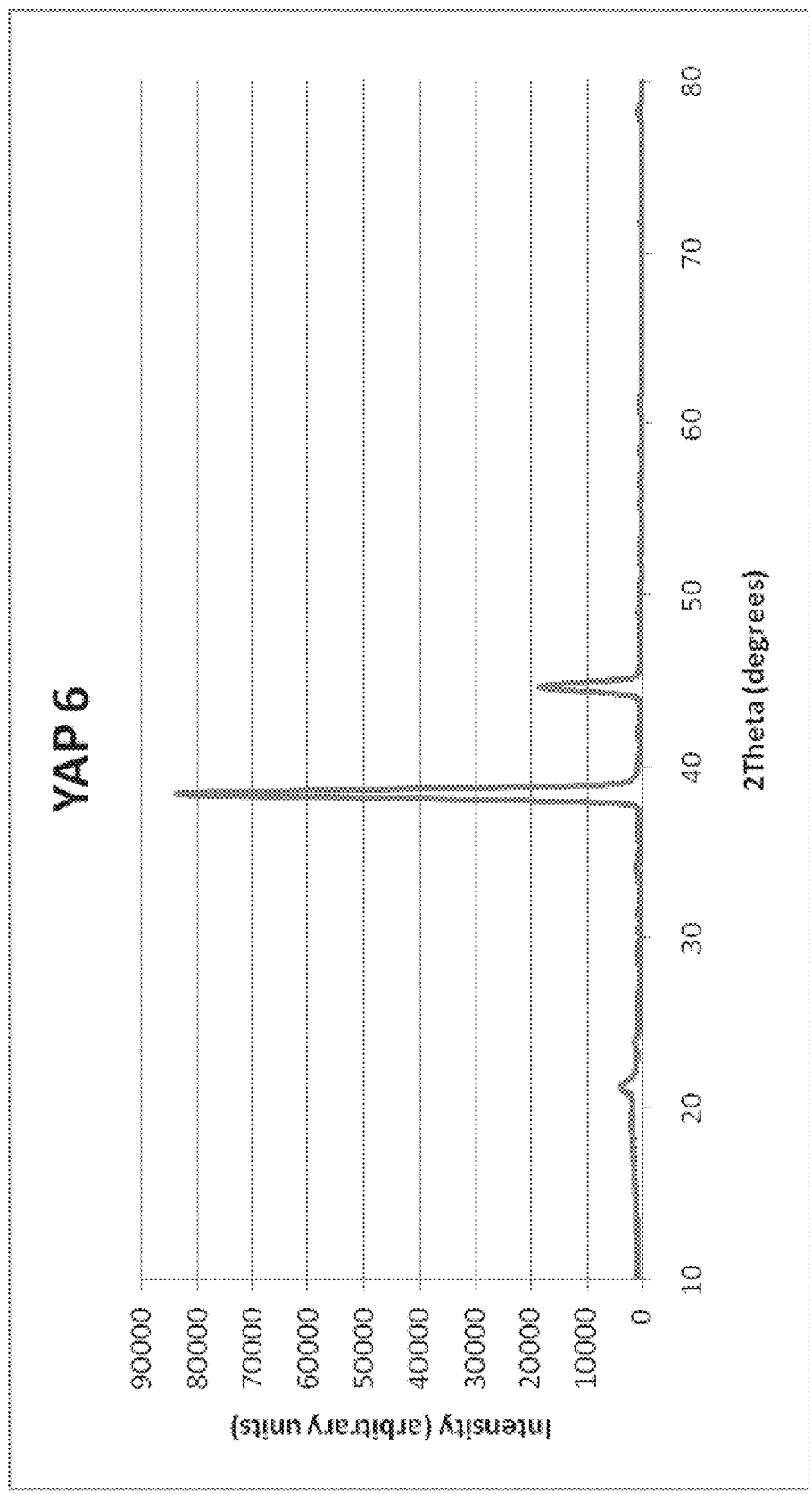
Figure 10I:
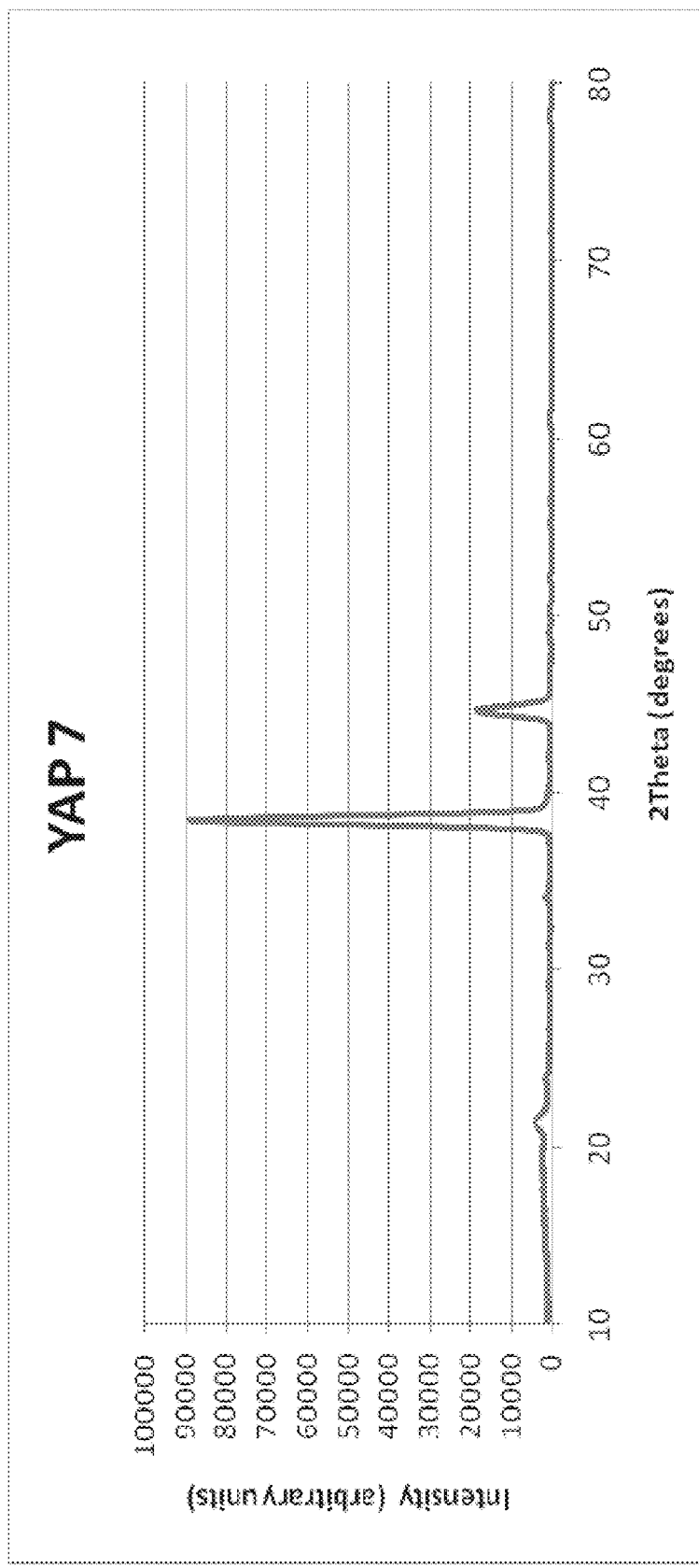
Figure 10J:
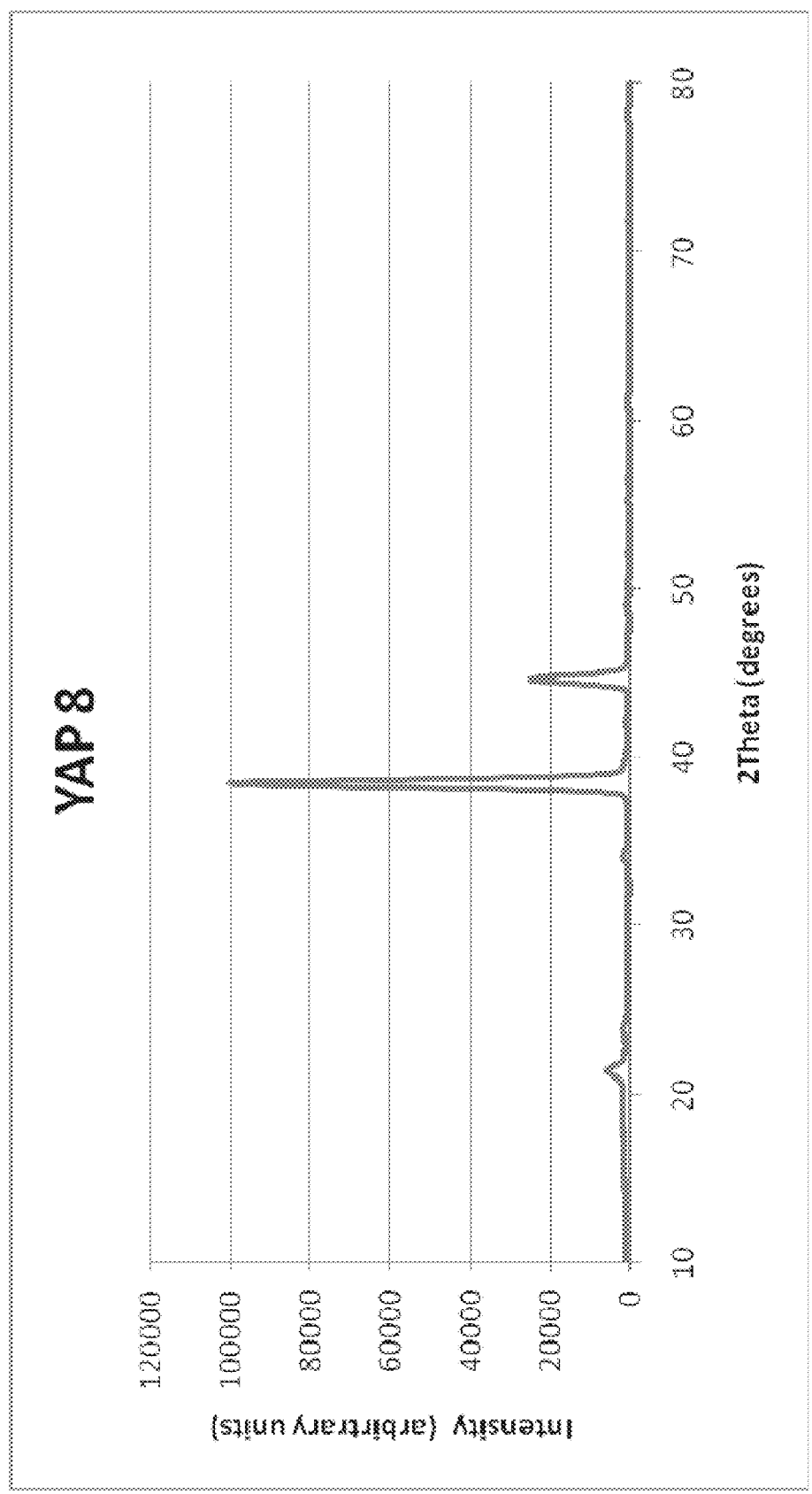
Figure 10K:
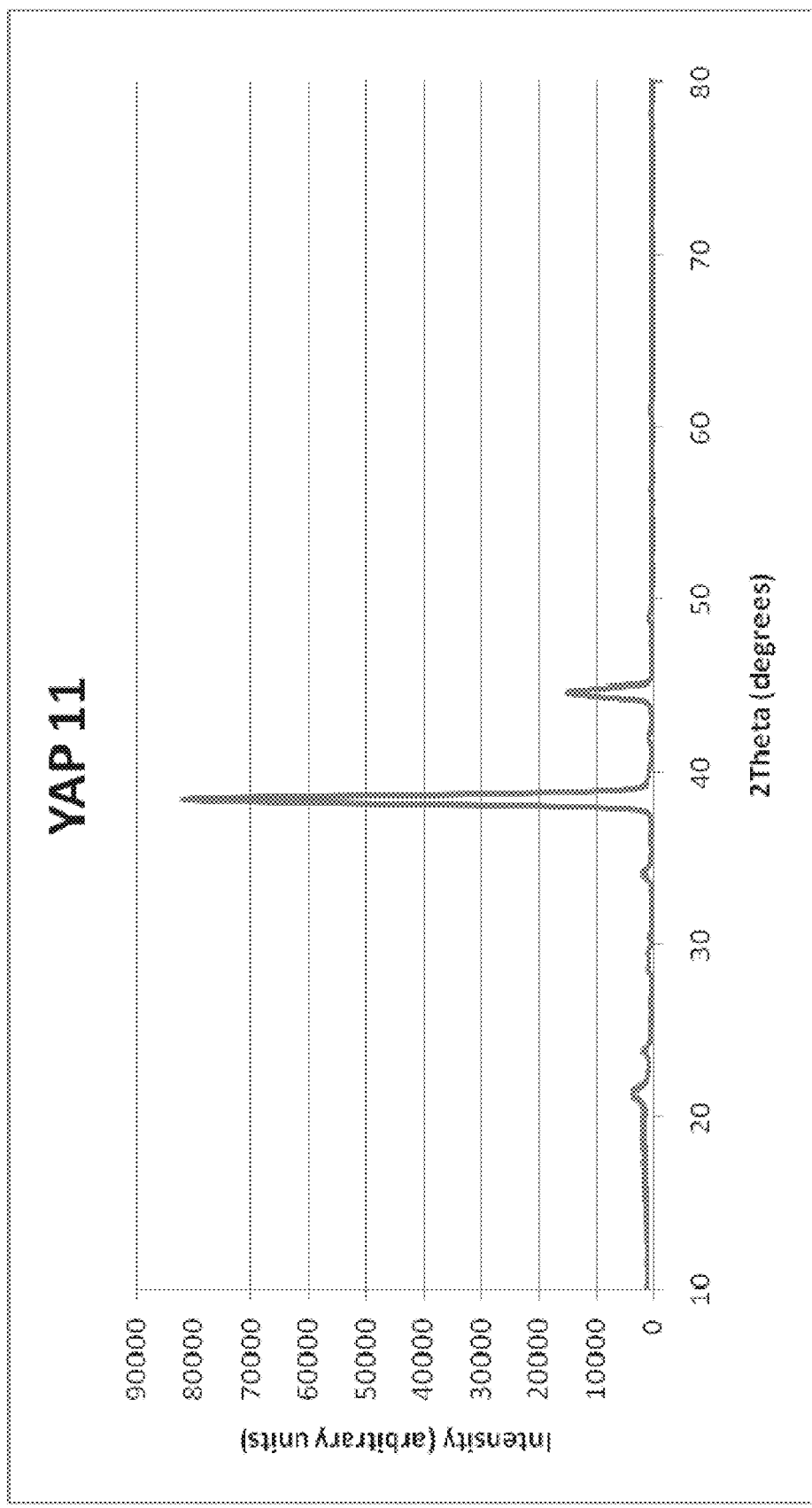
Figure 10L:
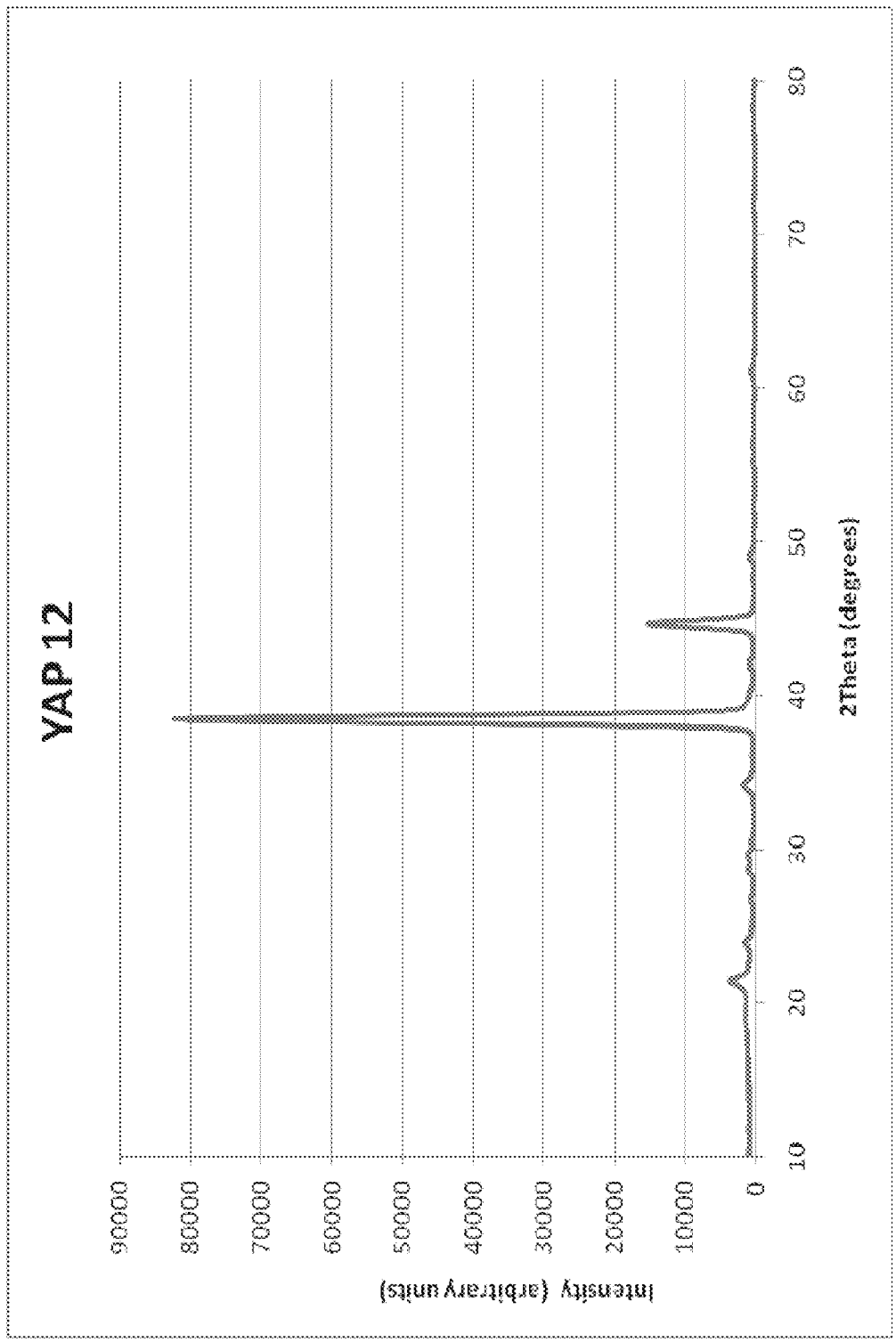

X-ray diffraction can be used to characterize the various formulation's crystal structures and to determine if they are single phase corresponding to either the YAG, YAP, YAM (Yttrium Aluminum Monoclinic), oxide, or fluoride based crystal structures. FIGS. 10(a) and (b) show the x-ray diffraction patterns of the raw starting materials ($Al_2O_3$ and $Y_2O_3$). Select YAP formulations are shown in FIG. 10(c)-(l). The powders appear to be predominately comprised of a single phase having the same orthorhombic crystal structure. Further determination of the grain size can be accomplished using x-ray diffraction.

According to one aspect of the current invention, select pellets are microwave sintered to achieve increased density using a microwave sintering system. The maximum power used should be approximately 2.5 kW, but depends on the size of the crucible, size of the pellet pressed, and density of the material. The temperature could be restricted to below 1500° C., and the power could be increased 0.2 kW every 2 minutes until the 2.5 kW is reached.

Select pellets can also be melted down for subsequent crushing into powder. An electron beam vacuum system and electron beam assembly can be used to melt the pellet formulations. The pellets can be melted to different degrees.

Figure 11A:
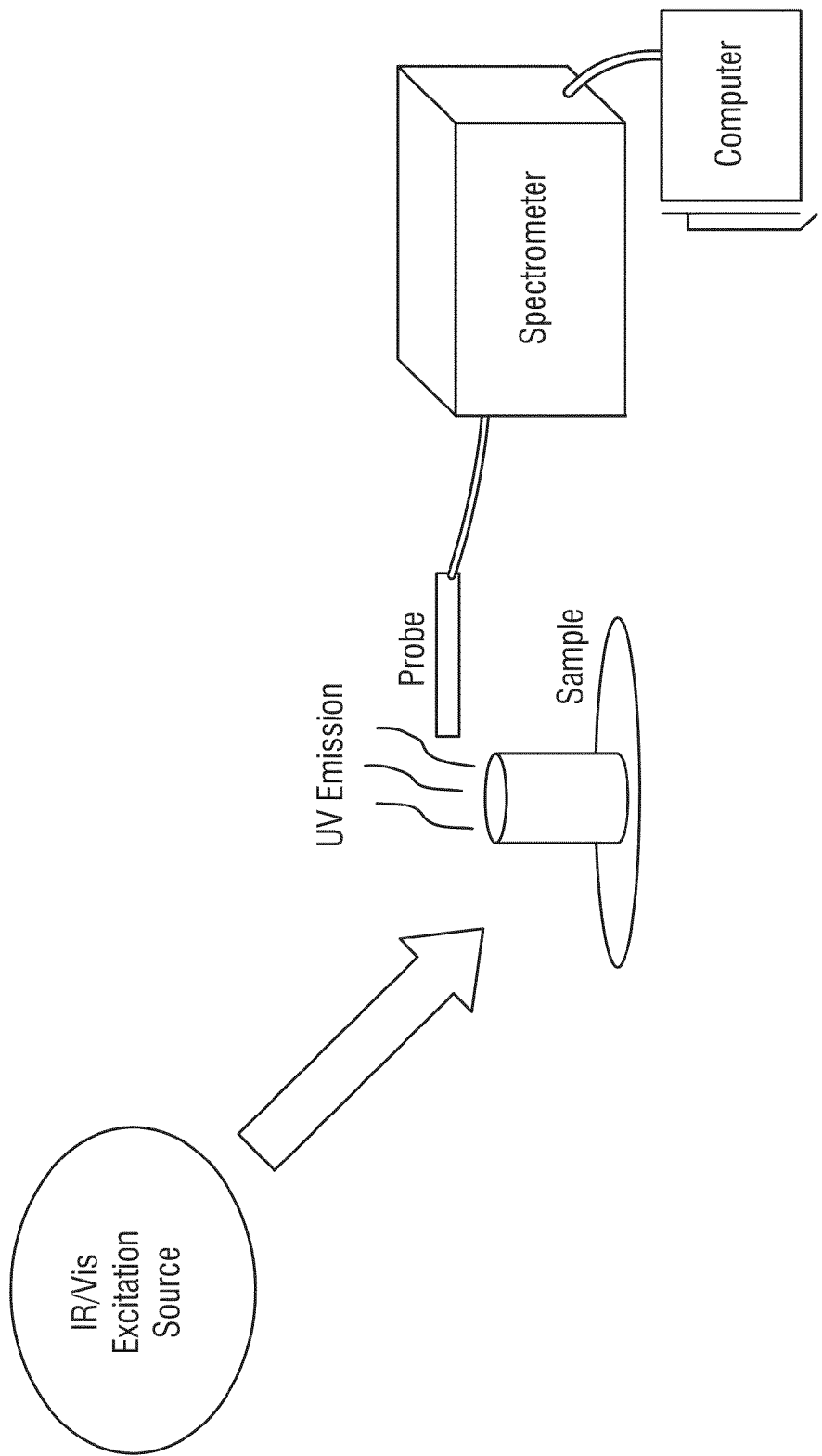
FIG. 11($a$) is a schematic representation of the primary components for screening/measuring up-conversion for a portable device according to one aspect of the present invention.
Figure 11B:
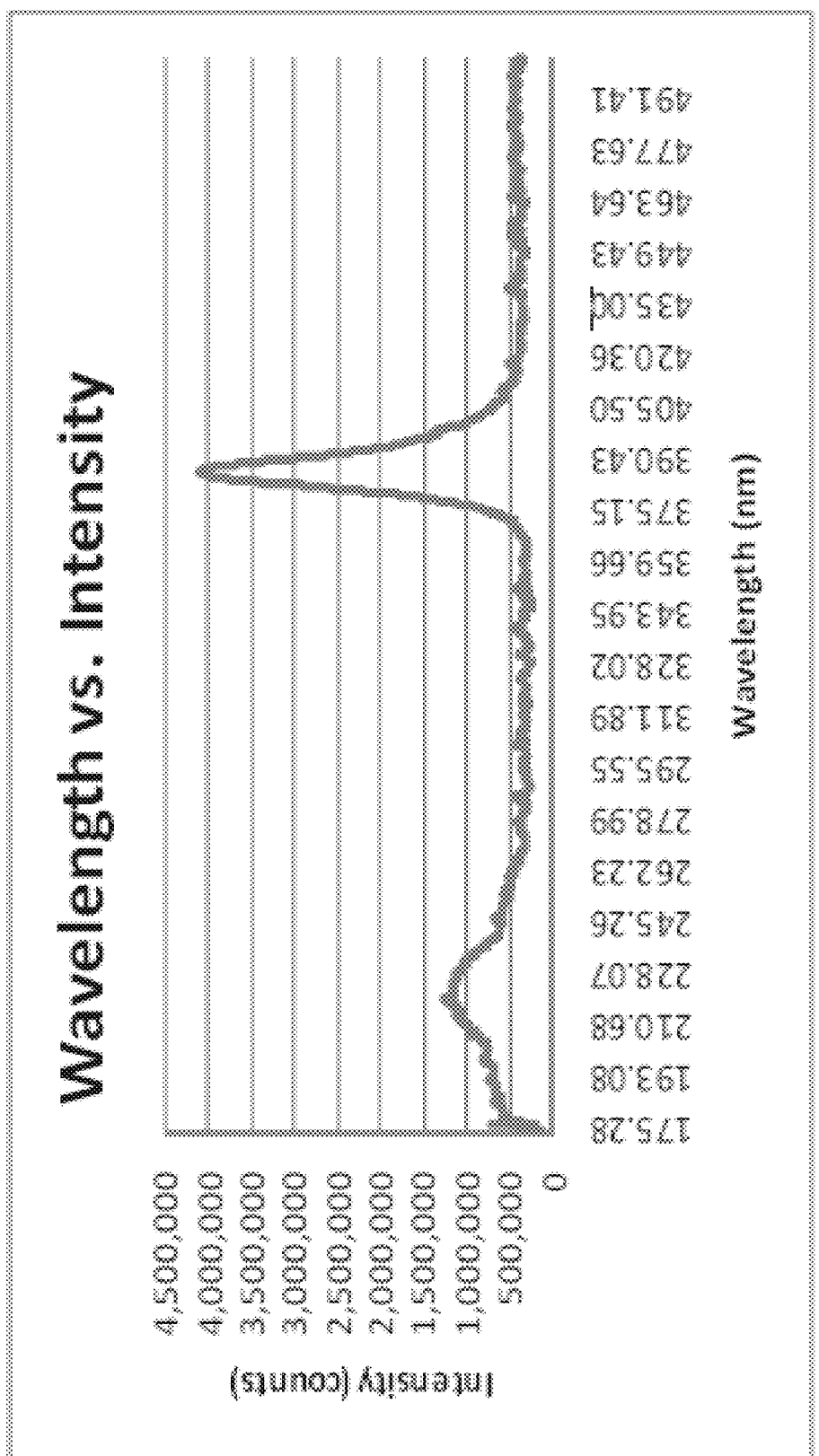

A portable spectrometer could be used to determine the up-conversion behavior of the various material systems of the present invention. The portable system could be configured to allow testing and evaluating of materials from increased standoff distances. FIG. 11(a) shows a schematic representation of one embodiment of a portable spectrometer. FIG. 11(b) shows the emission wavelength vs. intensity for one embodiment of a portable spectrometer for a 380 nm light source. A modified Raman system may be used to evaluate the various formulations and to isolate particular wavelengths in the UV range. The Raman system can be used in the following way:

1. A sample is placed on a stage;
2. The stage is adjusted in the vertical direction to focus the white light through a beam splitter on the sample surface;
3. A laser diode is coupled with a collimating and focusing lens, and then placed on a goniometer to allow adjustments of the laser position on the sample at an angle of approximately 3 to 5 degrees;
4. The laser is adjusted to overlap the focused white light on the sample surface;
5. The beam splitter is then adjusted to remove the white light source;
6. The shutter is then opened to allow the reflected beam from the sample to travel to the spectrometer and acquire the spectrum;
7. The signal is then optimized by adjusting the power to avoid saturation. Maximum peak intensity at a 808 nm wavelength is achieved by adjusting the goniometer and stage;
8. Once optimum position is reached, the laser diode controller is set to 20 mW; and
9. Data is then collected and integrated using the computer software.

Figure 12:
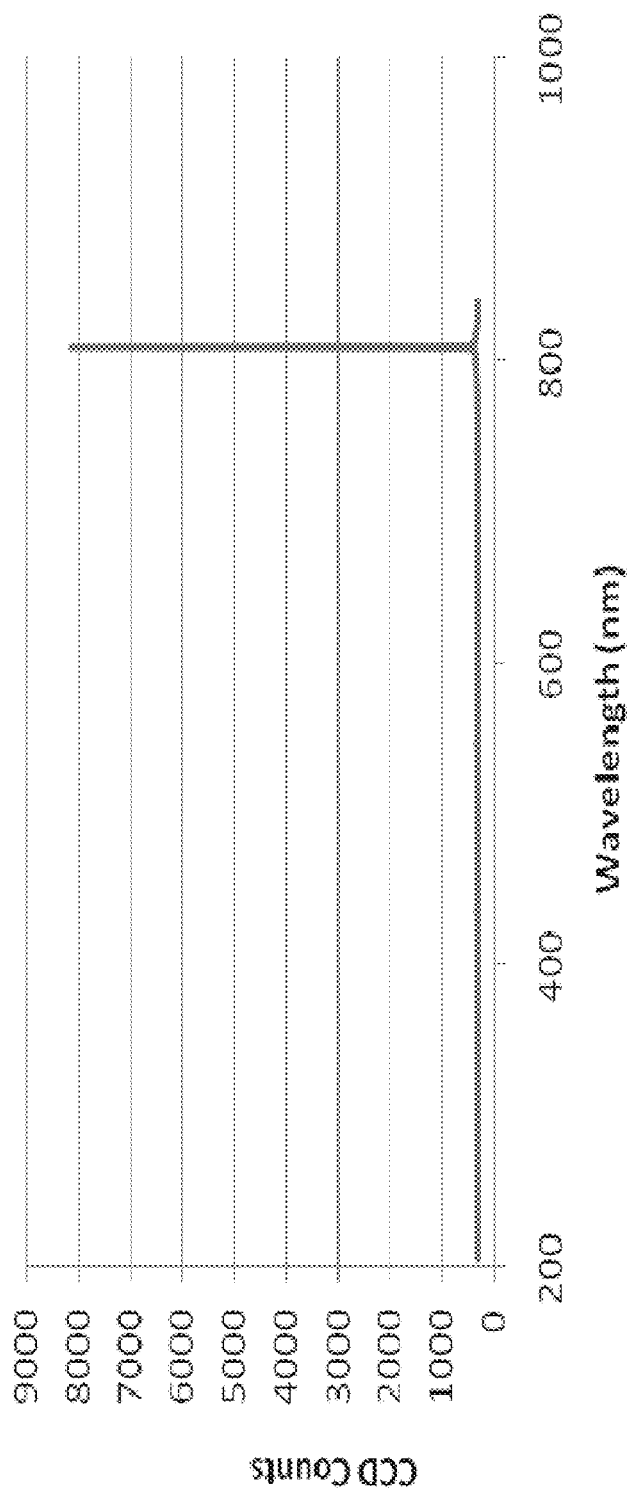
FIG. 12 is a graph of the emission spectra of alumina powder using 808 nm excitation and showing no up-conversion.
Figure 13:
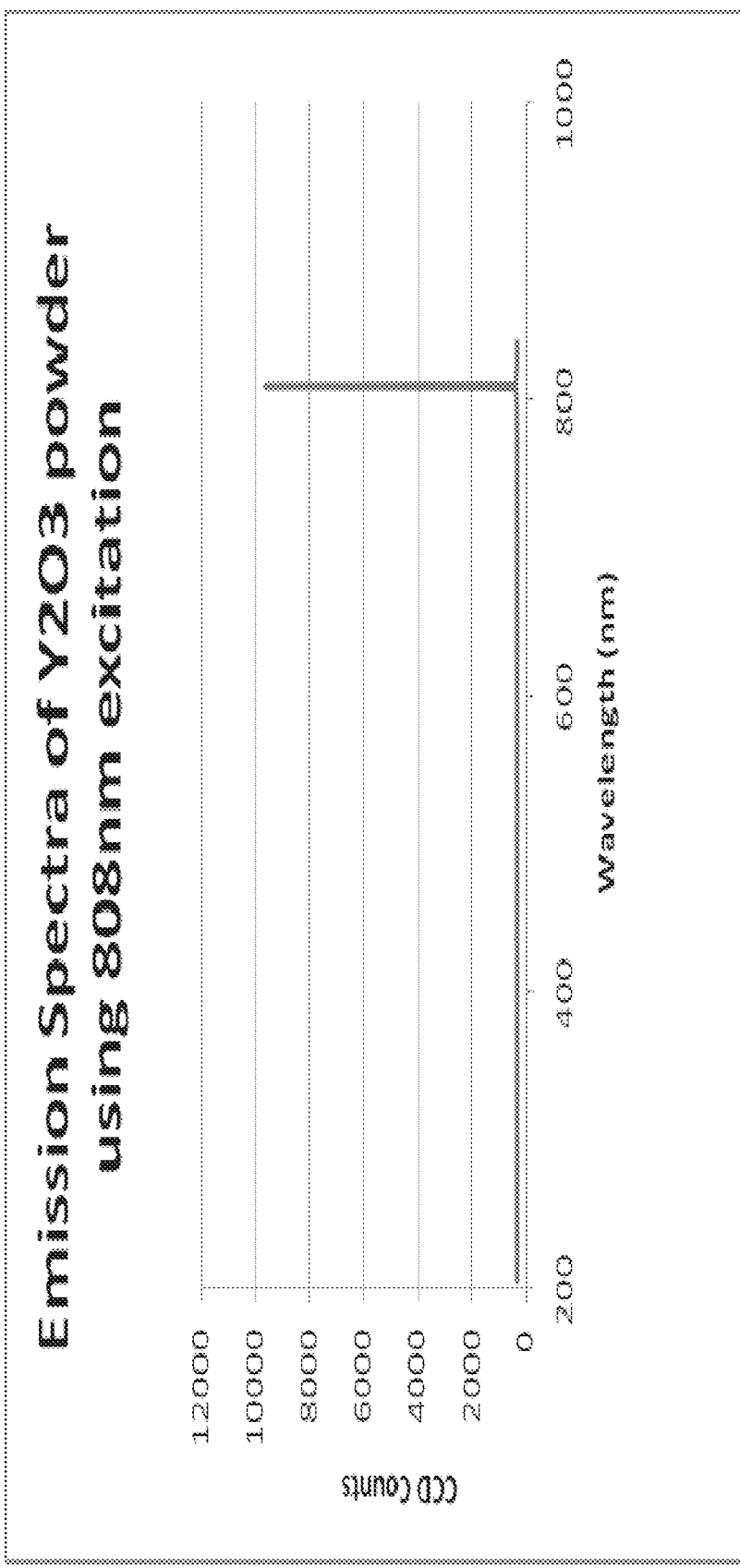
FIG. 13 is a graph of the emission spectra of yttria powder using 808 nm excitation and showing no up-conversion.
Figure 14:
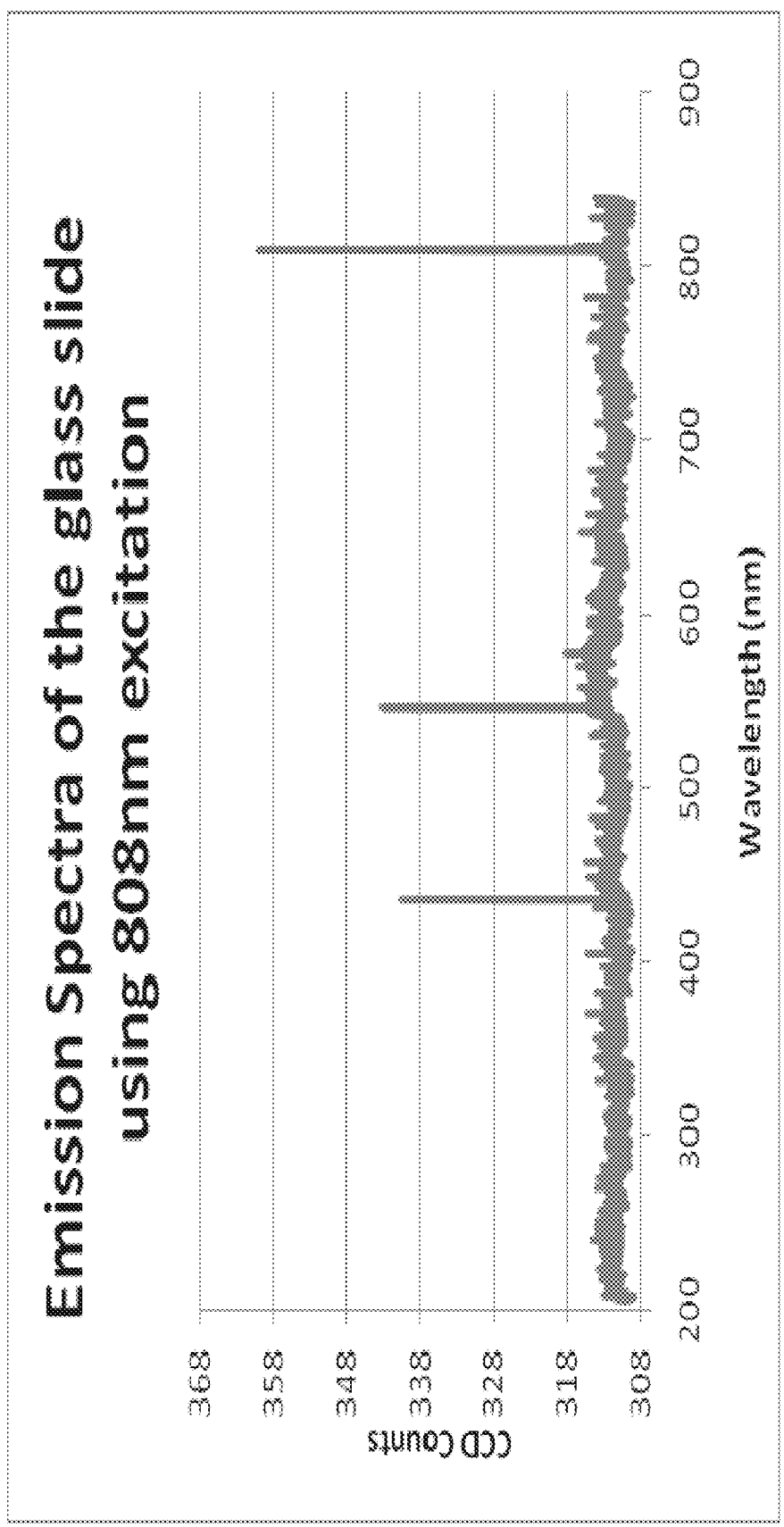
FIG. 14 is a graph of the emission spectra of a glass slide using 808 nm excitation and showing no up-conversion.
Figure 15:
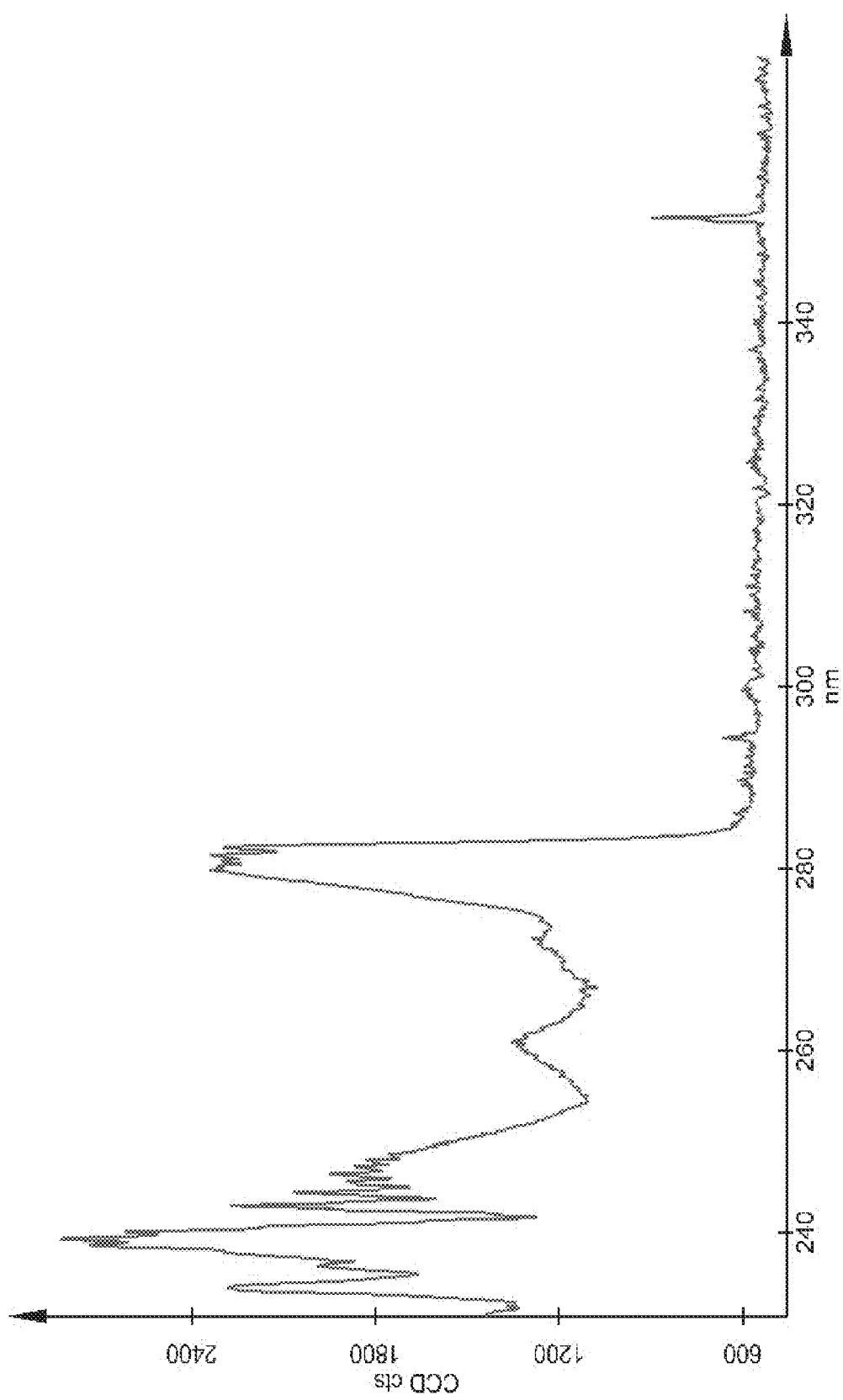
FIG. 15 is a graph of the emission spectra (240 nm to 340 nm) of LuAG powder resulting from an 808 nm excitation wavelength.
Figure 16:
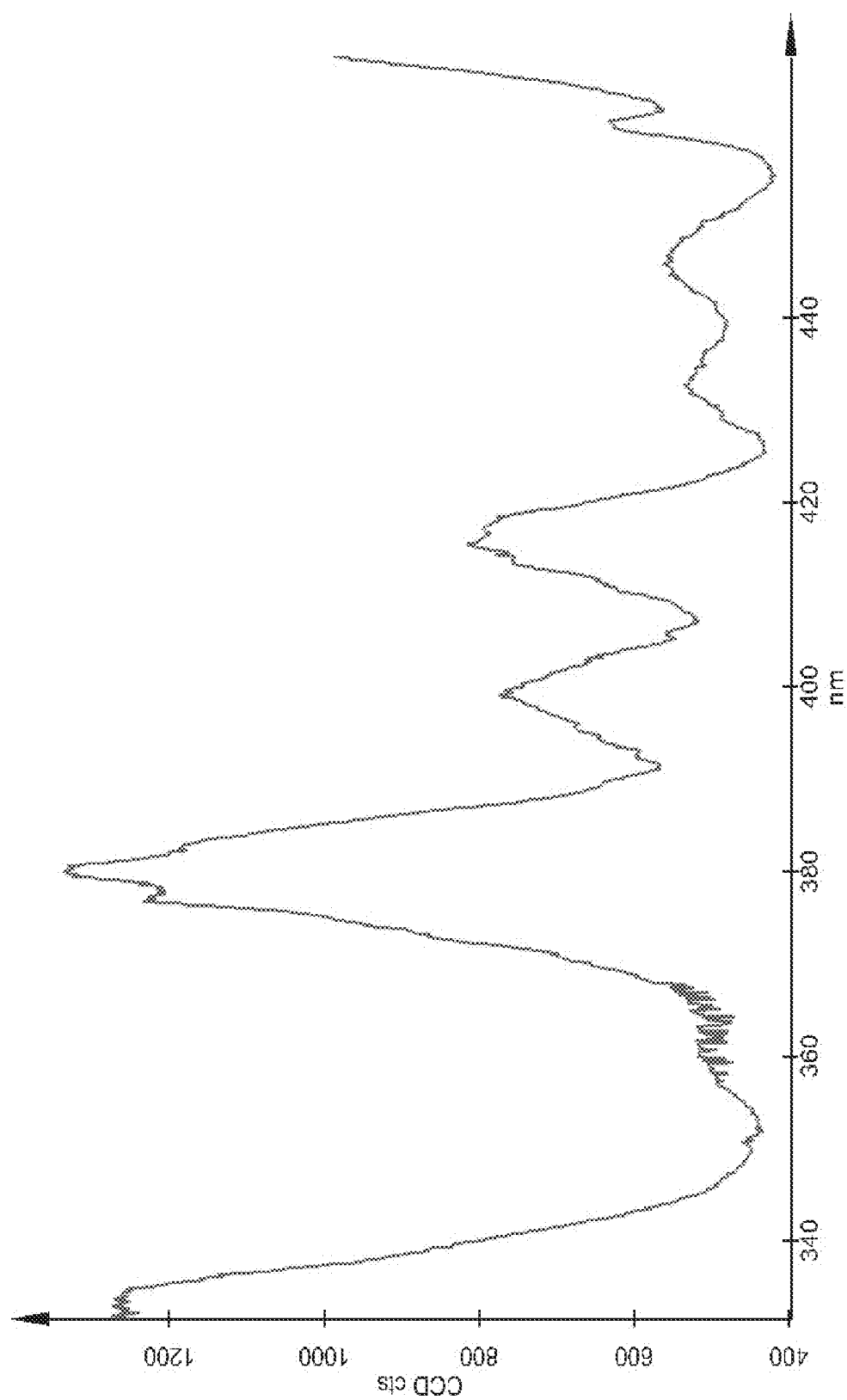
FIG. 16 is a graph of the emission spectra (340 nm to 440 nm) of LuAG powder resulting from an 808 nm excitation wavelength.
Figure 17:
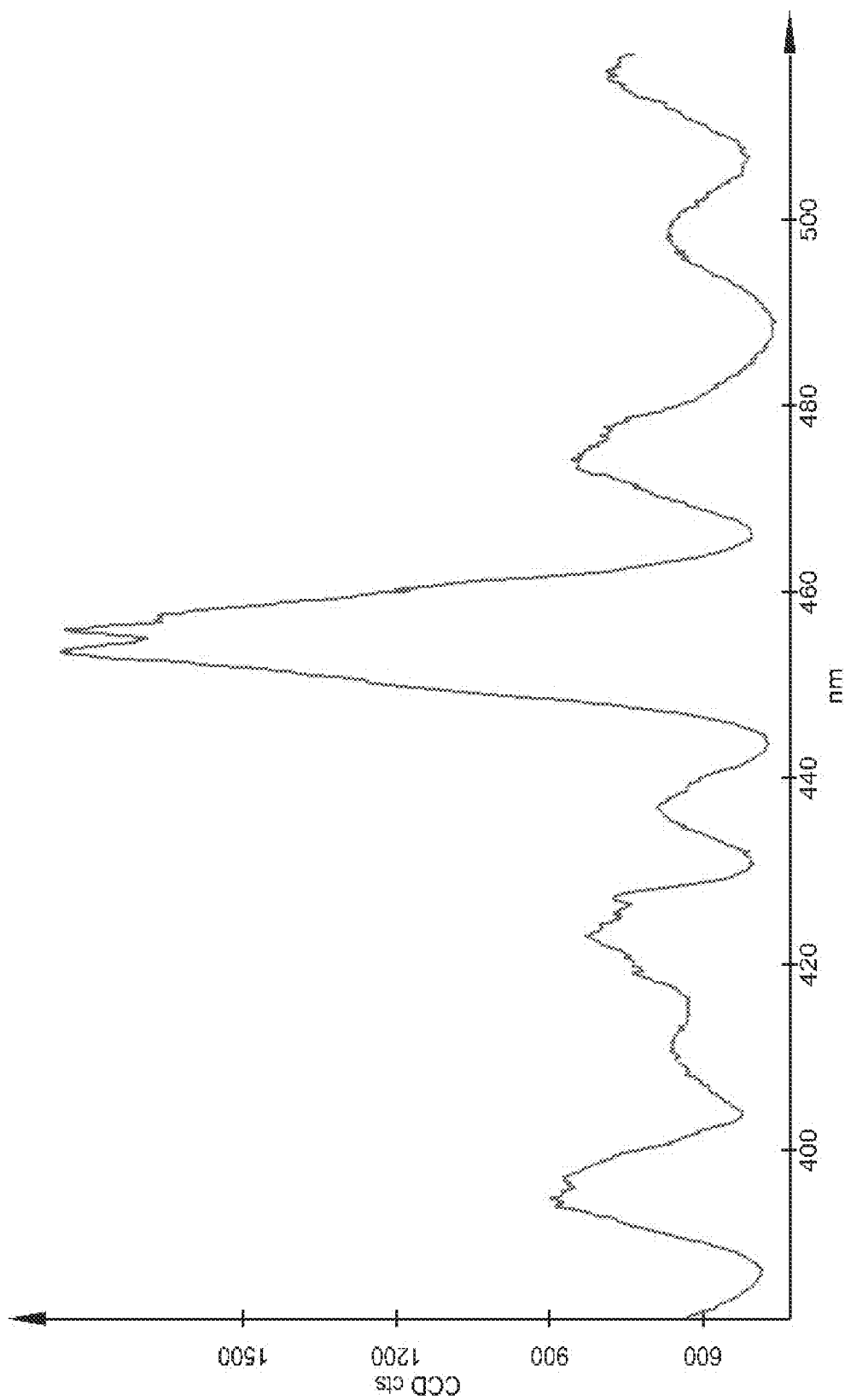
FIG. 17 is a graph of the emission spectra (400 nm to 500 nm) of LuAG powder resulting from an 808 nm excitation wavelength.
Figure 18:
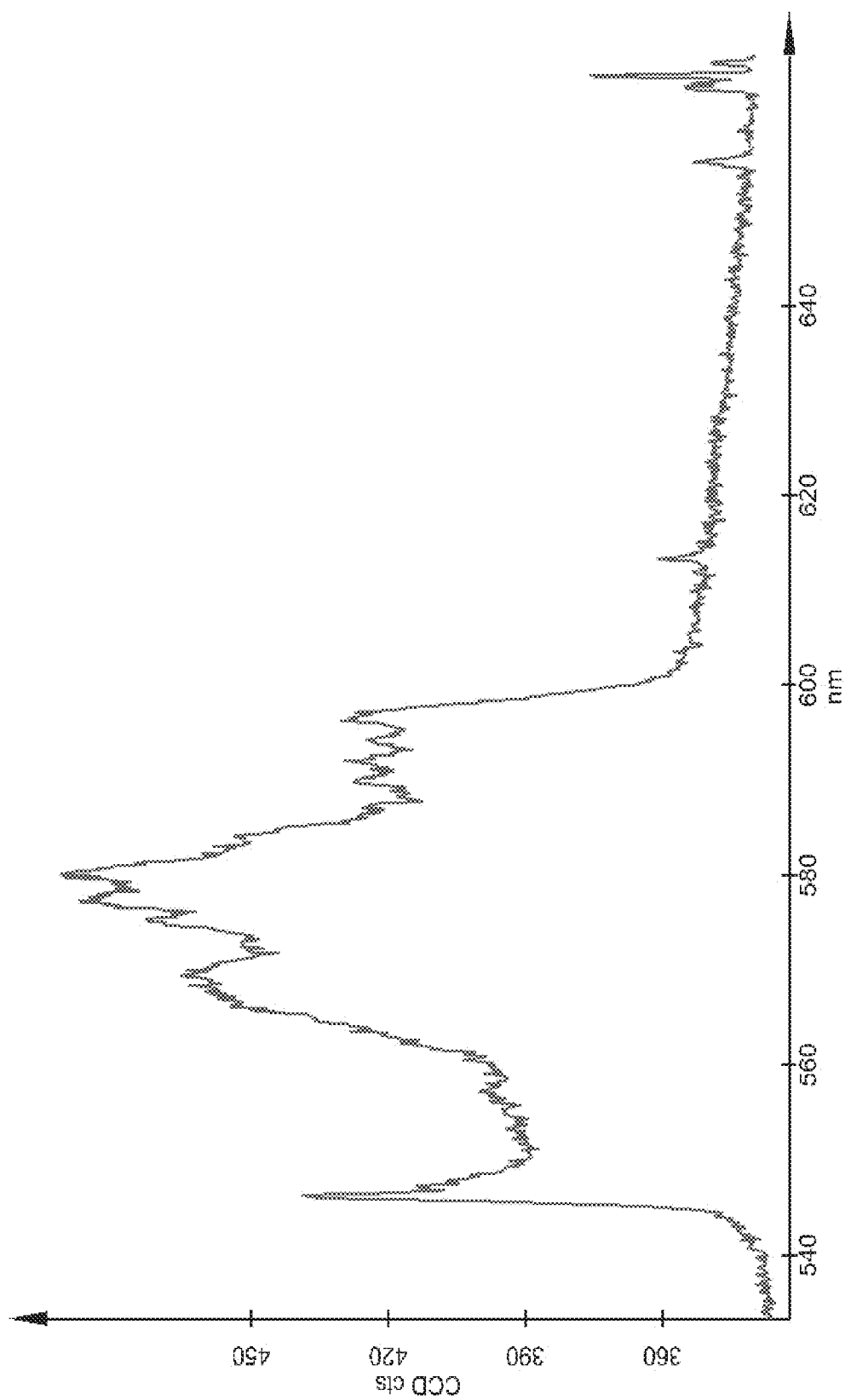
FIG. 18 is a graph of the emission spectra (540 nm to 640 nm) of LuAG powder resulting from an 808 nm excitation wavelength.
Figure 19:
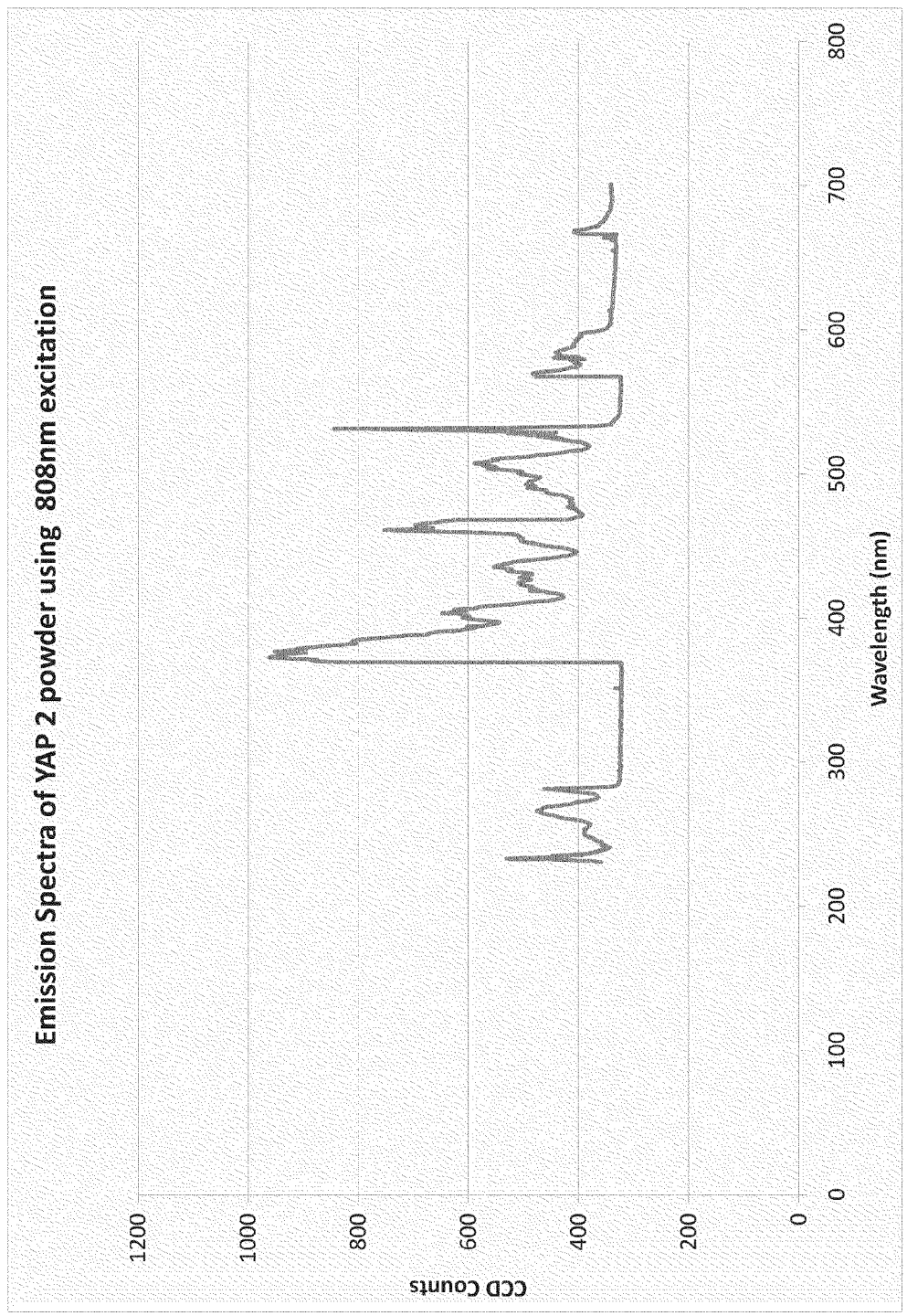
FIG. 19 is a graph of the emission spectra of YAP2 powder formulation resulting from an 808 nm excitation wavelength.
Figure 20:
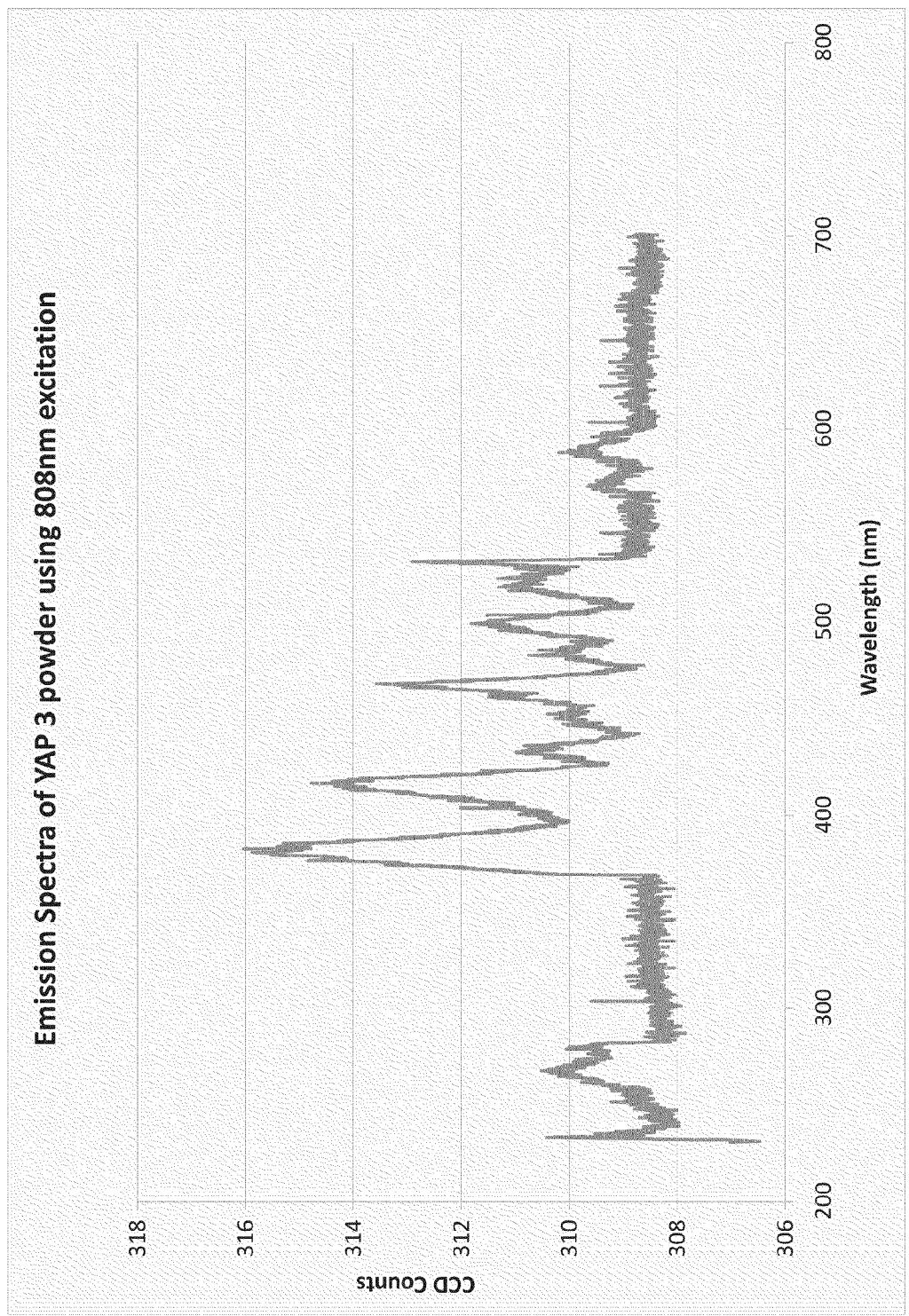
FIG. 20 is a graph of the emission spectra of YAP3 powder formulation resulting from an 808 nm excitation wavelength.
Figure 21:
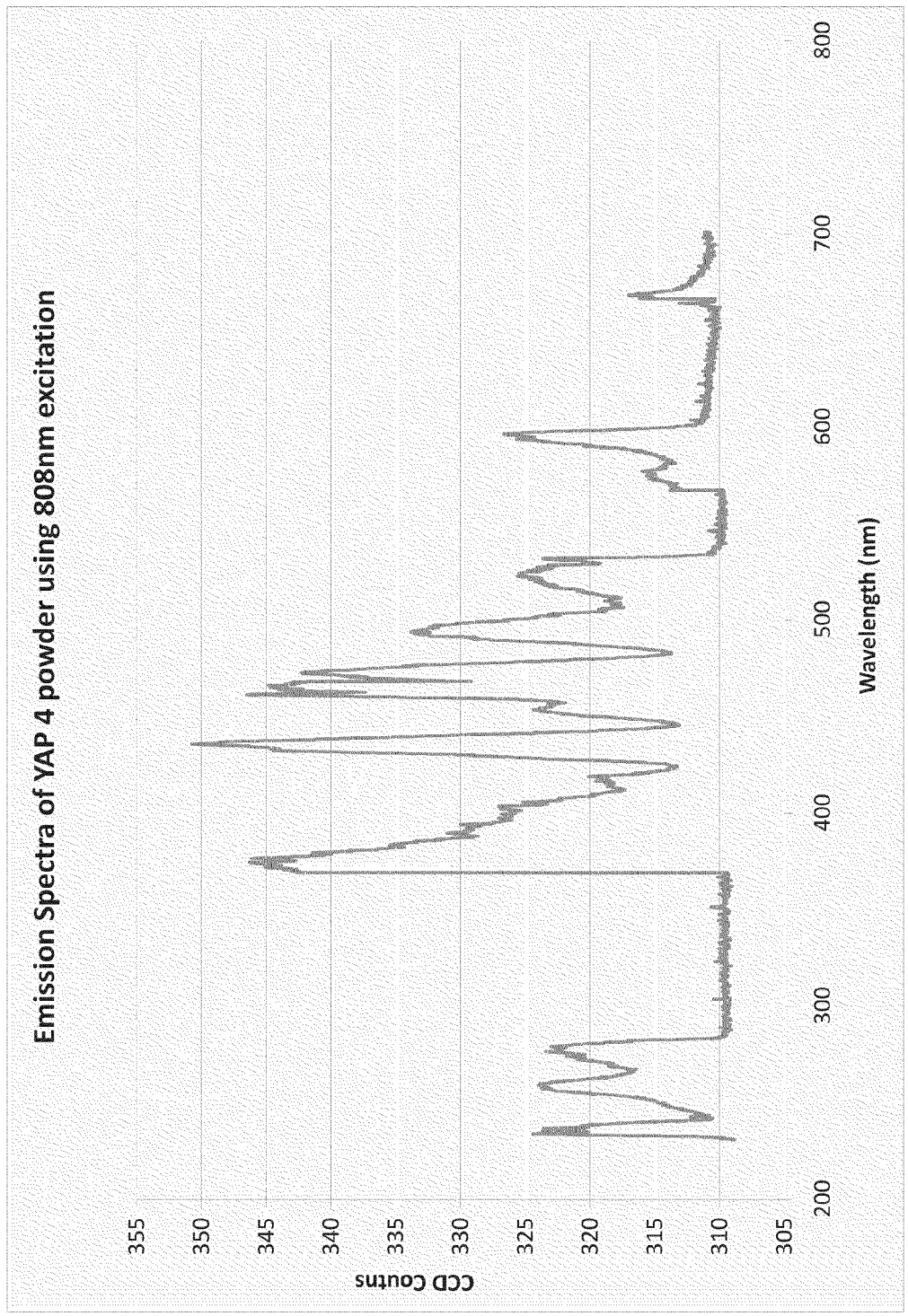
FIG. 21 is a graph of the emission spectra of YAP4 powder formulation resulting from an 808 nm excitation wavelength.
Figure 22:
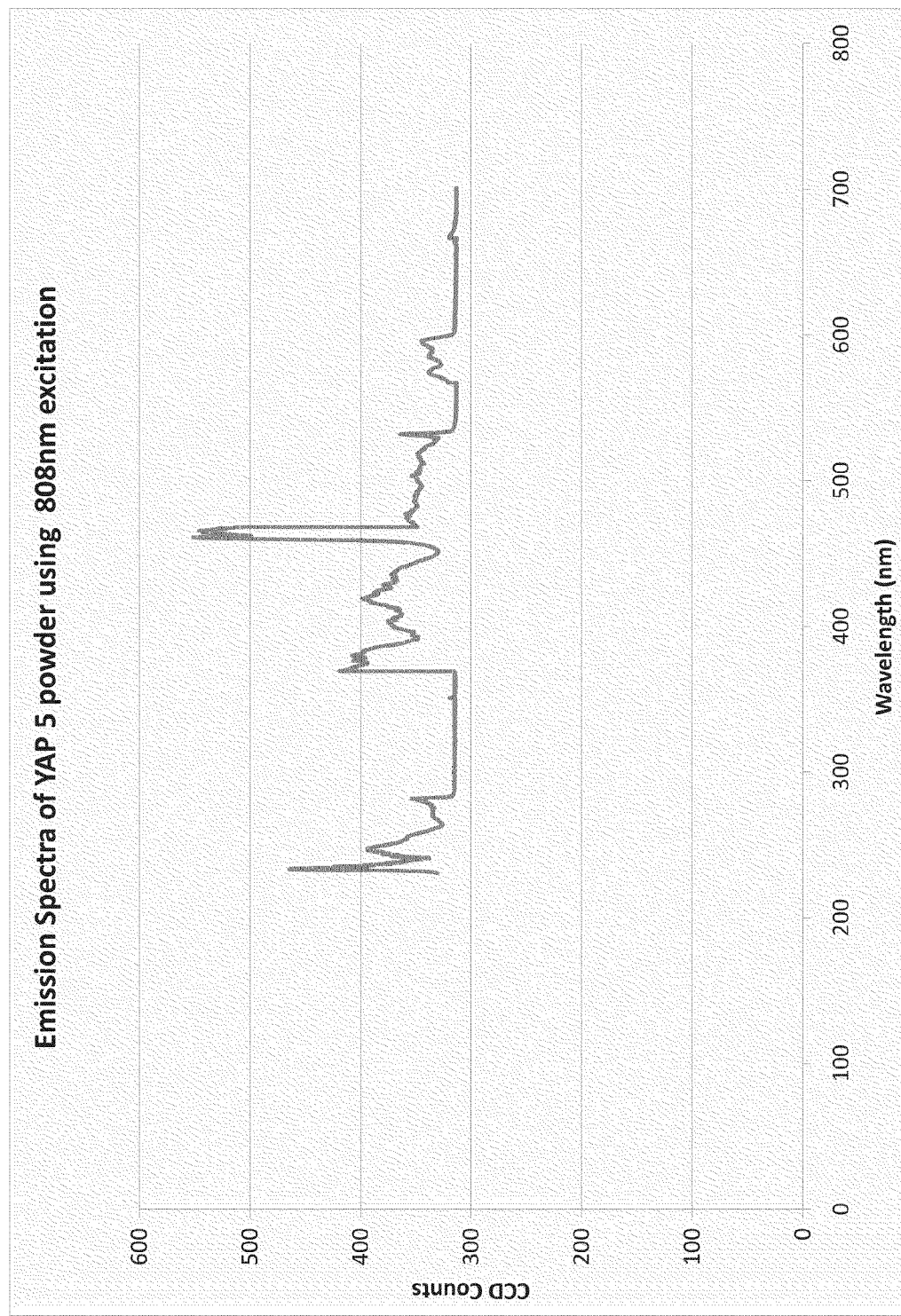
FIG. 22 is a graph of the emission spectra of YAP5 powder formulation resulting from an 808 nm excitation wavelength.
Figure 23:
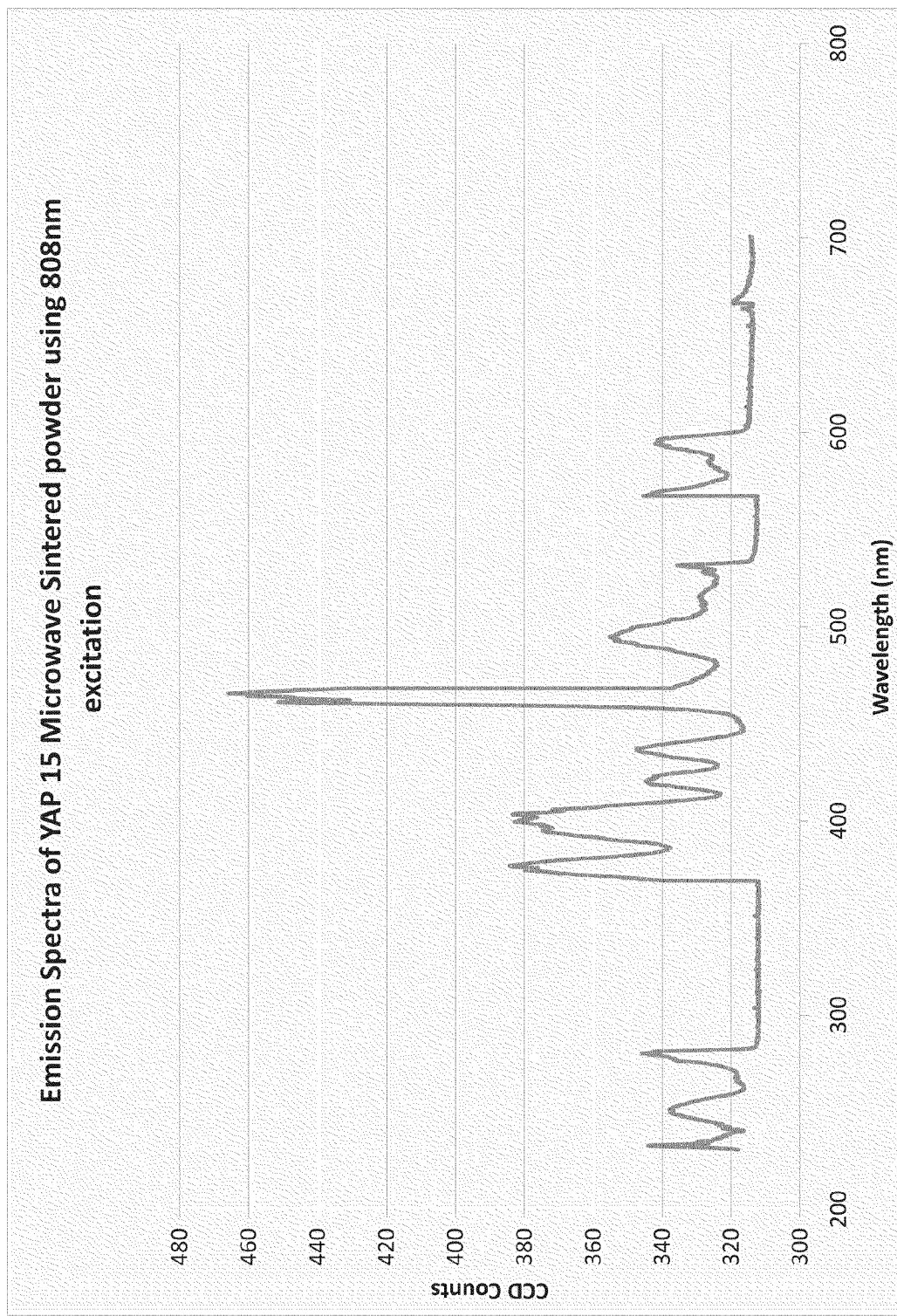
FIG. 23 is a graph of the emission spectra of YAP15 powder formulation resulting from an 808 nm excitation wavelength.
Figure 24:
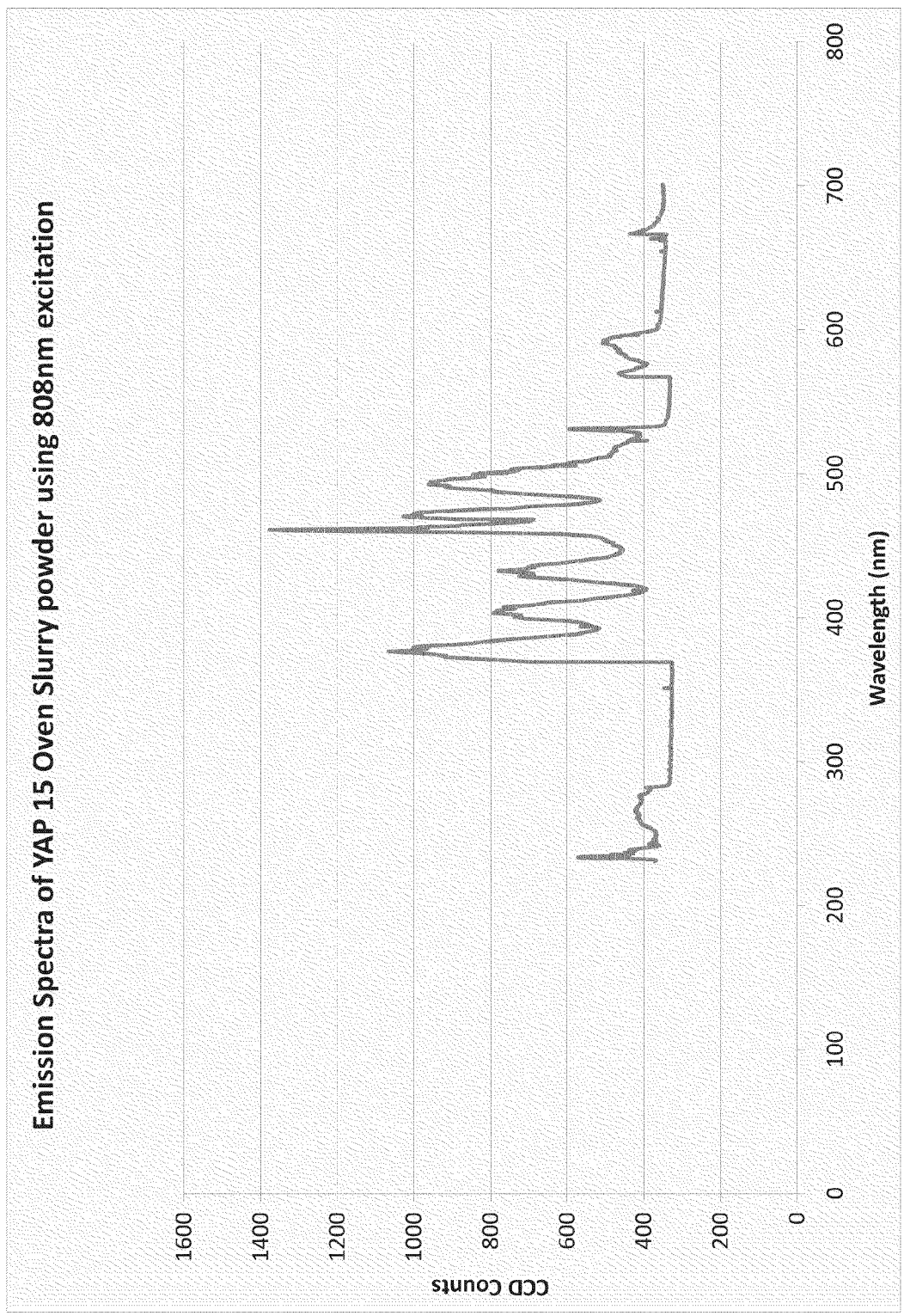
FIG. 24 is a graph of the emission spectra of YAP15 powder formulation resulting from an 808 nm excitation wavelength.
Figure 25:
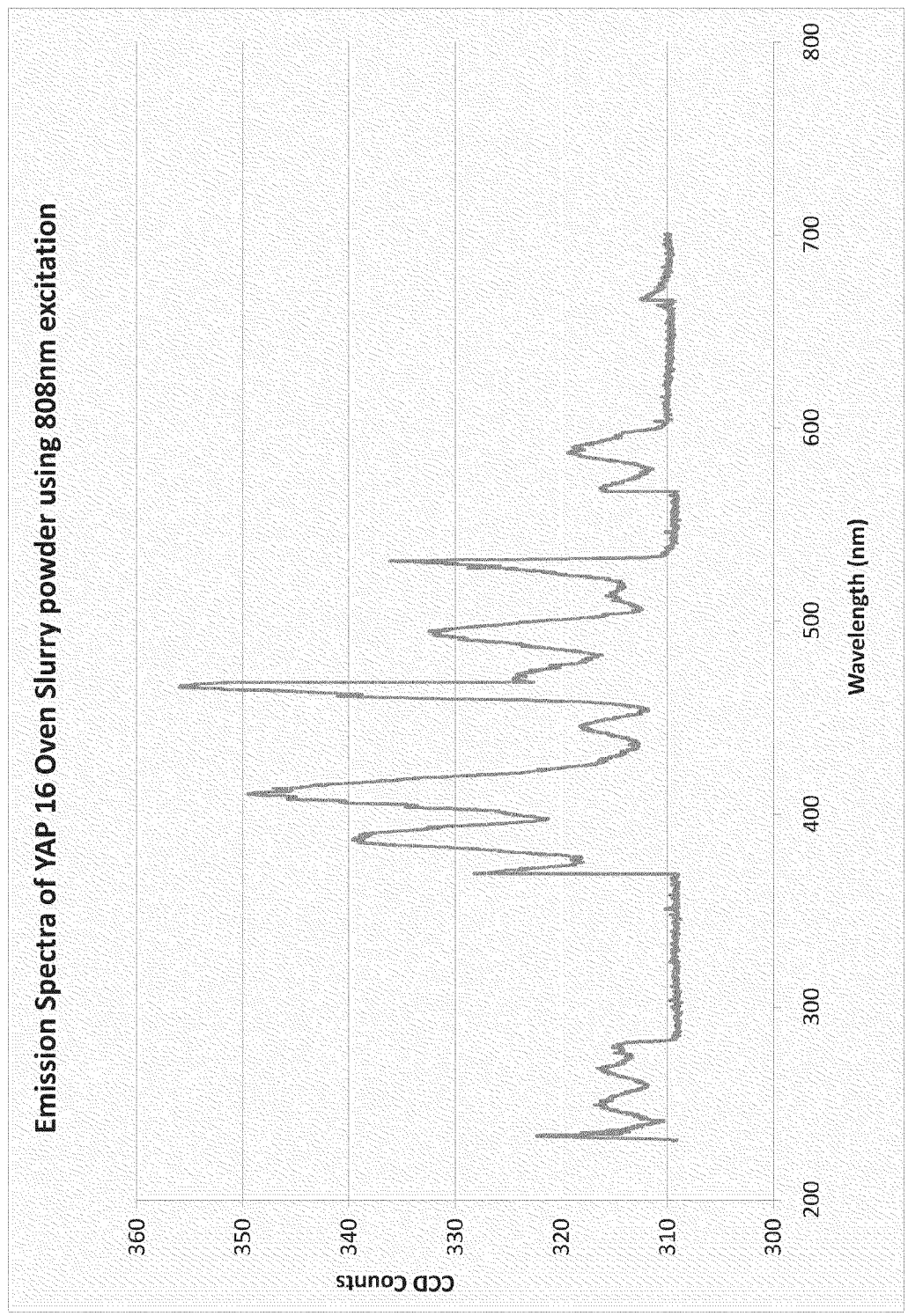
FIG. 25 is a graph of the emission spectra of YAP16 powder formulation resulting from an 808 nm excitation wavelength.
Figure 26:
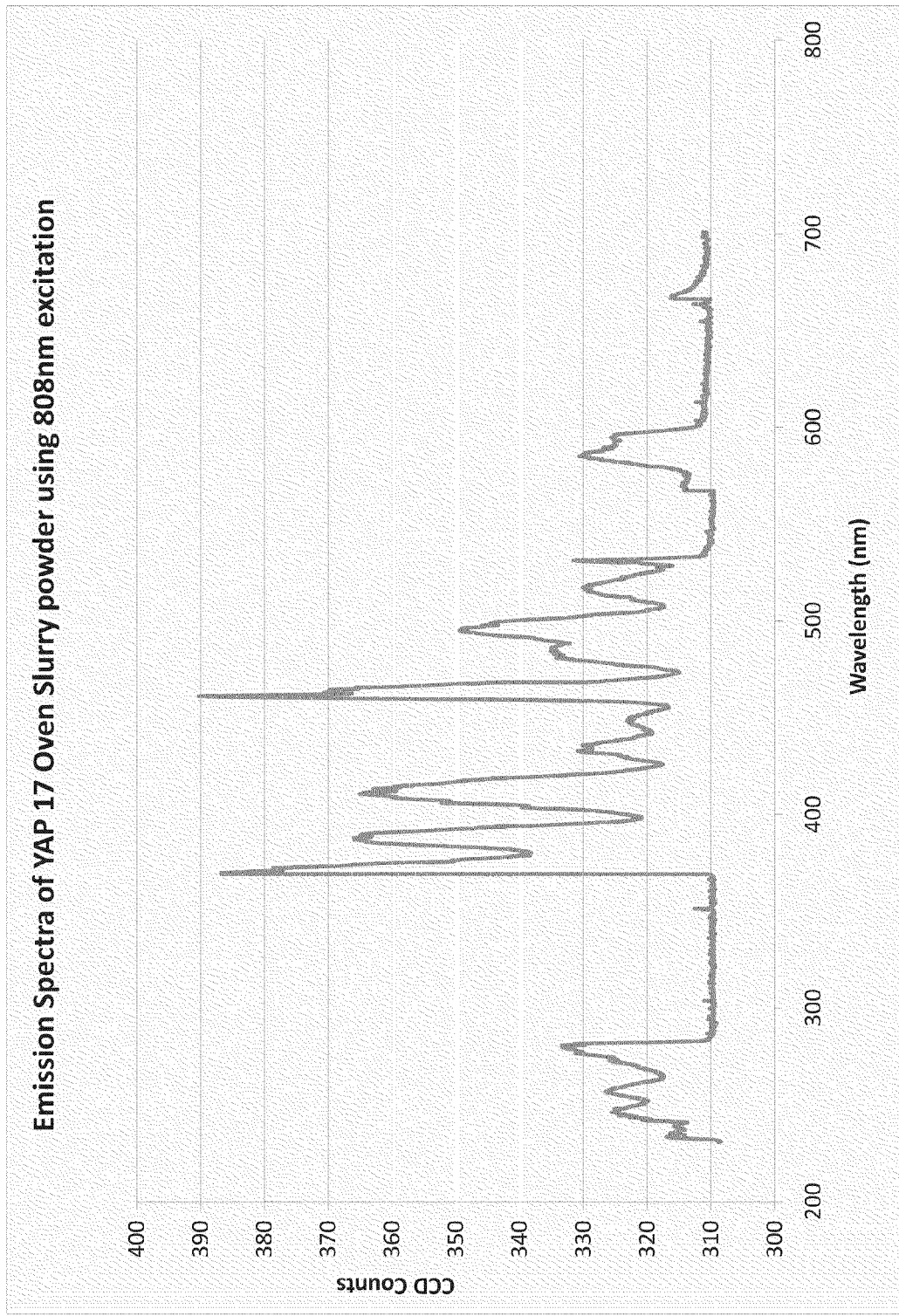
FIG. 26 is a graph of the emission spectra of YAP17 powder formulation resulting from an 808 nm excitation wavelength.
Figure 27A:
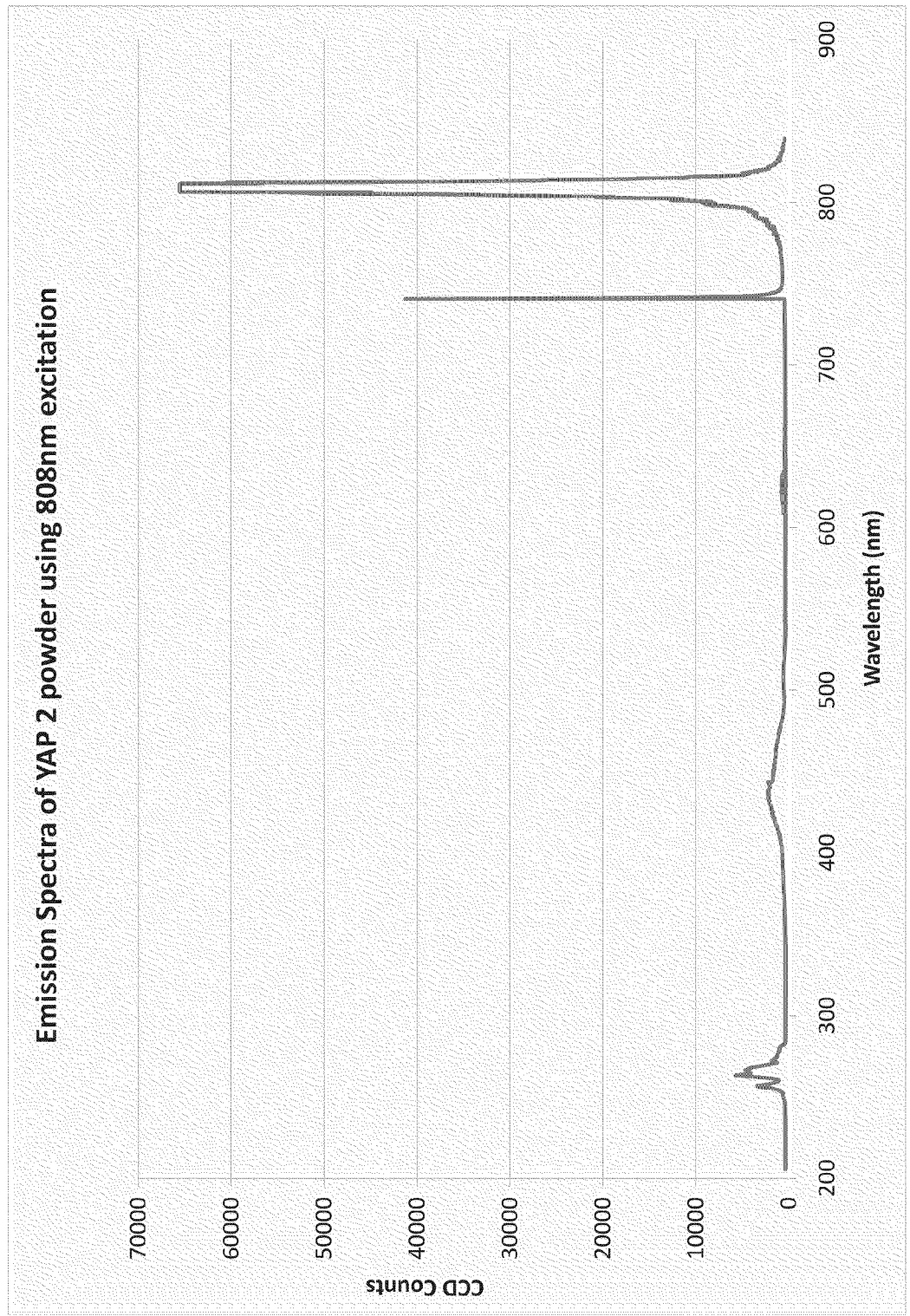
FIG. 27($a$) is a graph of the emission spectra of YAP2 powder formulation resulting from an 808 nm excitation wavelength.
Figure 27B:
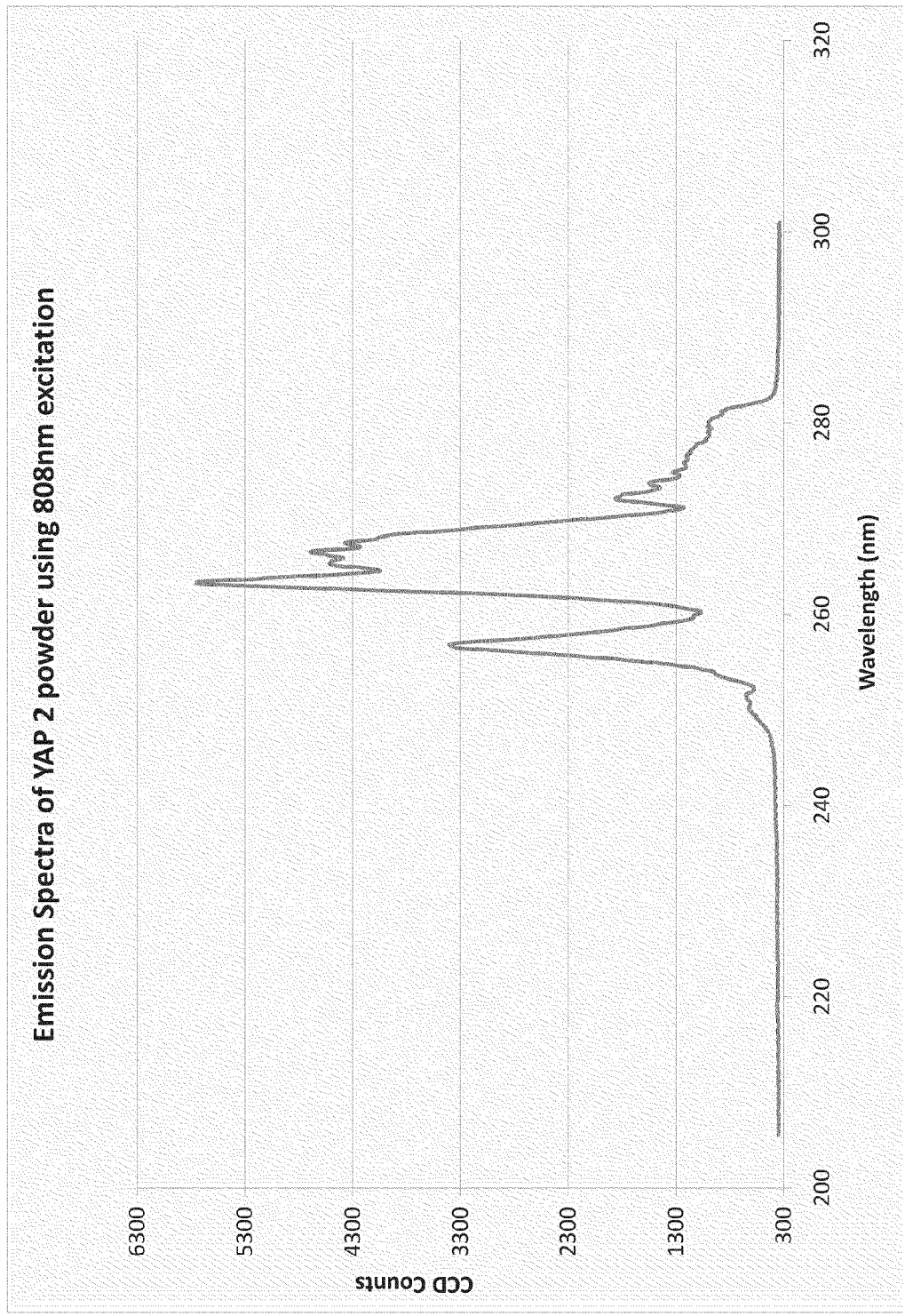
Figure 28A:
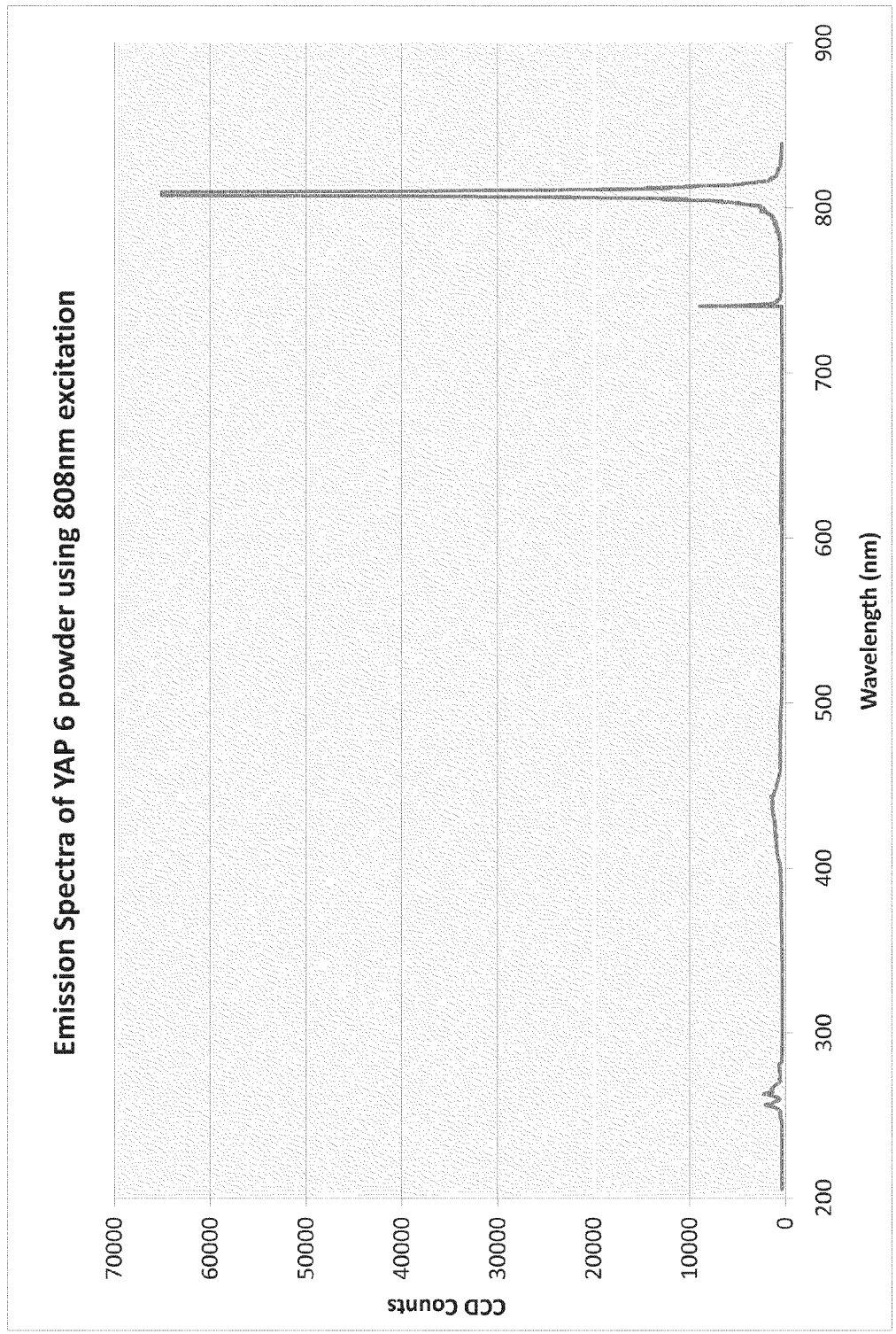
FIG. 28($a$) is a graph of the emission spectra of YAP6 powder formulation resulting from an 808 nm excitation wavelength.
Figure 28B:
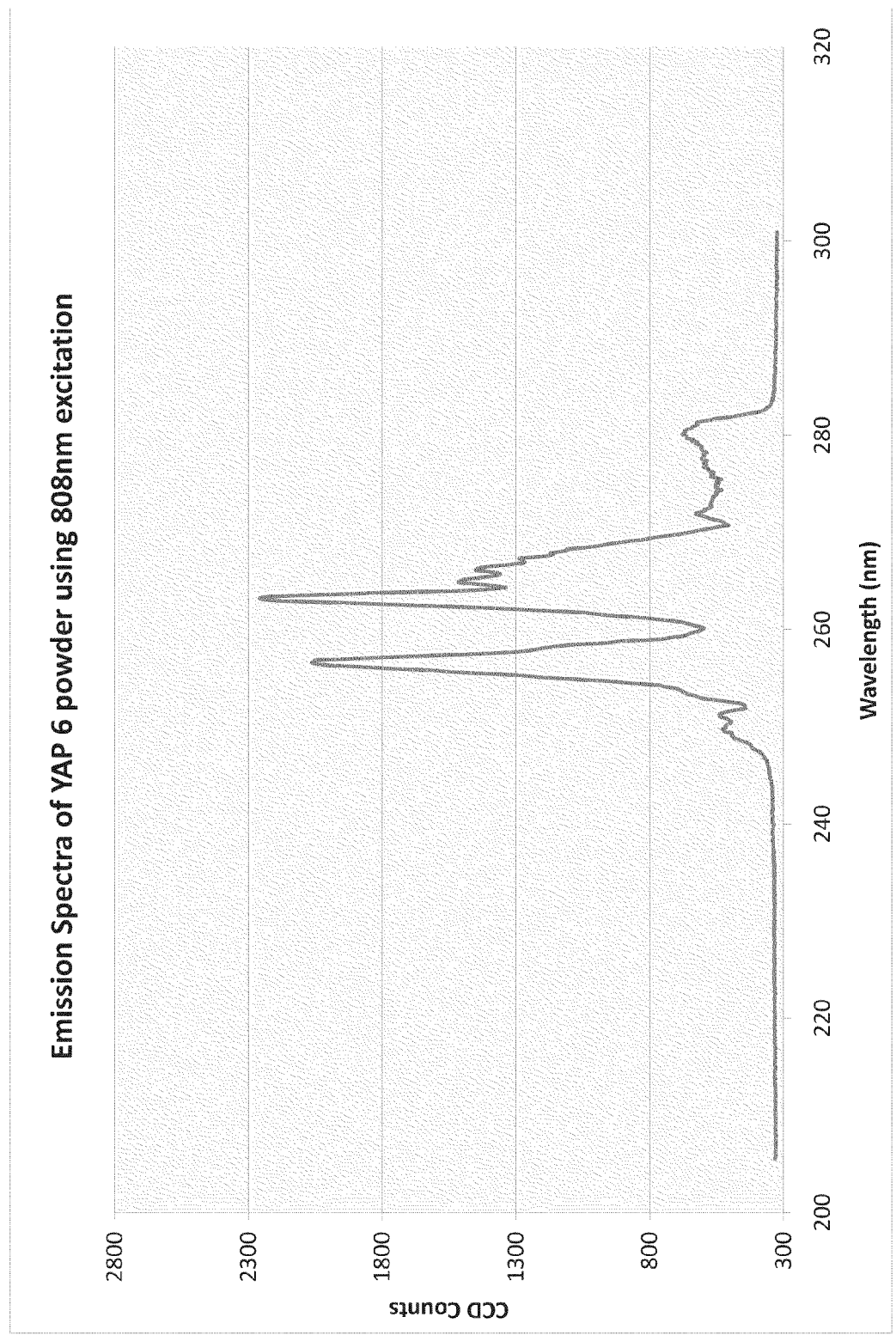
Figure 29A:
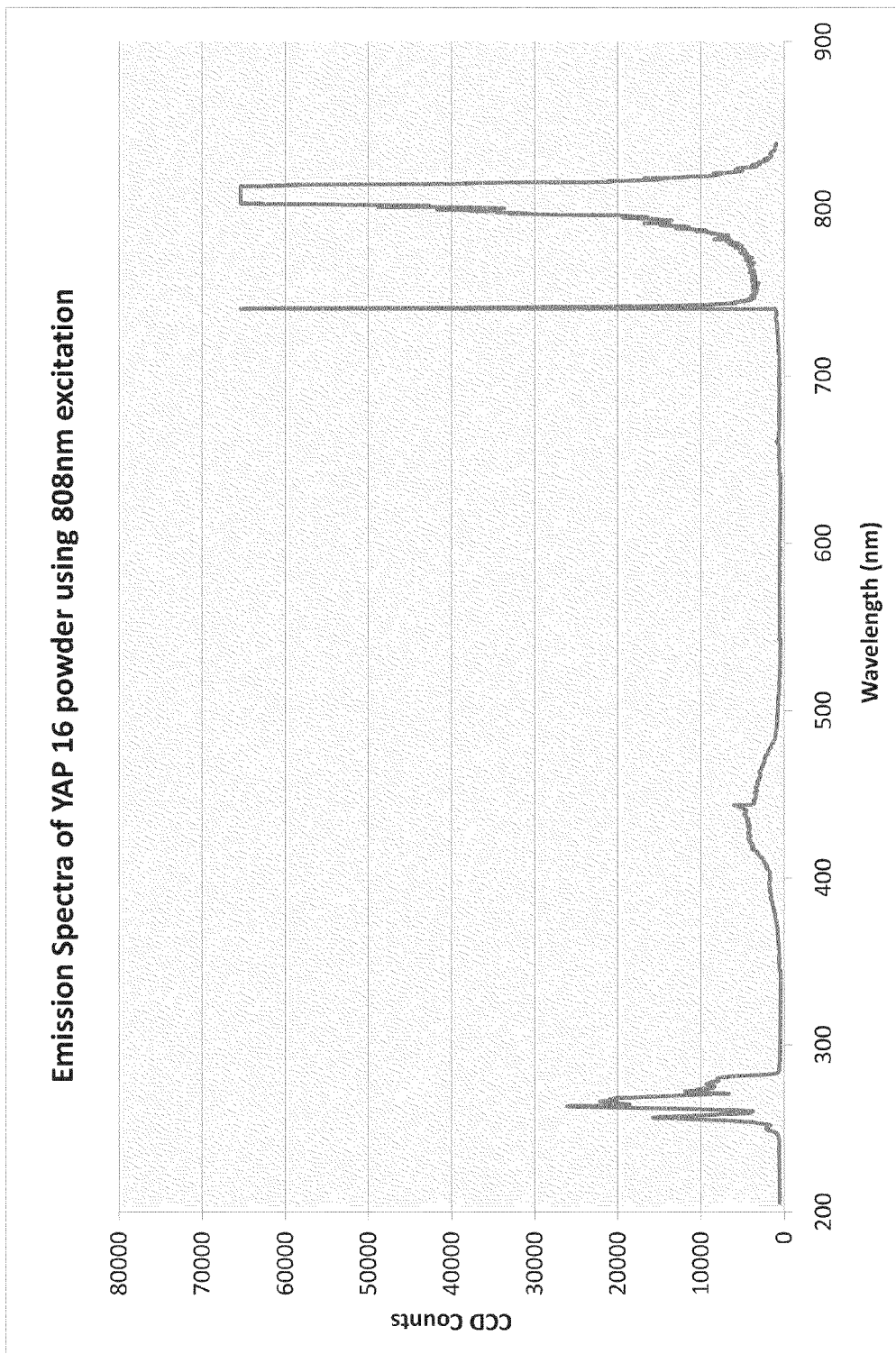
FIG. 29($a$) is a graph of the emission spectra of YAP16 powder formulation resulting from an 808 nm excitation wavelength.
Figure 29B:
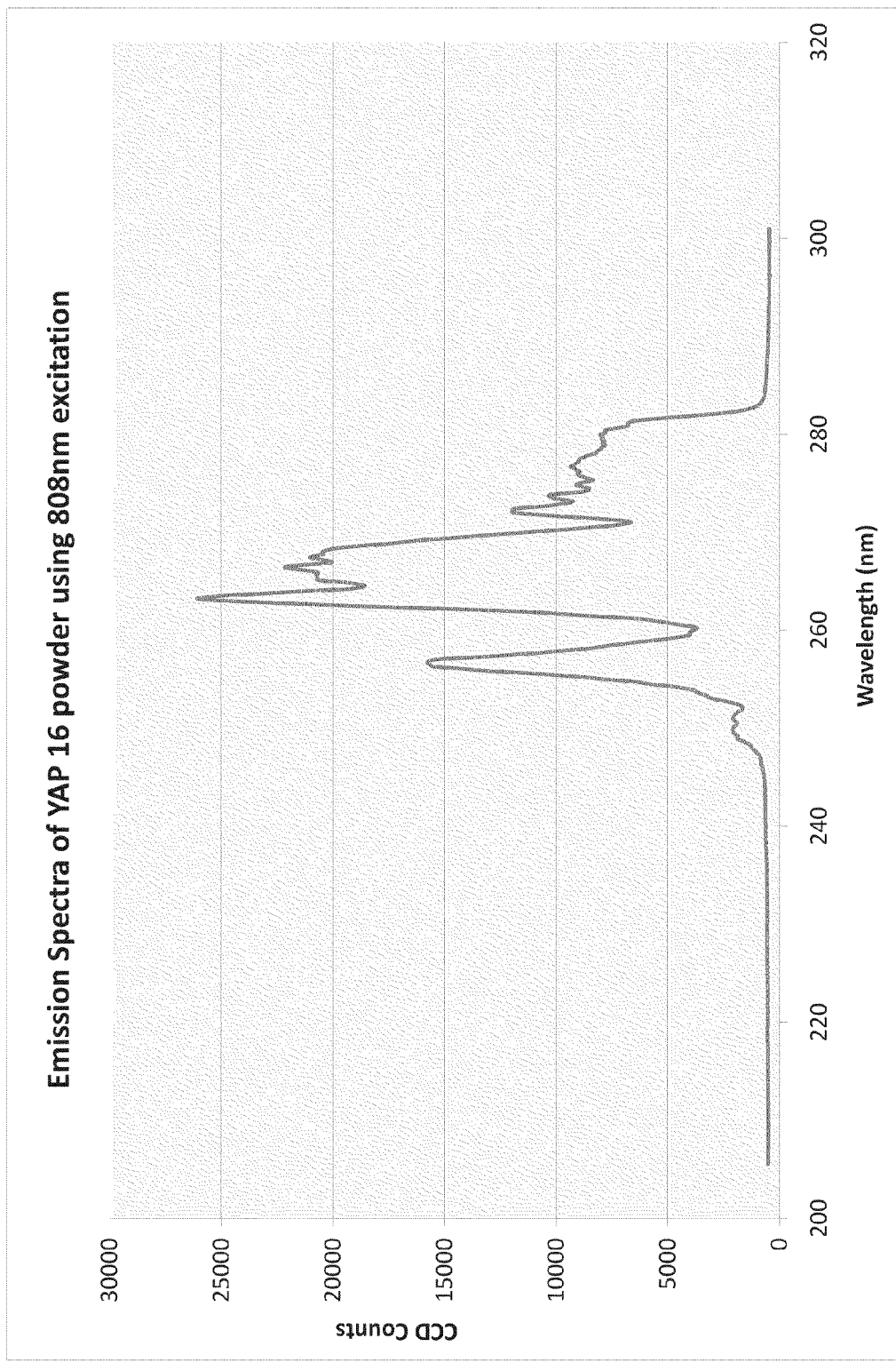
Figure 30A:
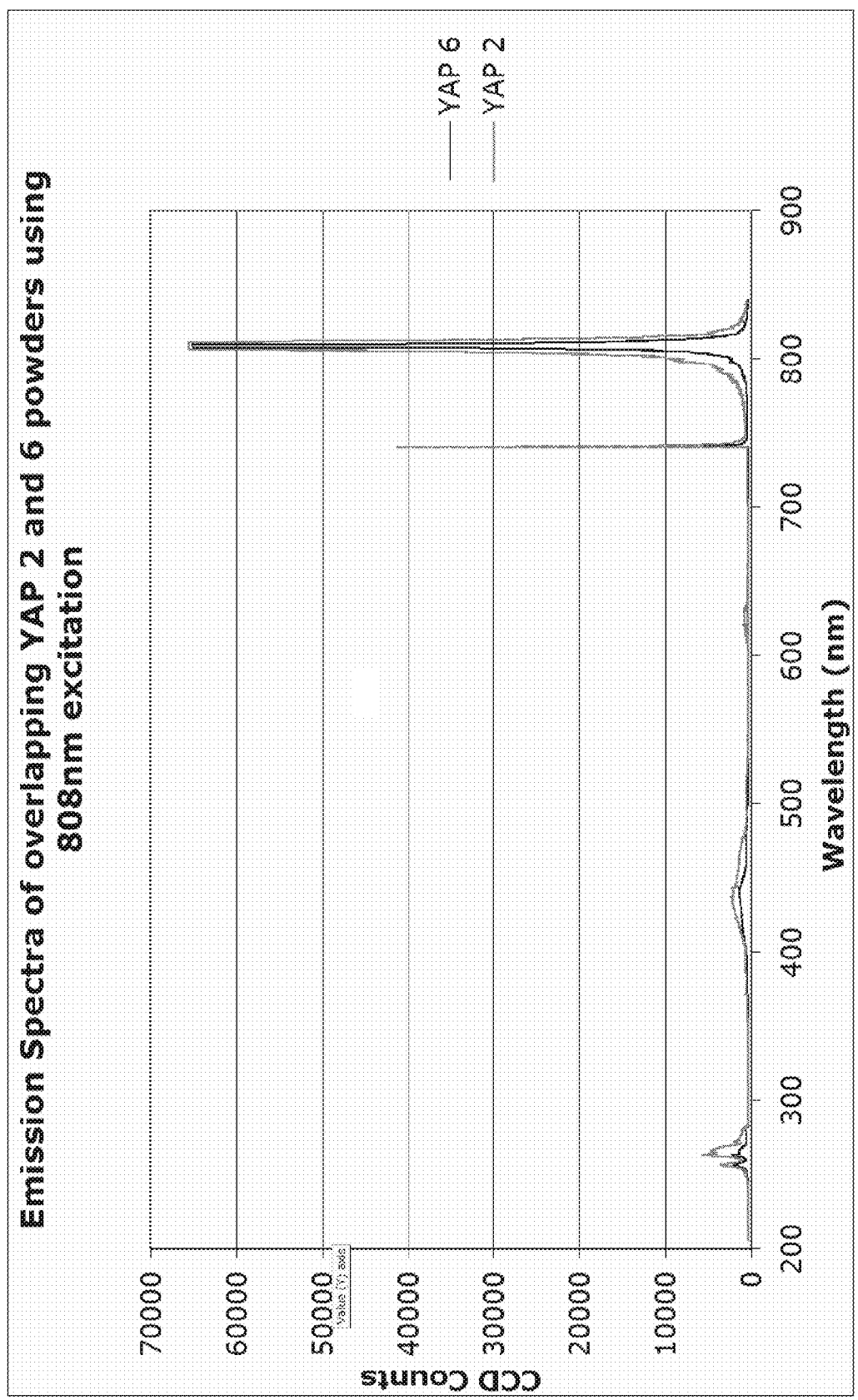
FIG. 30($a$) is a graph of the emission spectra of YAP2 and YAP6 powder formulations resulting from an 808 nm excitation wavelength.
Figure 30B:
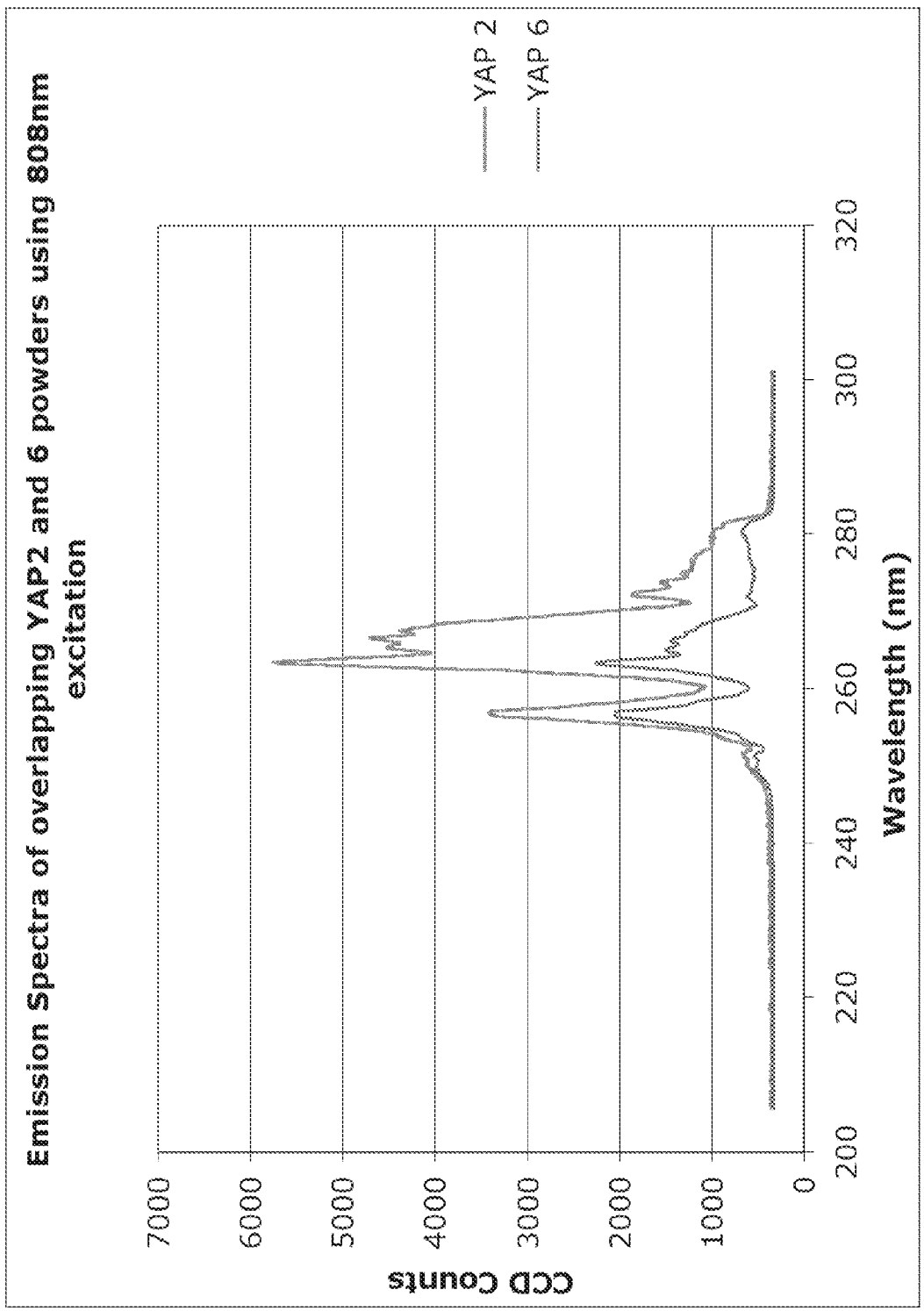
Figure 31A:
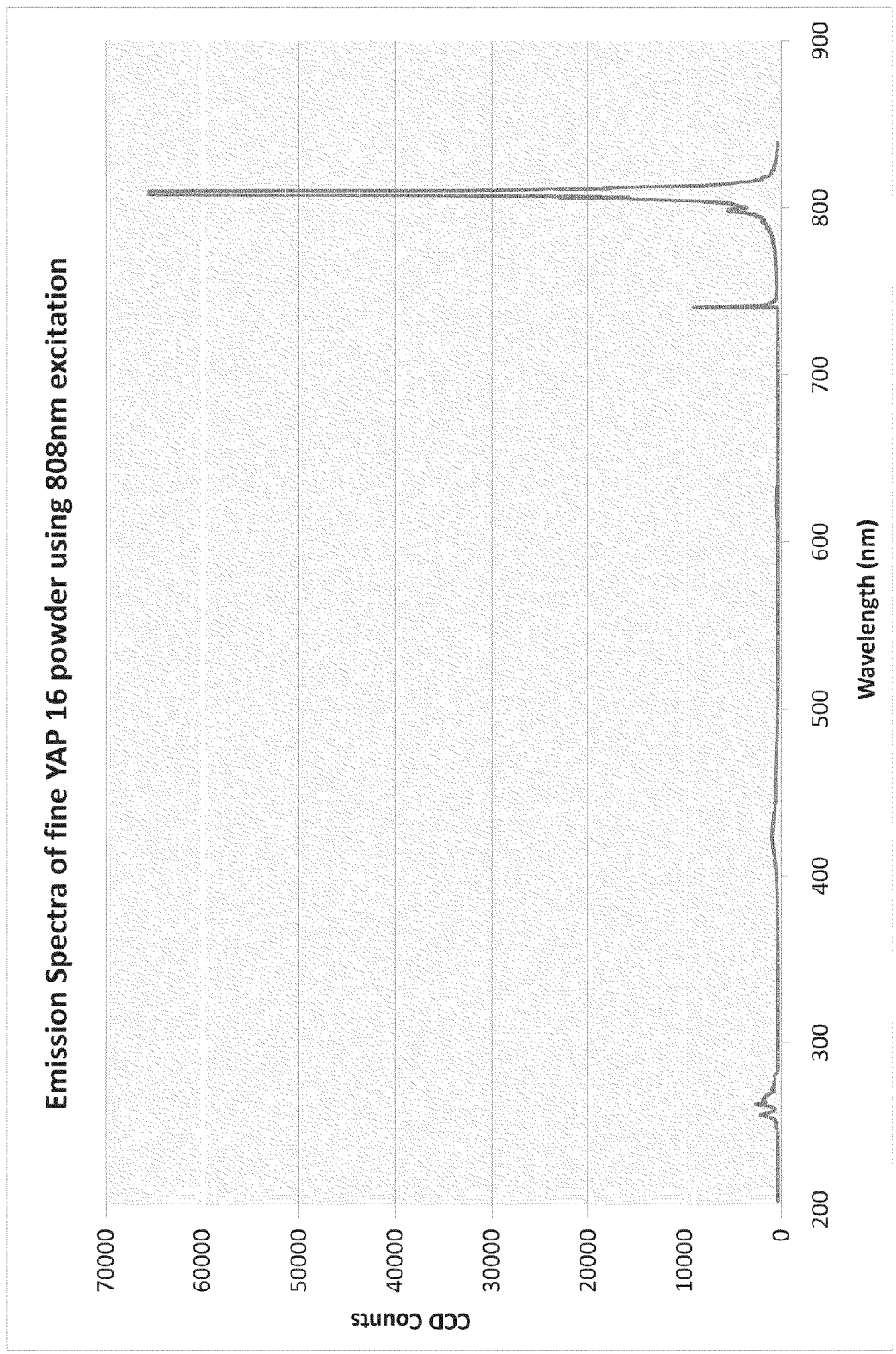
FIG. 31($a$) is a graph of the emission spectra of YAP16 powder formulation resulting from an 808 nm excitation wavelength.
Figure 31B:
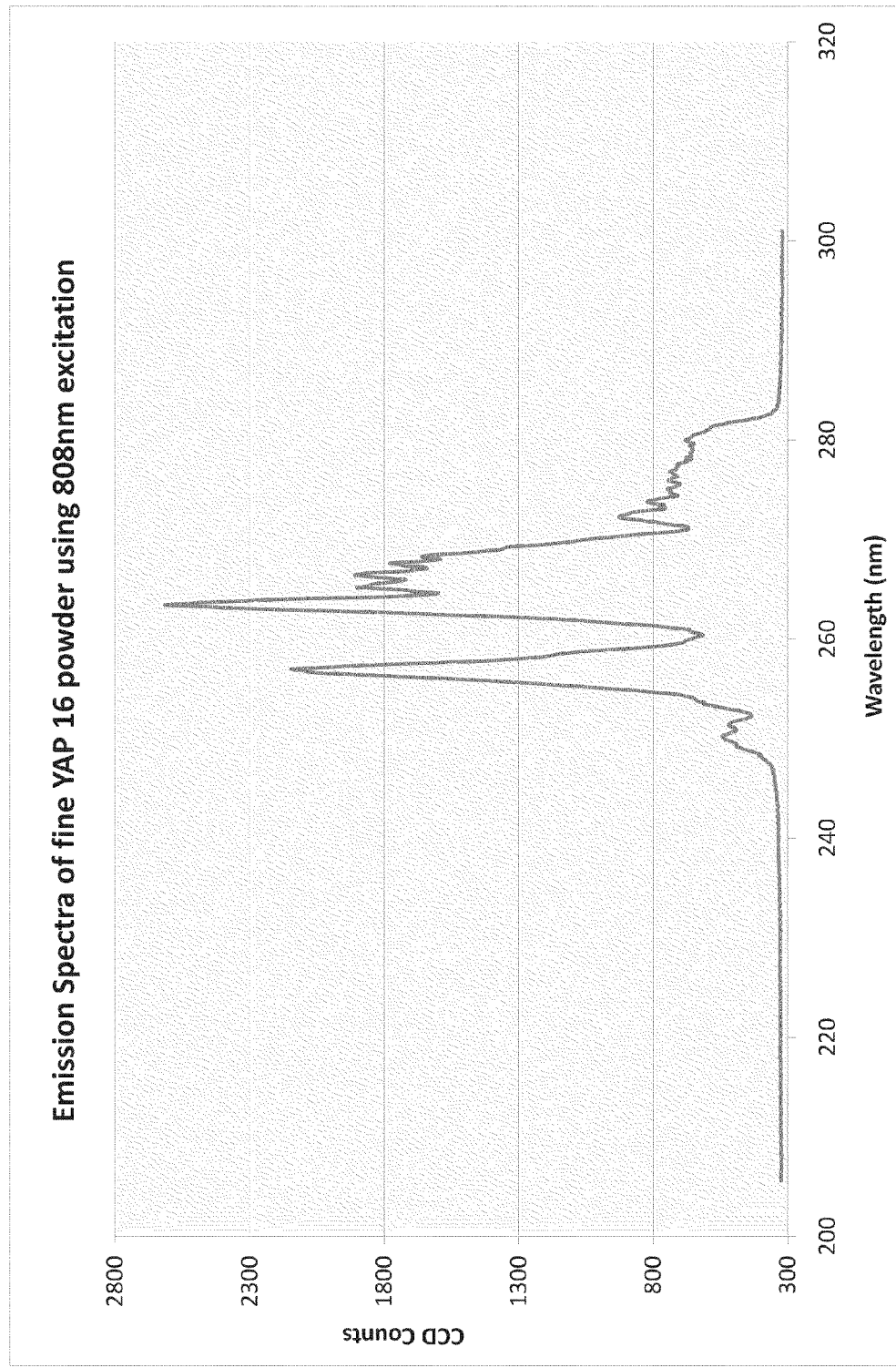
Figure 32:
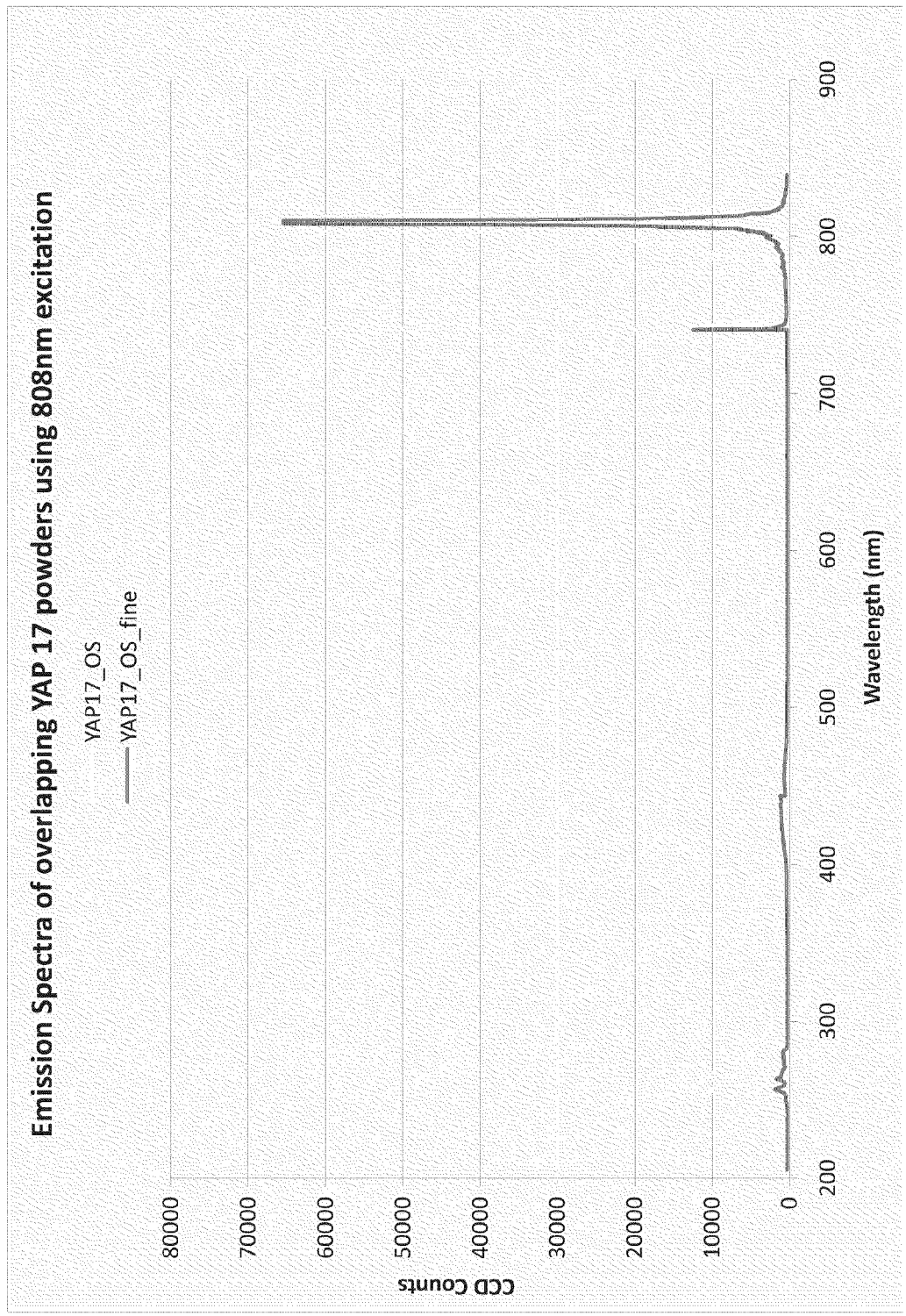
FIG. 32 is a graph of the emission spectra of YAP17 powder formulation resulting from an 808 nm excitation wavelength.
Figure 33:
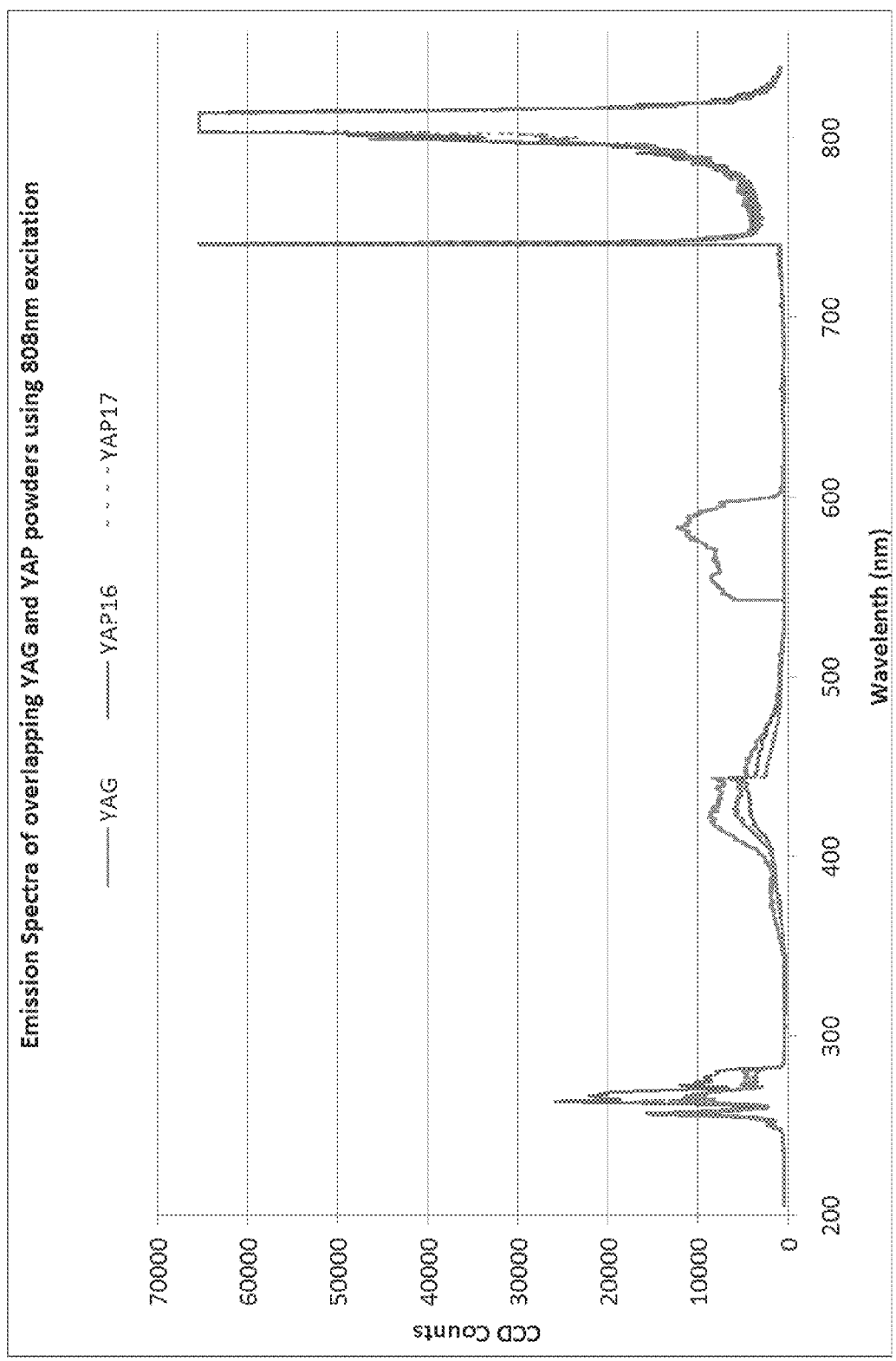
FIG. 33 is a graph of the emission spectra of YAG, YAP16, and YAP17 powder formulations resulting from an 808 nm excitation wavelength.
Figure 34:
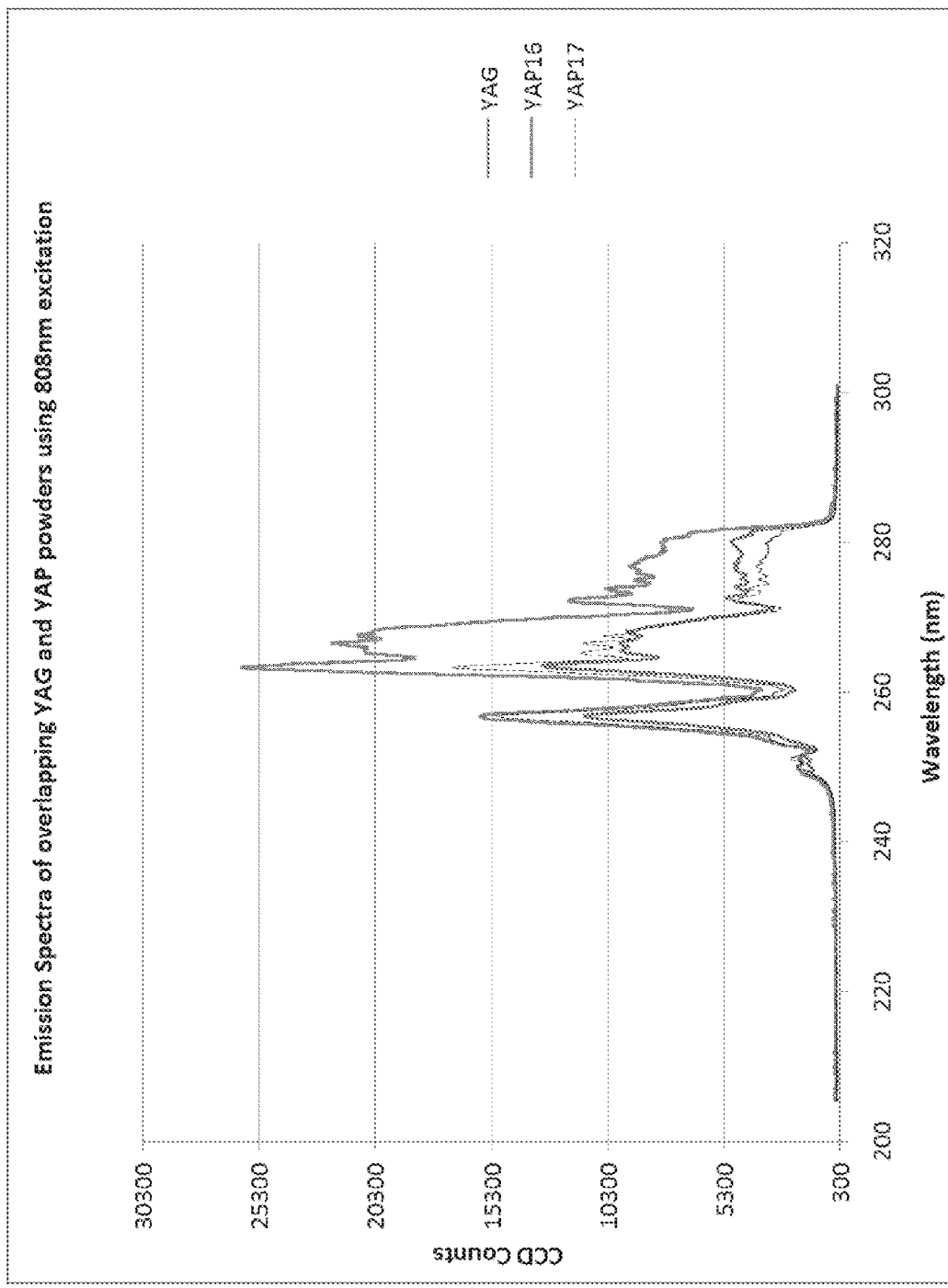
FIG. 34 is a graph of the emission spectra of YAG, YAP16, and YAP17 powder formulations resulting from an 808 nm excitation wavelength.

In one aspect of the invention, control samples are evaluated using the Raman system to ensure that up-conversion originates from the doped formulations and not from the raw materials or from the equipment. FIGS. 12 and 13 show that no up-conversion was observed for the raw starting materials. FIG. 14 shows that no up-conversion was observed from a glass slide. FIG. 15-18 show that LuAg powders produced up-conversion in the range of 240-640 nm using a 808 nm excitation source. FIG. 19-34 show that all of the YAP modified formulations processed under the methods described above resulted in up-conversion behavior when exposed to 808 nm excitation. Table 4, below, shows the maximum UV peak wavelength for select formulations. The emission intensity values are within the UV-C range, which is needed for killing bacteria and viruses.

TABLE 4

Maximum UV Peak Wavelength (λ) for Select Formulations

| YAP# | Excitation Wavelength (nm) | λ (nm) | λ (nm) | λ (nm) | λ (nm) |
|---|---|---|---|---|---|
| 1 | 808 | 233 | 255 | 275 | |
| 2 | 808 | 233 | 264 | 281 | |
| 3 | 808 | 233 | 266 | 278 | |
| 4 | 808 | 233 | 256 | 276 | |
| 5 | 808 | 233 | 246 | 281 | |
| 6 | 808 | 236 | 249 | 275 | |
| 7 | 808 | 233 | 255 | 268 | 279 |
| 8 | 808 | 233 | 259 | 278 | |
| 9 | 808 | 233 | 267 | 280 | |
| 10 | 808 | 233 | 247 | 260 | 274 |
| 11 | 808 | 233 | 245 | 257 | 270 |
| 12 | 808 | | | | |
| 13 | 808 | 233 | 251 | 269 | 280 |
| 14 | 808 | 233 | 268 | 279 | |
| 15 (YAG) | 808 | 233 | 248 | 279 | |
| 16 | 808 | 233 | 246 | 264 | 276 |
| 17 | 808 | 233 | 245 | 256 | 279 |
| LuAG | 808 | 233 | 248 | 261 | 280 |

An additional method of testing may also be used. A pellet of the up-conversion material may be placed on an inoculated agar plate. Light is then directed on the pellet. The area where the pellet is placed is free of bacteria, which shows that the pellet up-converted the light into the proper UV spectrum. The UV emittance from the pellet killed the prior inoculated area.

Another aspect of the invention provides for taking the up-converting powders as described above to make different composite coatings using a variety of formulations listed in Tables 1-3 above and including the LuAG formulation.

Figure 35:
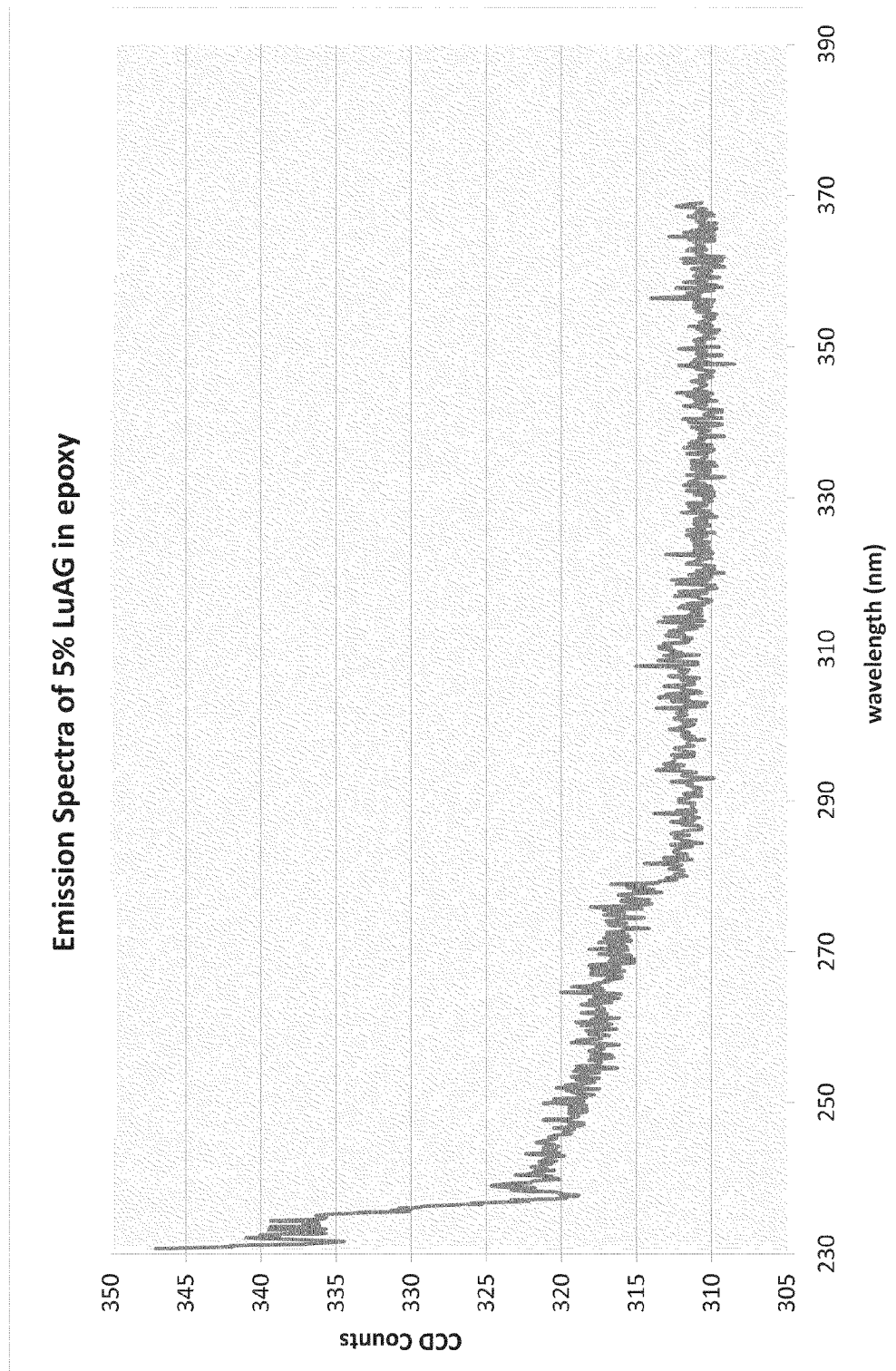
FIG. 35 is a graph of emission spectra of 5 wt % LuAG epoxy using 808 nm excitation.
Figure 36:
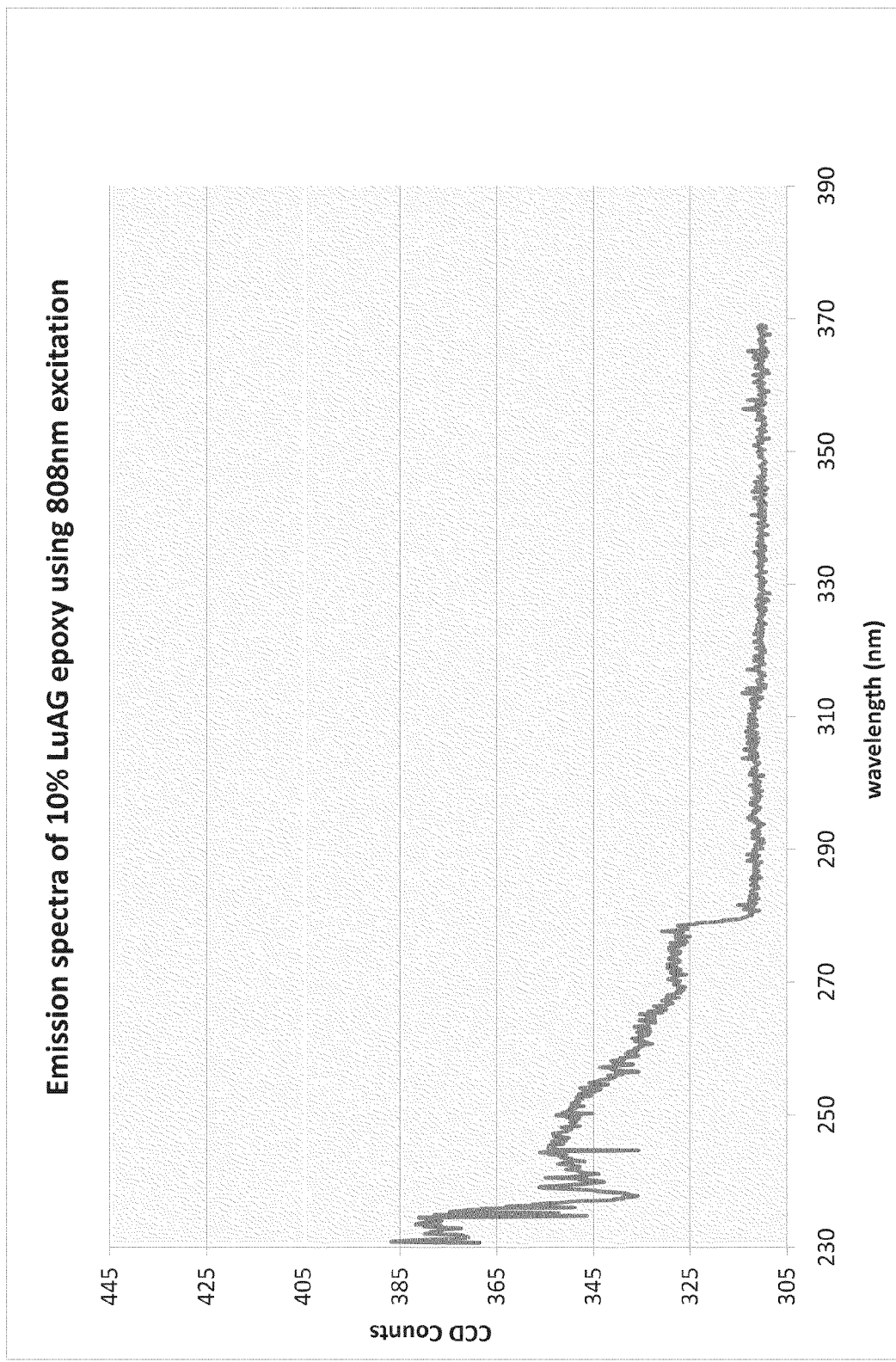
FIG. 36 is a graph of emission spectra of 10 wt % LuAG epoxy using 808 nm excitation.
Figure 37:
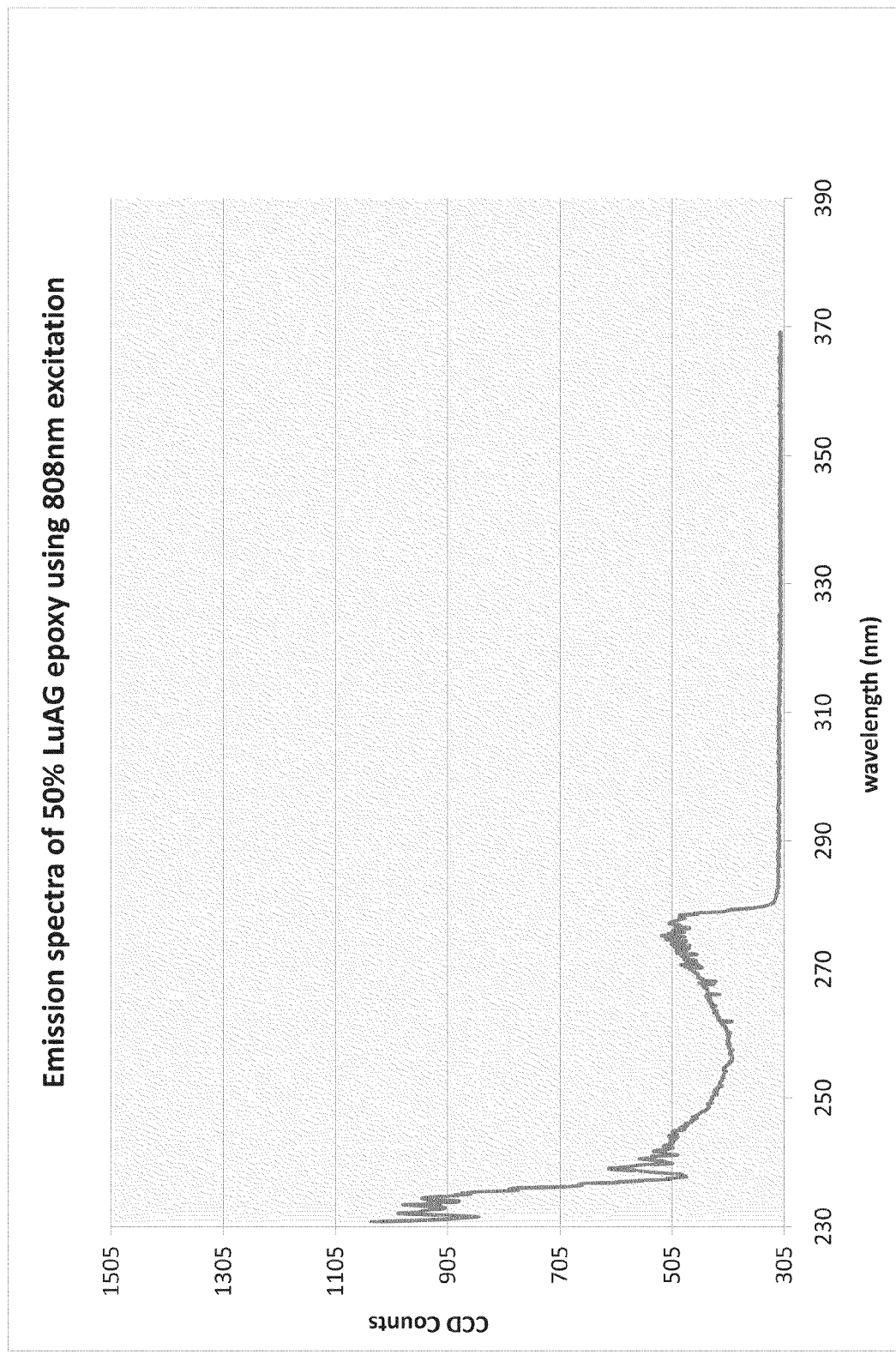
FIG. 37 is a graph of emission spectra of 50 wt % LuAG epoxy using 808 nm excitation.

FIG. 35-37 display images and emission spectra for 5, 10, and 50 wt % LuAG in epoxy using 808 nm excitation.

Figure 38:
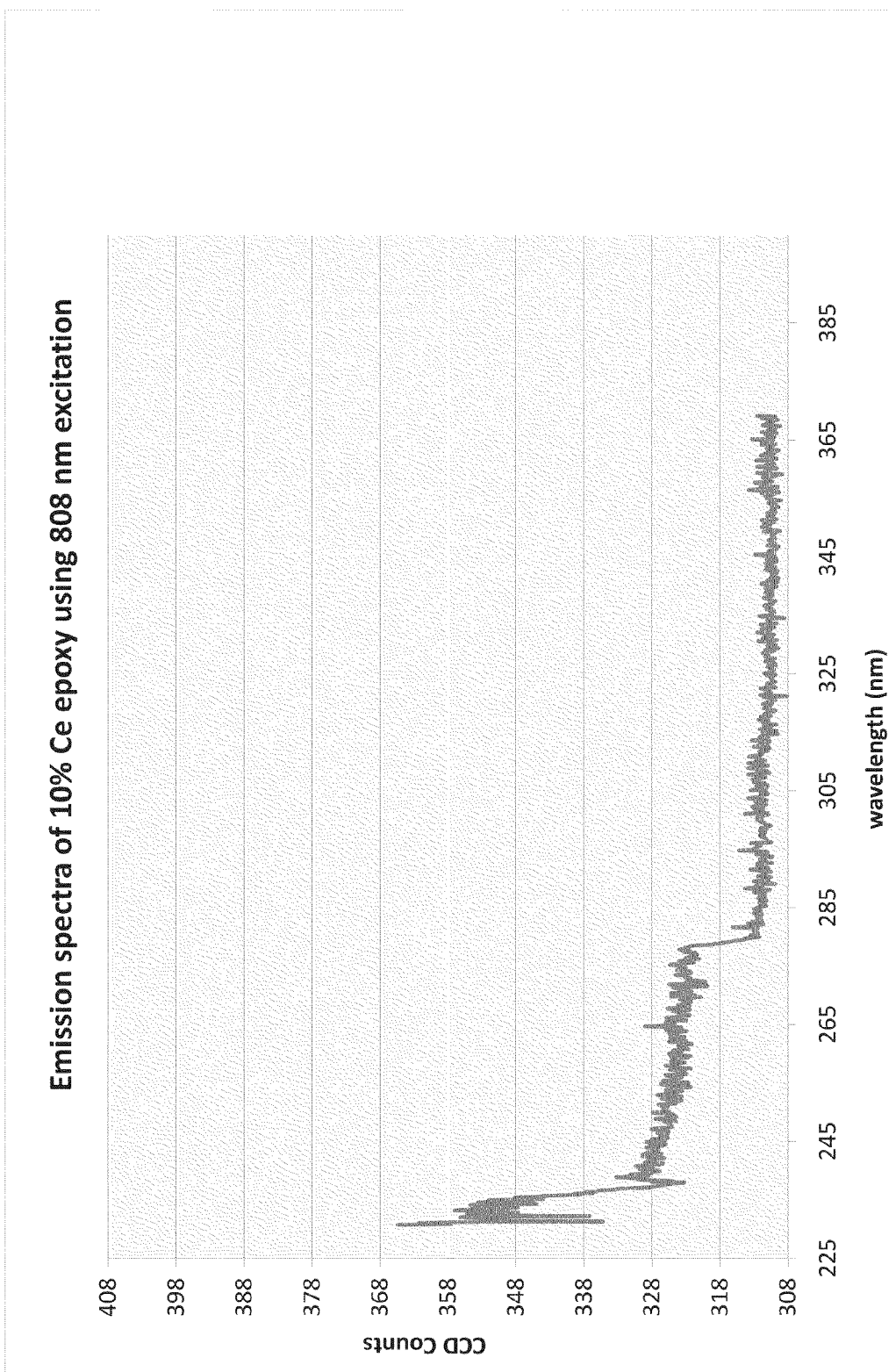
FIG. 38 is a graph of emission spectra of 10 wt % Ce epoxy using 808 nm excitation.
Figure 39:
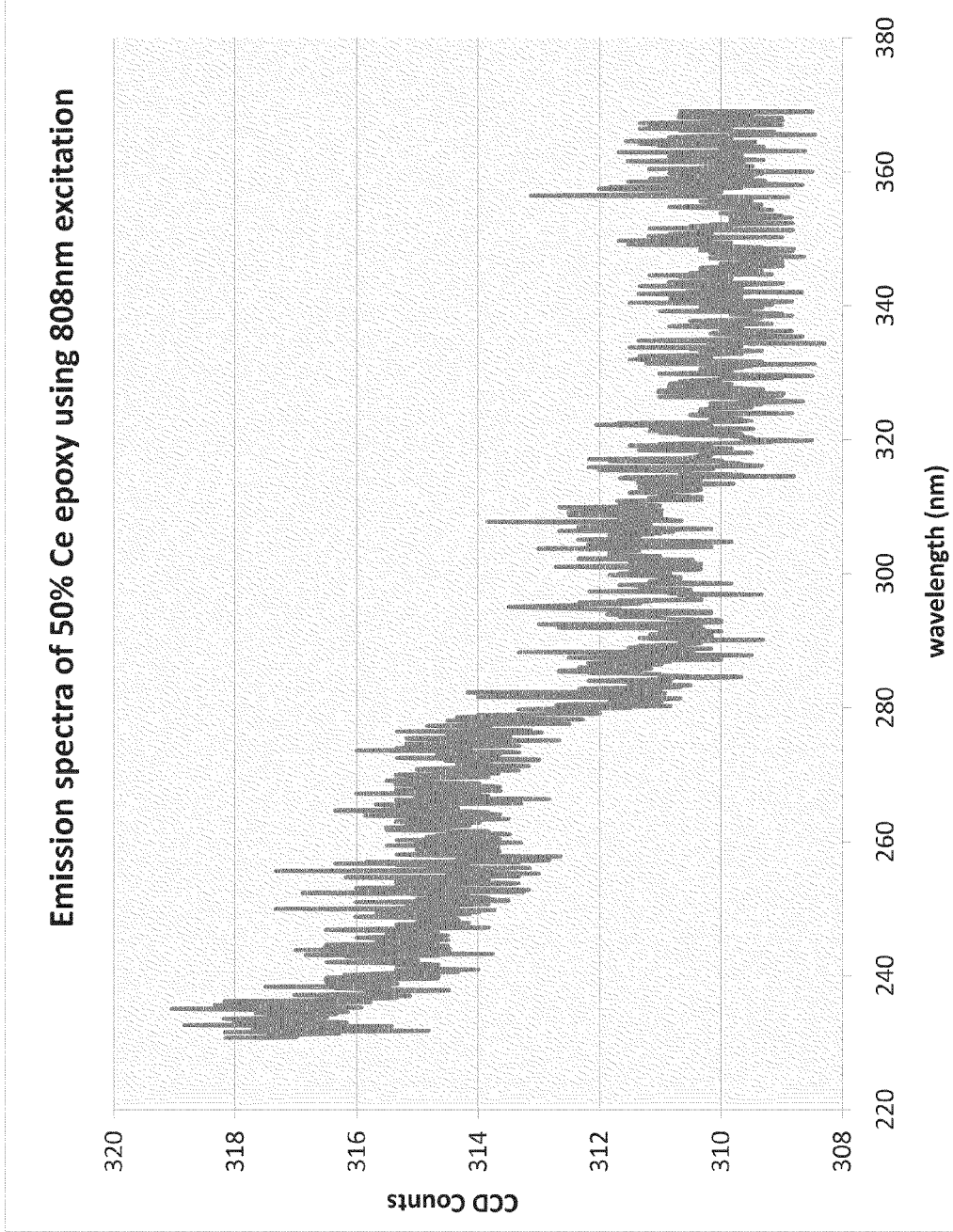
FIG. 39 is a graph of emission spectra of 50 wt % Ce epoxy using 808 nm excitation.

FIG. 38-39 display images and emission spectra for 10 and 50 wt % Ce in epoxy using 808 nm excitation.

Figure 40:
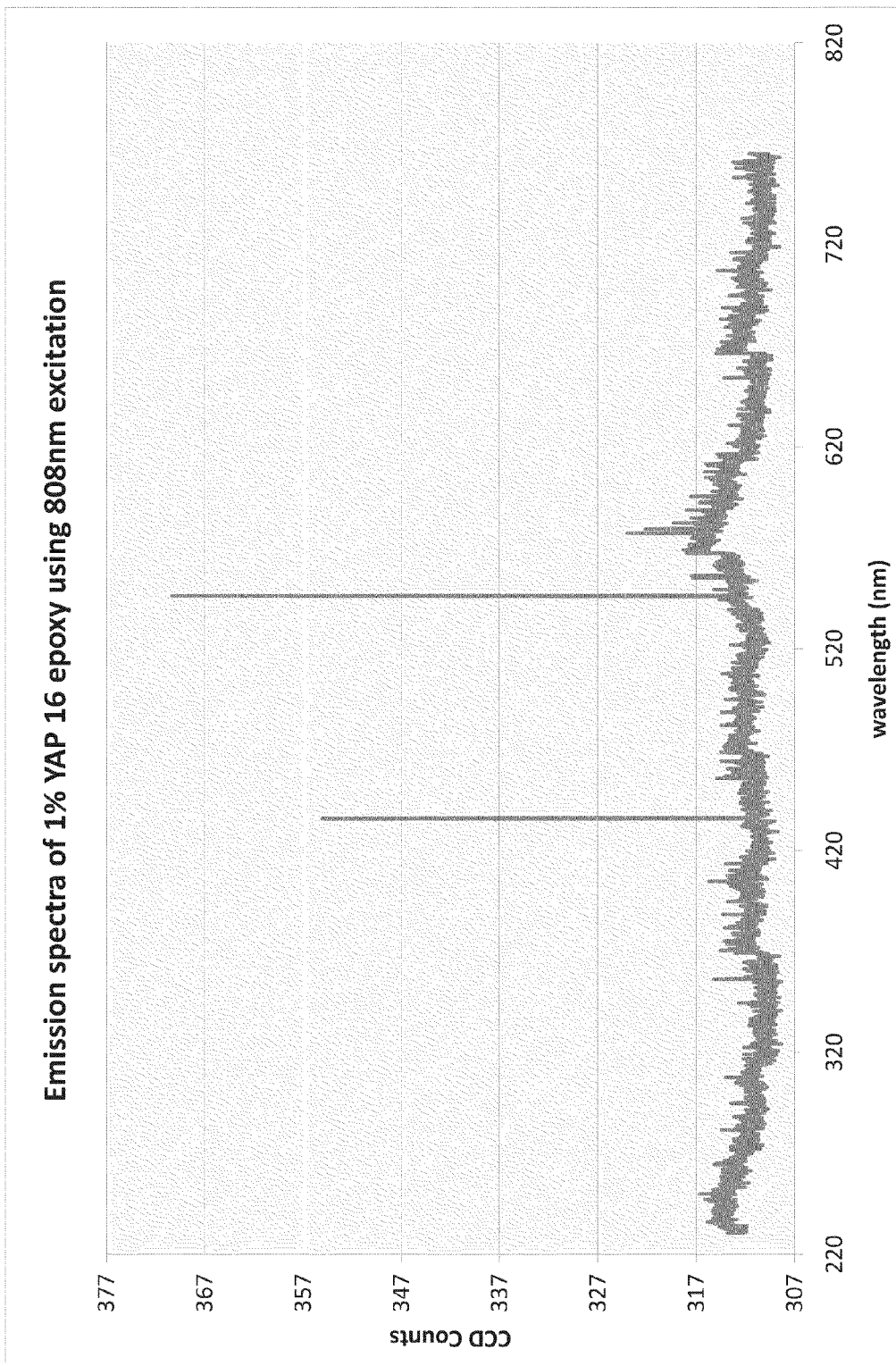
FIG. 40 is a graph of emission spectra of 1 wt % YAP16 epoxy using 808 nm excitation.

FIG. 40 displays an image and emission spectra for 1 wt % YAP16 in epoxy using 808 nm excitation.

Figure 41:
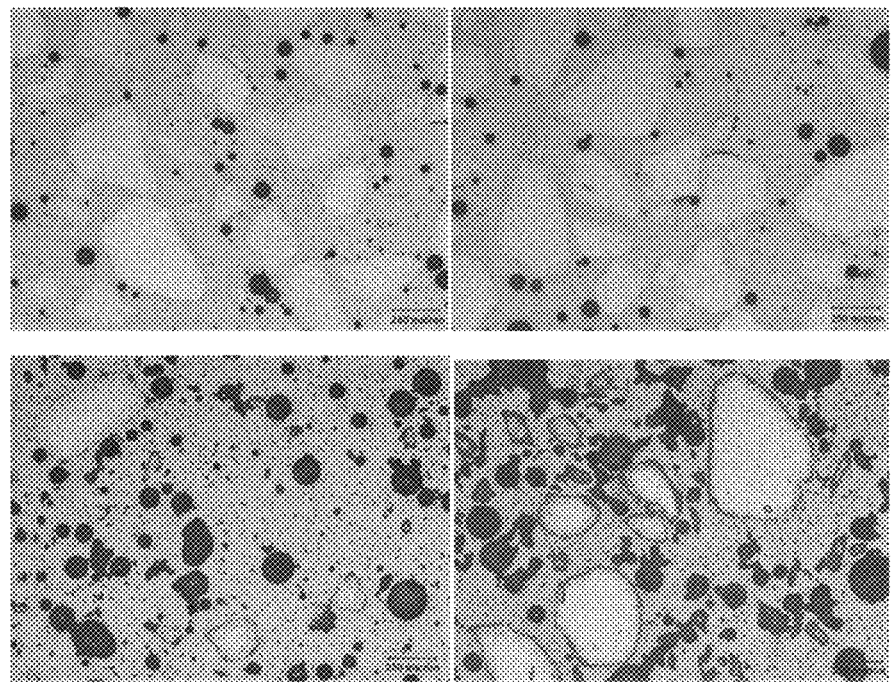
FIG. 41 is a photo illustration of an epoxy with (a) 25 volume % YAP 16 (top left), 50 volume % YAP 16 (top right), 25 volume % YAP 16 with Dispersant (bottom left), 50 volume % YAP 16 Dispersant (bottom right).

FIG. 41 shows photos of YAP16 incorporated into epoxy at 25 wt % and 50 wt %.

Figure 42:
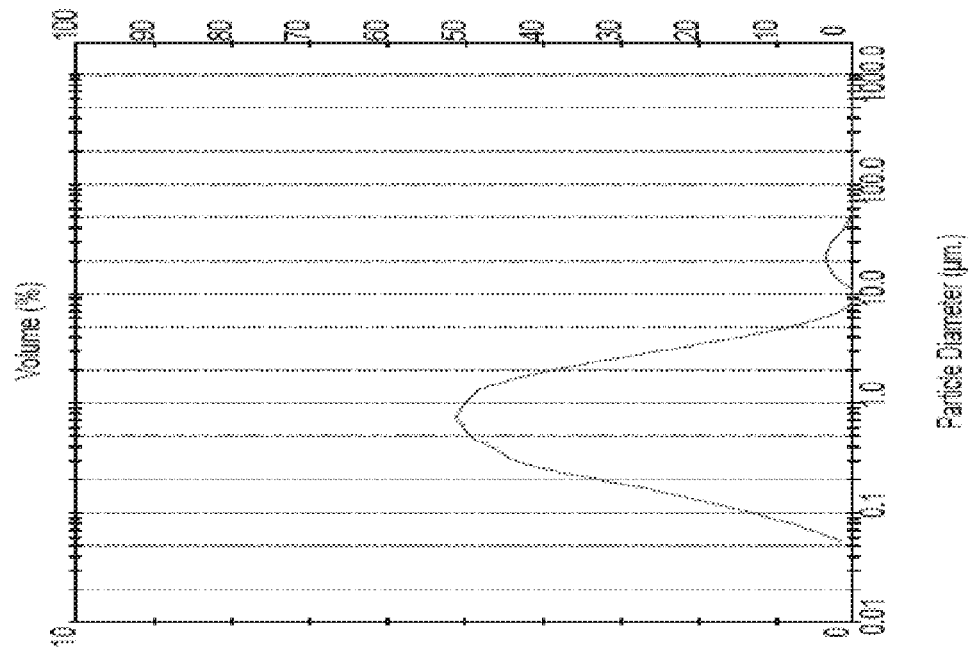
FIG. 42 is a graph and an accompanying table illustrating the particle size distribution for a YAP 18 powder formulation showing the average particle size is less than 1 um.

FIG. 42 shows particle size distribution for YAP 18 powder formulation showing the average particle size is less than 1 um.

Figure 43:
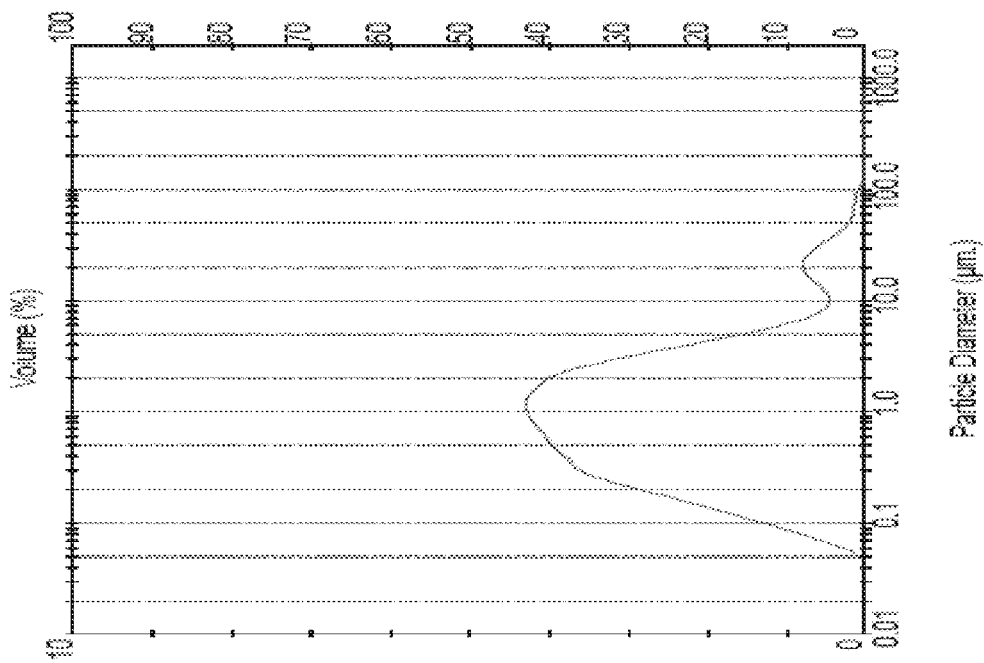
FIG. 43 is a graph and an accompanying table illustrating the particle size distribution for a YAP 19 powder formulation showing the average particle size is less than 1 um.

FIG. 43 shows particle size distribution for YAP 19 powder formulation showing the average particle size is less than 1 um.

The embodiments of the present invention has been set forth in the drawings and specification and although specific terms are employed, these are used in the generically descriptive sense only and are not used for the purposes of limitation. Changes in the formed proportion of parts as well as in the substitution of equivalents are contemplated as circumstances may suggest or are rendered expedient without departing from the spirit scope of the invention as further defined in the following claims.

What is claimed is:

1. A system adapted to convert impinging wavelengths of radiation to wavelength energies sufficient for use in antimicrobial applications, the system comprising:
  a material formulation having an up-conversion constituent comprising a combination of $ZrO_2$ and $Eu_2O_3$; and
  an ultraviolet emission response from up-conversion of radiation from a radiation source, the emission response having wavelengths in a range from 200-450 nm to kill bacteria and viruses.

2. The system of claim 1 wherein the $ZrO_2$ in the material formulation is an amount ranging from 90% to 99% by mole.

3. The system of claim 1 wherein the combination of the up-conversion constituent further comprises $Yb_2O_3$.

4. The system of claim 3 wherein a ratio of $Yb_2O_3$ to $Eu_2O_3$ is between 5:1 and 10:1.

5. The system of claim 3 wherein a ratio of $Yb_2O_3$ to $Eu_2O_3$ is between 1:5 and 1:1.

6. The system of claim 1 wherein the material formulation is applied as a vapor formed generally by evaporating the material formulation.

7. The system of claim 1 wherein the material formulation is applied by physical vapor deposition comprising sputtering.

8. The system of claim 1 further comprising a host material comprising one or more materials selected from the group consisting essentially of polyurethanes, polycarbonates, and polysilanes.

9. The system of claim 1 further comprising a host material comprising one or more materials selected from the group consisting essentially of epoxy, paint, and urethane.

10. The system of claim 1 wherein the material formulation is a powder comprising a compilation of individual, compact granules.

11. A method for providing an antimicrobial response from a coating or surface using the impinging radiation comprising:
  providing a host material with an up-converting constituent comprising a combination of $ZrO_2$, $Eu_2O_3$, and $Yb_2O_3$;
  vapor depositing the host material onto a surface;
  up-converting radiation impinging on the host material to higher energy radiation having a range generally from 200-450 nm; and
  emitting the radiation as an antimicrobial emission response to kill microorganisms on or near the host material.

12. The method of claim 11 wherein the host material comprises a rare earth material formed by combining one or more materials selected from the group consisting essentially of $Al_2O_3$, $Y_2O_3$, $CeO_2$, $Yb_2O_3$, $Eu_2O_3$, $Gd_2O_3$, $CaCO_3$, $Nd_2O_3$, $Er_2O_3$, $YAlO_3$, $Al_5Lu_3O_{12}$, and $Al(OH)_3$.

13. The method of claim 11 further comprising physical vapor depositing the host material onto a surface by sputtering.

14. The method of claim 11 wherein combined amount of the $Eu_2O_3$, and the $Yb_2O_3$ ranges from 1% to 10% by mole.

15. The method of claim 11 wherein the host material comprises one or more materials selected from the group consisting essentially of sulfides, oxides, borides and fluorides.

16. The method of claim 11 wherein the host material comprises one or more materials selected from the group consisting essentially of phosphate glass, soda-lime-silicate, alumina, hafnia, zirconia, silica, and titania.

17. The method of claim 11 wherein the host material comprises one or more oxides selected from the group consisting essentially of Scandium (Sc) Yttrium (Y), Lanthanum (La), Cerium (Ce), Praseodymium (Pr), Neodymium (Nd), Promethium (Pm), Samarium (Sm), Europium (Eu), (Gd), Terbium (Tb), Dysprosium (Dy), Holmium (Ho), Erbium (Er), Thulium (Tm), Ytterbium (Yb), and Lutetium (Lu).

18. A system for converting impinging wavelengths of radiation to wavelength energies sufficient for antimicrobial applications, the system comprising:
  a host material comprising a combination of an activator of $Eu_2O_3$ and an up-converting constituent of $ZrO_2$;
  a vapor deposition of the host material for depositing onto a surface;
  radiation impinging the host material on the surface;
  an ultraviolet emission response having a range generally from 200-450 nm from up-conversion of the radiation impinging the host material on the surface;
  wherein the ultraviolet emission response is configured to kill bacteria on or near the surface.

19. The system of claim 18 wherein the up-converting constituent comprises 90%-99% of the vapor deposition by mole.

20. The system of claim 19 further comprising a sensitizer comprised of $Yb_2O_3$.

* * * * *